(12) United States Patent
Schoettle et al.

(10) Patent No.: US 10,660,852 B2
(45) Date of Patent: May 26, 2020

(54) EXPRESSION AND FOLDING IN THE MANUFACTURING PROCESS OF CD-RAP BY USING A CD-RAP PRECURSOR PROTEIN

(71) Applicant: BIONET PHARMA GMBH, Munich (DE)

(72) Inventors: Isabell Schoettle, Frankfurt am Main (DE); Judith Stommes, Frankfurt am Main (DE); Paul Habermann, Frankfurt am Main (DE); Bernd Janocha, Frankfurt am Main (DE); Ursula Stillger, Frankfurt am Main (DE); Eckart Bartnik, Frankfurt am Main (DE); Volker Jeske, Frankfurt am Main (DE); Joachim Saas, Frankfurt am Main (DE)

(73) Assignee: BIONET PHARMA GMBH, Munich (DE)

( * ) Notice: Subject to any disclaimer, the term of this patent is extended or adjusted under 35 U.S.C. 154(b) by 0 days.

(21) Appl. No.: 15/760,321

(22) PCT Filed: Sep. 16, 2016

(86) PCT No.: PCT/EP2016/071947
§ 371 (c)(1),
(2) Date: Mar. 15, 2018

(87) PCT Pub. No.: WO2017/046314
PCT Pub. Date: Mar. 23, 2017

(65) Prior Publication Data
US 2019/0046442 A1    Feb. 14, 2019

(30) Foreign Application Priority Data

Sep. 18, 2015 (EP) .................................... 15306457
Sep. 18, 2015 (EP) .................................... 15306458
Dec. 7, 2015 (EP) .................................... 15306950

(51) Int. Cl.
| | | |
|---|---|---|
| *A61K 9/19* | (2006.01) | |
| *C12P 21/02* | (2006.01) | |
| *C07K 14/00* | (2006.01) | |
| *A61K 38/17* | (2006.01) | |
| *C07K 14/435* | (2006.01) | |
| *A61K 38/00* | (2006.01) | |
| *A61K 9/127* | (2006.01) | |
| *A61K 47/18* | (2017.01) | |
| *A61K 47/14* | (2017.01) | |
| *A61K 9/00* | (2006.01) | |

(52) U.S. Cl.
CPC ............ *A61K 9/127* (2013.01); *A61K 9/1272* (2013.01); *A61K 9/1277* (2013.01); *A61K 9/19* (2013.01); *A61K 38/17* (2013.01); *A61K 47/14* (2013.01); *A61K 47/183* (2013.01); *C07K 14/00* (2013.01); *C07K 14/435* (2013.01); *C12P 21/02* (2013.01); *A61K 9/0019* (2013.01); *A61K 38/00* (2013.01)

(58) Field of Classification Search
CPC ........ C07K 14/435; A61K 38/17; C12P 21/02
See application file for complete search history.

(56) References Cited

FOREIGN PATENT DOCUMENTS

| | | |
|---|---|---|
| EP | 1191099 | 3/2002 |
| EP | 1604693 | 12/2005 |
| WO | 2008040556 | 4/2008 |
| WO | 2011113604 | 9/2011 |
| WO | 2011134979 | 11/2011 |

OTHER PUBLICATIONS

Blesch et al., "Cloning of a novel malignant melanoma-derived growth-regulatory protein, MIA", Cancer research 54.21 (1994): 5695-5701.
Laouini et al., "Preparation, characterization and applications of liposomes: state of the art", Journal of Colloid Science and Biotechnology 1.2 (2012): 147-168.
International Application No. PCT/EP2016/071947, International Search Report and Written Opinion dated Apr. 28, 2017.
Yonekawa et al., "Serum cartilage-derived retinoic acid-sensitive protein (CD-RAP) levels in Swarm rat chondrosarcoma", Journal of Orthopaedic research 20.2 (2002): 382-386.
Altschul et al., "Basic Local Alignment Search Tool", Journal of Molecular Biology, vol. 215, No. 3, Oct. 5, 1990, pp. 403-410.
Altschul et al., "Gapped BLAST and PSI-BLAST: A New Generation of Protein Database Search Programs", Nucleic Acids Research, vol. 25, No. 17, Sep. 1, 1997, pp. 3389-3402.
Blesch et al., "Cloning of a Novel Malignant Melanoma-derived Growth-Regulatory Protein, MIA", Cancer Research, vol. 54, No. 21, Nov. 1, 1994, pp. 5695-5701.
Brudno et al., "Glocal Alignment: Finding Rearrangements During Alignment", Bioinformatics, vol. 19, No. 1, Jul. 3, 2003, pp. i54-i62.
Dietz et al., "Cloning of a Retinoic Acid-sensitive mRNA Expressed in Cartilage and During Chondrogenesis", The Journal Biological Chemistry, vol. 271, No. 6, Feb. 9, 1996, pp. 3311-3316.
Janin, "Surface and Inside Volumes in Globular Proteins", Nature, vol. 277, Feb. 8, 1979, pp. 491-492.

(Continued)

*Primary Examiner* — Elly-Gerald Stoica
(74) *Attorney, Agent, or Firm* — Kilpatrick Townsend & Stockton LLP

(57) ABSTRACT

The present invention relates to a CD-RAP precursor protein comprising a pre-sequence and CD-RAP, and its use in manufacturing of native CD-RAP. The present invention further relates to a composition comprising CD-RAP and at least one positively charged amino acid and a buffer, pharmaceuticals comprising said composition, their use in methods of treating and/or preventing cartilage disease or injury in patients suffering from aggrecan degradation, and/or increased influx of water into the cartilage, and/or decreased CD-RAP expression, as well as methods of producing said composition and methods of storing CD-RAP in said composition. The present invention further relates to a composition comprising liposomes comprising encapsulated CD-RAP or a variant thereof, its use in methods of treating joint disease or injury, and methods of producing such liposomal composition as well as storing CD-RAP therein.

Figure 1:
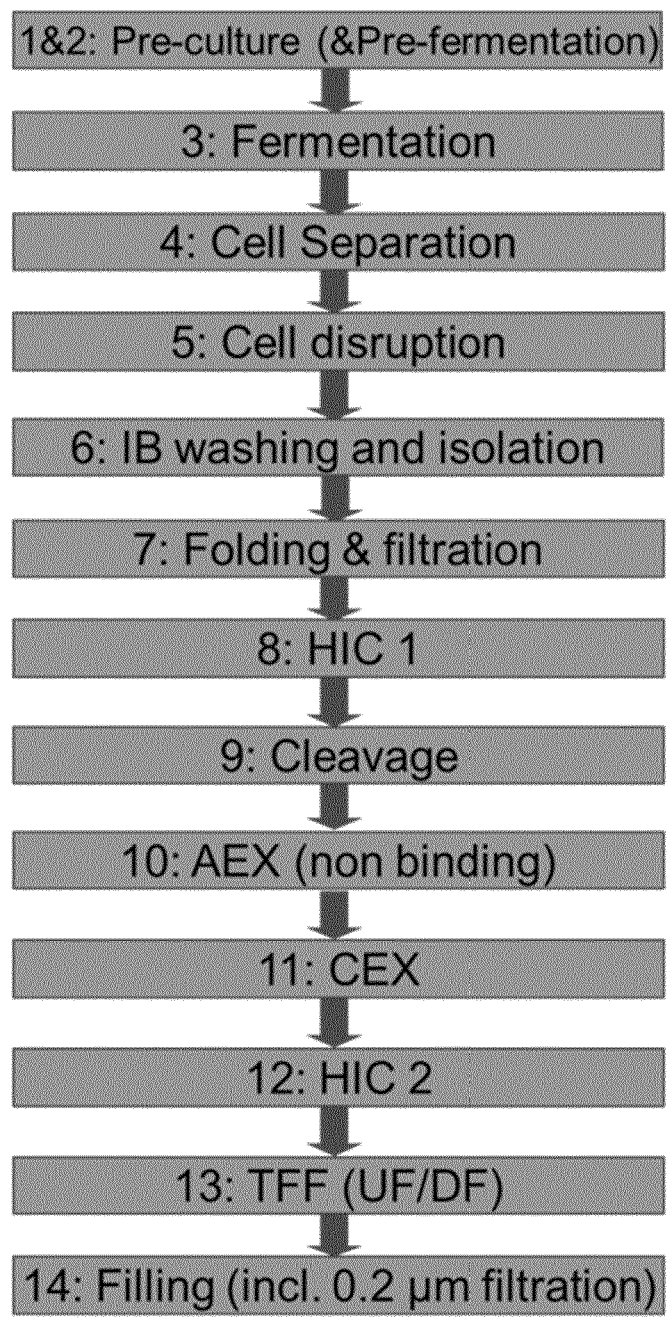

13 Claims, 33 Drawing Sheets
Specification includes a Sequence Listing.

(56) References Cited

OTHER PUBLICATIONS

Karlin et al., "Applications and Statistics for Multiple High-scoring Segments in Molecular Sequences", Proc. Natl. Acad. Sci. USA, vol. 90, No. 12, Jun. 15, 1993, pp. 5873-5877.
Kyte et al., "A Simple Method for Displaying the Hydropathic Character of a Protein", Journal of Molecular Biology, vol. 157, No. 1, May 5, 1982, pp. 105-132.
Lewis et al., "Ro 32-3555, an Orally Active Collagenase Inhibitor, Prevents Cartilage Breakdown in Vitro and in Vivo", British Journal of Pharmacology, vol. 121, No. 3, Jun. 1997, pp. 540-546.
Moser et al., "Ultrastructural Cartilage Abnormalities in MIA/CD-RAP—Deficient Mice", Molecular and Cellular Biology, vol. 22, No. 5, Mar. 2002, pp. 1438-1445.
Rao, "Recent Developments in the Design of Specific Matrix Metalloproteinase Inhibitors Aided by Structural and Computational Studies", Curr Pharm Des., vol. 11, No. 3, 2005, pp. 295-322.
Renkiewicz et al., "Broad-spectrum Matrix Metalloproteinase Inhibitor Marimastat-Induced Musculoskeletal Side Effects in Rats", Arthritis Rheum., vol. 48, No. 6, Jun. 2003, pp. 1742-1749.
Rose et al., "Hydrophobicity of Amino Acid Residues in Globular Proteins", Science, vol. 229, No. 4716, Aug. 30, 1985, pp. 834-838.
Schubert et al., "Modulation of Cartilage Differentiation by melanoma inhibiting activity/cartilage-derived retinoic acid-sensitive protein (MIA/CD-RAP)", Exp. Mol. Med., vol. 42, No. 3, Mar. 2010, pp. 166-174.
Thompson et al., "CLUSTAL W: improving the sensitivity of progressive multiple sequence alignment through sequence weighting, position-specific gap penalties and weight matrix choice", Nucleic Acids Res., vol. 22, No. 22, Nov. 11, 1994, pp. 4673-4680.
Tscheudschilsuren et al., "Regulation of Mesenchymal Stem Cell and Chondrocyte Differentiation by MIA", Exp Cell Res., vol. 312, No. 1, Jan. 1, 2006, pp. 63-72.
Weilbach et al., "Melanoma-inhibiting Activity Inhibits Cell Proliferation by Prolongation of the S-phase and Arrest of Cells in the G2 Compartment", Cancer Res., vol. 50, No. 21, Nov. 1, 1990, pp. 6981-6986.
Wolfenden et al., "Affinities of Amino Acid Side Chains for Solvent Water", Biochemistry, vol. 20, No. 4, Feb. 17, 1981, pp. 849-855.
Woolf et al., "Burden of Major Musculoskeletal Conditions", Bulletin of the World Health Organization, vol. 81, No. 9, 2003, pp. 646-656.

Fig. 2
A
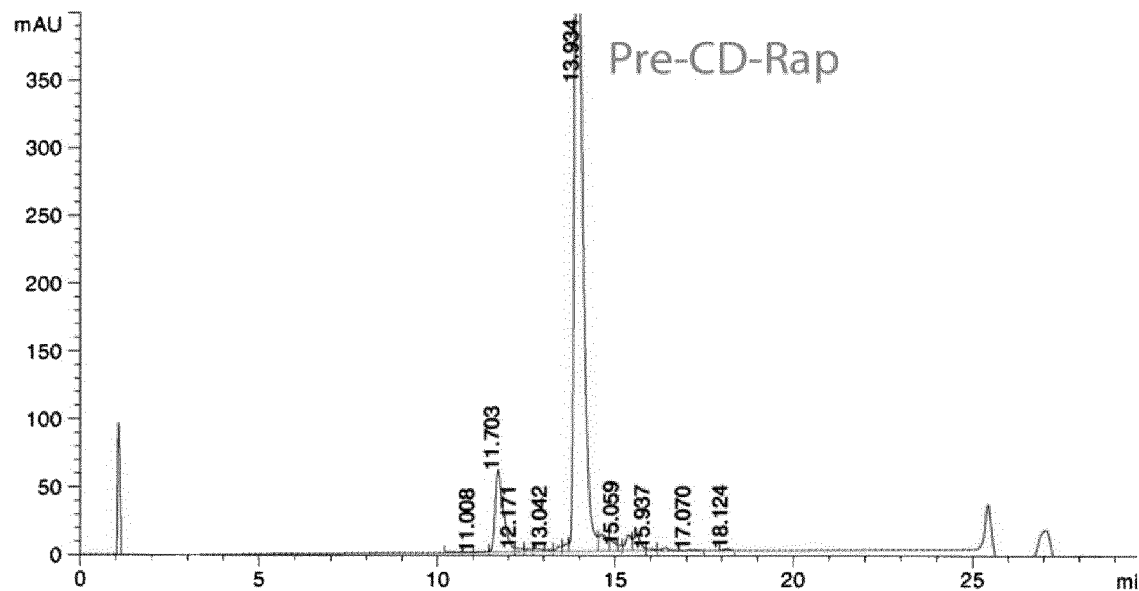
B
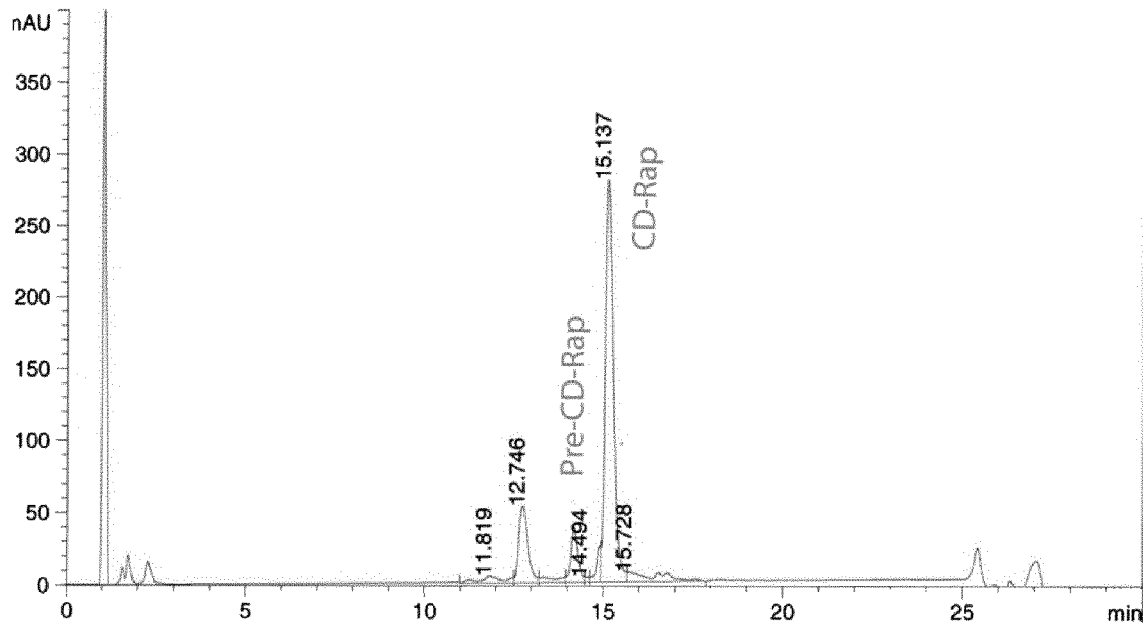

Fig. 3

| Construct | Pre-sequence | protein after fermentation [g/L] | Länge Präsequenz | GRAVY of pre-sequence | GRAVY of precursor protein |
|---|---|---|---|---|---|
| Konstrukt 2-9 | MATTSTGNSARFVNQHLHHH HHHHHGGGENQQQR | 2 | 34 | -1,61 | -0,29 |
| Konstrukt-3 | MATTSTGNSAR | 0,6 | 11 | -0,6 | -0,08 |
| Konstrukt 4 | MATTSTR | 0,5 | 7 | -0,52 | -0,06 |
| Konstrukt 12-9 | MATTSTLTTHWHWHGNSAR | 1,3 | 19 | -0,82 | -0,12 |
| Konstrukt 15-9 | MATTSTGNSAHFQHHHGSLA R | 1,2 | 21 | -0,74 | 0,11 |

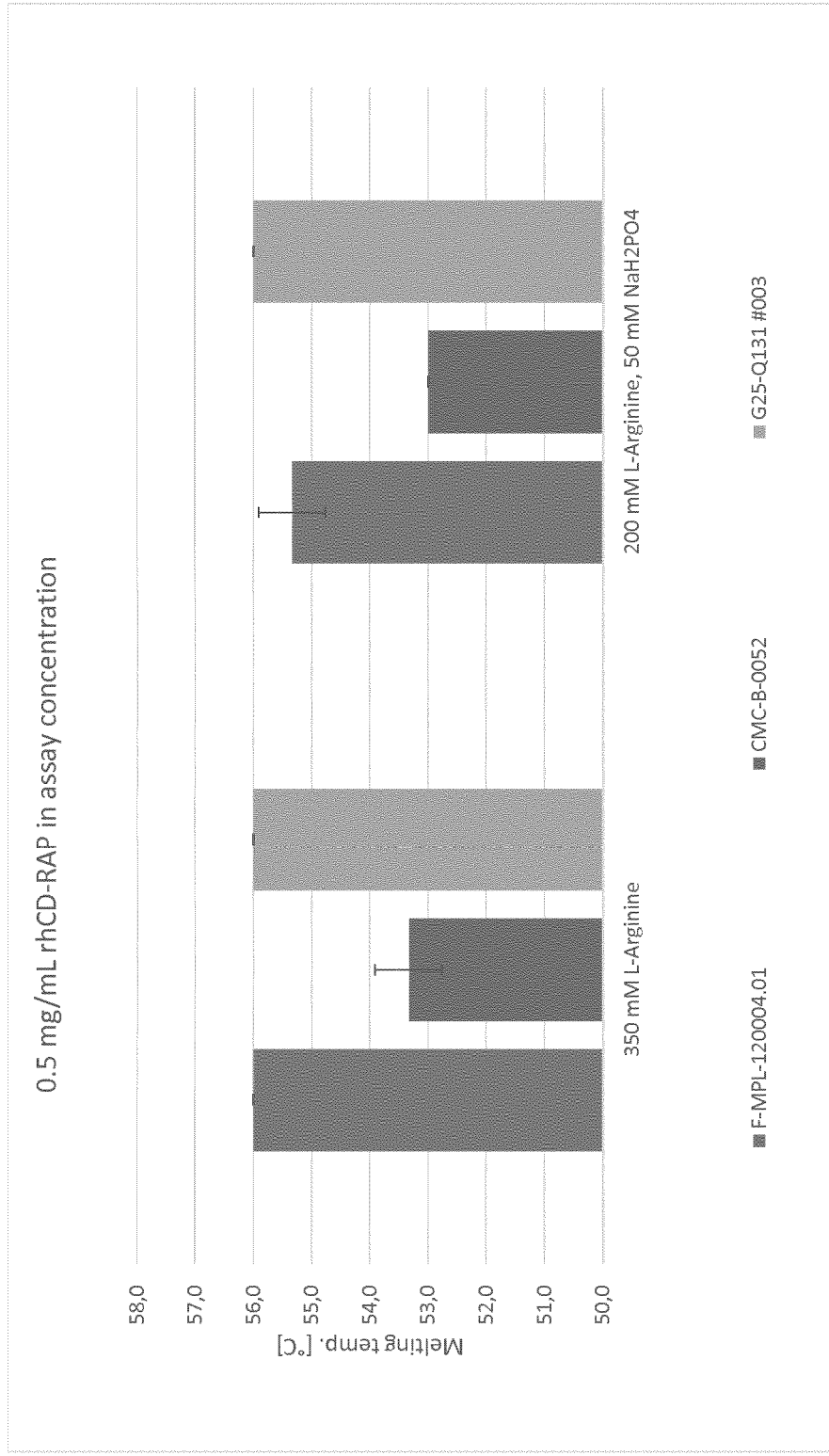

Fig. 9

| Formulation/batch number | Description | pH buffers | pH formulations | Osmolality (mOsm/kg) |
|---|---|---|---|---|
| F531-03-003P011-0 (F-AKO-120018A) | CD-RAP reference formulation in 50 mM sodium phosphate, pH 7.4, 350 mM arginine | NA | 7.3 | 452 |
| F531-03-003P011-1 | CD-RAP in 20 mM sodium phosphate, pH 6.5, 200 mM arginine | 6.5 | 6.7 | 426 |
| F531-03-003P011-2 | CD-RAP in 20 mM Citrate buffer, pH 6.5, 200 mM Arginine | 6.5 | 7.1 | 453 |
| F531-03-003P011-3 | CD-RAP in 20 mM Histidine buffer, pH 6.5, 200 mM arginine | 6.5 | 7.0 | 386 |
| F531-03-003P011-4 | CD-RAP in 20 mM sodium phosphate, pH 7.4, 85 mM arginine/85 mM glutamic acid + 35 Mm glutamic acid | 7.4 | 7.5 | 207 |
| F531-03-003P011-5 | CD-RAP in 20 mM sodium phosphate, pH 7.4, 200 mM arginine and 45 mg/ml sucrose | 7.4 | 7.5 | 597 |

Fig. 10

| Form. | Description | T=0 | | T=7d/40°C | | 5 F/T cycles | |
|---|---|---|---|---|---|---|---|
| | | Clarity | Color | Clarity | Color | Clarity | Color |
| 0 | CD-RAP reference formulation in 50 mM sodium phosphate, pH 7.4, 350 mM arginine | clear | colorless | Turbid (200-1000 NTU) | White | clear | colorless |
| 1 | CD-RAP in 20 mM sodium phosphate, pH 6.5, 200 mM Arginine | clear | colorless | Turbid (200-1000 NTU) | White | clear | colorless |
| 2 | CD-RAP in 20 mM Citrate buffer, pH 6.5, 200 mM arginine | clear | colorless | Turbid (~1000 NTU) | White | clear | colorless |
| 3 | CD-RAP in 20 mM Histidine buffer, pH 6.5, 200 mM arginine | clear | colorless | Turbid (~1000 NTU) | White | clear | colorless |
| 4 | CD-RAP in 20 mM sodium phosphate, pH 7.4, 85 mM arginine/85 mM glutamic acid + 35 Mm glutamic acid | clear | colorless | Turbid (~4000 NTU) | White | clear | colorless |
| 5 | CD-RAP in 20 mM sodium phosphate, pH 7.4, 200 mM arginine and 45 mg/ml sucrose | clear | colorless | Turbid (~1000 NTU) | Very slightly yellow | clear | colorless |

Fig. 11

| Form. | Description | Amount CD-RAP (mg/ml) | | | Area CD-RAP (%) | | | Total protein content (mg/ml) | | |
|---|---|---|---|---|---|---|---|---|---|---|
| | | t=0 | T=7d/ 40°C* | 5 F/T cycles* | t=0 | T=7d/ 40°C | 5 F/T cycles | t=0 | T=7d/ 40°C* | 5 F/T cycles* |
| 0 | CD-RAP reference formulation in 50 mM sodium phosphate, pH 7.4, 350 mM arginine | 2.4 | 1.5 (63%) | 1.8 (75%) | 43.1 | 43.8 | 40.4 | 5.5 | 3.4 (62%) | 4.4 (80%) |
| 1 | CD-RAP in 20 mM sodium phosphate, pH 6.5, 200 mM arginine | 1.7 | 1.0 (59%) | 1.5 (88%) | 38.2 | 43.2 | 35.0 | 4.5 | 2.4 (53%) | 4.2 (93%) |
| 2 | CD-RAP in 20 mM Citrate buffer, pH 6.5, 200 mM arginine | 1.7 | 1.1 (65%) | 1.5 (88%) | 39.1 | 43.2 | 36.8 | 4.4 | 2.6 (59%) | 4.2 (96%) |
| 3 | CD-RAP in 20 mM Histidine buffer, pH 6.5, 200 mM arginine | 1.8 | 1.0 (56%) | 1.7 (94%) | 40.1 | 45.5 | 37.7 | 4.6 | 2.3 (50%) | 4.4 (96%) |
| 4 | CD-RAP in 20 mM sodium phosphate, pH 7.4, 85 mM arginine/85 mM glutamic acid + 35 Mm glutamic acid | 1.6 | 0.3 (19%) | 1.4 (88%) | 38.2 | 41.4 | 36.4 | 4.1 | 0.8 (20%) | 3.8 (93%) |
| 5 | CD-RAP in 20 mM sodium phosphate, pH 7.4, 200 mM arginine and 45 mg/ml sucrose | 1.7 | 0.4 (24%) | 1.5 (88%) | 39.3 | 11.6 | 37.9 | 4.3 | 3.1 (72%) | 4.1 (95%) |

*Numbers in bracket represent CD-RAP recovery vs. T=0 calculated as [amount CD-RAP after stress / amount CD-RAP at T=0] *100

Fig. 12

| Formulation/ batch number | Description | pH after 3rd washing | pH after adjustment | Adjusted with |
|---|---|---|---|---|
| F531-03-003P018-0a (FHNA-120045) | CD-RAP reference formulation round 2 in 50 mM sodium phosphate, pH 7.4, 350 mM Arginine | NA | NA | NA |
| F531-03-003P0181-0b | Processed DS in in 50 mM sodium phosphate, pH 7.4, 350 mM arginine | 7.41 | NA | Not adjusted |
| F531-03-003P018-1 | CD-RAP in 50 mM potassium phosphate, pH 6.5, 200 mM arginine | 6.60 | 6.51 | HCl 1N |
| F531-03-003P018-2 | CD-RAP in 50 mM potassium phosphate, pH 6.5, 200 mM arginine, 2.08 mM ascorbic acid | 6.63 | 6.51 | HCl 1N |
| F531-03-003P018-3 | CD-RAP in 50 mM citrate, pH 6.5, 200 mM arginine | 6.74 | 6.53 | HCl 0.25N |
| F531-03-003P018-4 | CD-RAP in 50 mM citrate, pH 6.5, 200 mM arginine, 2.08 mM ascorbic acid | 6.86 | 6.54 | HCl 0.25N |
| F531-03-003P018-5 | CD-RAP in 50 mM histidine, pH 6.5, 200 mM Arginine | 6.63 | 6.52 | HCl 0.5N |
| F531-03-003P018-6 | CD-RAP in 50 mM histidine, pH 6.5, 200 mM arginine, 2.08 mM ascorbic acid | 6.51 | NA | Not adjusted |

Fig. 13

| Formulation/batch number | Description | pH formulations | Osmolality (mOsm/kg) |
|---|---|---|---|
| F531-03-003P011-0a (FHNA-120045) | CD-RAP reference formulation round 2 in 50 mM sodium phosphate, pH 7.4, 350 mM arginine | 7.2 | 401 |
| F531-03-003P011-0b | Processed DS in in 50 mM sodium phosphate, pH 7.4, 350 mM arginine | 7.3 | 405 |
| F531-03-003P018-1 | CD-RAP in 50 mM potassium phosphate, pH 6.5, 200 mM arginine | 6.5 | 352 |
| F531-03-003P018-2 | CD-RAP in 50 mM potassium phosphate, pH 6.5, 200 mM arginine, 2.08 mM ascorbic acid | 6.5 | 349 |
| F531-03-003P018-3 | CD-RAP in 50 mM citrate, pH 6.5, 200 mM arginine | 6.5 | 500 |
| F531-03-003P018-4 | CD-RAP in 50 mM citrate, pH 6.5, 200 mM arginine, 2.08 mM ascorbic acid | 6.6 | 511 |
| F531-03-003P018-5 | CD-RAP in 50 mM histidine, pH 6.5, 200 mM arginine | 6.5 | 434 |
| F531-03-003P018-6 | CD-RAP in 50 mM histidine, pH 6.5, 200 mM arginine, 2.08 mM ascorbic acid | 6.6 | 418 |

Fig. 14

| Form. | Description | T=0 | | T=2d/40°C | | 5 F/T cycles | |
| --- | --- | --- | --- | --- | --- | --- | --- |
| | | Clarity | Color | Clarity | Color | Clarity | Color |
| 0a | CD-RAP reference formulation round 2 in 50 mM sodium phosphate, pH 7.4, 350 mM arginine | clear | colorless | Turbid (~1000 NTU) | white suspension | clear | colorless |
| 0b | Processed DS in 50 mM sodium phosphate, pH 7.4, 350 mM arginine | clear | colorless | Turbid (200-1000 NTU) | white suspension | clear | colorless |
| 1 | CD-RAP in 50 mM potassium phosphate, pH 6.5, 200 mM arginine | clear | colorless | Turbid (200-1000 NTU) | white suspension | clear | colorless |
| 2 | CD-RAP in 50 mM potassium phosphate, pH 6.5, 200 mM arginine, 2.08 mM ascorbic acid | clear | colorless | Turbid (200-1000 NTU) | White to yellow suspension | clear | colorless |
| 3 | CD-RAP in 50 mM citrate, pH 6.5, 200 mM arginine | clear | colorless | Turbid (200-1000 NTU) | white suspension | clear | colorless |
| 4 | CD-RAP in 50 mM citrate, pH 6.5, 200 mM arginine, 2.08 mM ascorbic acid | clear | colorless | Turbid (200-1000 NTU) | White to yellow suspension | clear | colorless |
| 5 | CD-RAP in 50 mM histidine, pH 6.5, 200 mM arginine | clear | colorless | Turbid (200-1000 NTU) | white suspension | clear | colorless |
| 6 | CD-RAP in 50 mM histidine, pH 6.5, 200 mM arginine, 2.08 mM ascorbic acid | clear | slightly pink | Turbid (~1000 NTU) | Yellow-grey suspension | clear | slightly pink |

Fig. 15

| Form. | Description | Amount CD-RAP (mg/ml) | | | Area CD-RAP (%) | | | Total protein content (mg/ml) | | |
|---|---|---|---|---|---|---|---|---|---|---|
| | | t=0 | T=2d/ 40°C* | 5 F/T cycles* | t=0 | T=2d/ 40°C | 5 F/T cycles | t=0 | T=2d/ 40°C* | 5 F/T cycles* |
| 0a | CD-RAP reference formulation round 2 in 50 mM sodium phosphate, pH 7.4, 350 mM arginine | 7.7 | 6.2 (80%) | 7.6 (98%) | 79.8 | 78.1 | 79.5 | 9.6 | 7.9 (82%) | 9.5 (99%) |
| 0b | Processed DS in 50 mM sodium phosphate, pH 7.4, 350 mM arginine | 3.6 | 2.6 (73%) | 3.9 (108%) | 79.1 | 76.6 | 79.5 | 4.5 | 3.4 (75%) | 4.9 (108%) |
| 1 | CD-RAP in 50 mM potassium phosphate, pH 6.5, 200 mM arginine | 6.9 | 5.1 (74%) | 5.4 (78.8%) | 80.2 | 78.3 | 79.1 | 8.6 | 6.4 (75%) | 6.8 (80%) |
| 2 | CD-RAP in 50 mM potassium phosphate, pH 6.5, 200 mM arginine, 2.08 mM ascorbic acid | 4.6 | 3.0 (64%) | 4.4 (94%) | 78.6 | 59.4 | 76.5 | 5.9 | 5.0 (85%) | 5.7 (97%) |
| 3 | CD-RAP in 50 mM citrate, pH 6.5, 200 mM arginine | 5.4 | 5.2 (96%) | 5.2 (98%) | 79.9 | 78.7 | 79.2 | 6.7 | 6.6 (97%) | 6.6 (99%) |
| 4 | CD-RAP in 50 mM citrate, pH 6.5, 200 mM arginine, 2.08 mM ascorbic acid | 7.5 | 3.5 (47%) | 6.6 (89%) | 76.5 | 45.5 | 73.1 | 9.7 | 7.7 (79%) | 9.1 (93%) |
| 5 | CD-RAP in 50 mM histidine, pH 6.5, 200 mM arginine | 5.9 | 4.4 (76%) | 5.9 (101%) | 80.3 | 79.2 | 79.9 | 7.3 | 5.6 (77%) | 7.4 (102%) |
| 6 | CD-RAP in 50 mM histidine, pH 6.5, 200 mM arginine, 2.08 mM ascorbic acid | 8.1 | 3.5 (43%) | 5.7 (70%) | 72.4 | 60.2 | 68.3 | 11.2 | 5.8 (52%) | 8.3 (74%) |

*Numbers in bracket represent CD-RAP recovery vs. T=0 calculated as [amount CD-RAP after stress / amount CD-RAP at T=0] *100

Fig. 16

| Methods | | | Results | | | | | | | | |
|---|---|---|---|---|---|---|---|---|---|---|---|
| Parameters | | | Visual inspection | | | pH | Osmolality | SDS-PAGE non reduced | | SDS-PAGE reduced | | Microbiology |
| | | | Clarity | Color | Visible particles | pH | Osmolality (mOsm/kg) | MW main band (kDa) | Purity main band (%) | MW main band (kDa) | Purity main band (%) | TVAC |
| Time point (month) | Storage temp. (°C) | | | | | | | | | | | |
| 0 | NA | | < Ref 1 | Not more colored than B9/BY7/Y7 | Practically free of visible particles | 6.1 | 319 | 8 | 100 | 8 | 100 | < 1 CFU/5 ml |
| 1 | -80 | | | | | | | | | | | |
| | -20 | | < Ref 1 | Not more colored than B9/BY7/Y7 | Practically free of visible particles[a] | 6.1 | | 7[d] | 100 | 7[d] | 97 | |
| | 5 | | < Ref 1 | Not more colored than B9/BY7/Y7 | Practically free of visible particles | 6.1 | | 7[d] | 100 | 7[d] | 97 | |
| | 25 | | < Ref 1 | Not more colored than B9/BY7/Y7 | Practically free of visible particles | 6.1 | | 7[d] | 100 | 7[d] | 98 | |
| | 40 | | < Ref 1 | Not more colored than B9/BY7/Y7 | > 10 white fibre like particles[b] | 6.1 | | 7[d] | 100 | 7[d] | 96 | |
| 3 | -80 | | | | | | | | | | | |
| | -20 | | < Ref 1 | Not more colored than B9/BY7/Y7 | Practically free of visible particles (> 5 white fibre like particles but < 10) | 6.0 | | 8 | 100 | 10 | 98 | |
| | 5 | | < Ref 1 | Not more colored than B9/BY7/Y7 | Practically free of visible particles (> 5 white fibre like particles but < 10 and one black fibre in one vial) | 6.0 | | 8 | 100 | 10 | 98 | |
| | 25 | | < Ref 1 | Not more colored than B9/BY7/Y7 | > 20 fibre like particles[c] | 6.0 | | 8 | 100 | 10 | 98 | |
| | 40 | | | | | | | | | | | |
| 6 | -80 | | < Ref 1 | Not more colored than B9/BY7/Y7 | > 20 white fibre like particles but < 30 and two brown fibre in one vial | 6.1 | 315 | 8 | 100 | 7 | 100 | |
| | -20 | | < Ref 1 | Not more colored than B9/BY7/Y7 | Practically free of visible particles (> 5 white fibre like particles but < 10) | 6.1 | 318 | 8 | 100 | 7 | 100 | |
| | 5 | | < Ref 1 | Not more colored than B9/BY7/Y7 | Practically free of visible particles (> 5 white fibre like particles but < 10 and one brown fibre in one vial) | 6.1 | 319 | 8 | 100 | 8 | 100 | |
| | 25 | | < Ref 1 | Not more colored than B9/BY7/Y7 | > 10 white fibre like particles but < 20 and 1 brown and white/grey fibre in 1 vial and 1 white/grey fibre in the other vial | 6.1 | 317 | 8 | 100 | 9 | 100 | |
| | 40 | | | | | | | | | | | |

[a] One vial showed one grey fibre. [b] One to two big white 2-3 mm fibres and approximately 20 small particles were observed in both vials. [c] One big grey fibre and several white small particles were observed in both vials. [d] The MW was reported as for information purpose only in both non reduced and reduced SDS-PAGE results due to the "smiley" effect on the gel. This made it very difficult to determine the MW properly.

Fig. 16 continued

| Methods | | HPSEC | | | | Results | | | | |
|---|---|---|---|---|---|---|---|---|---|---|
| | | | | | | | | RP- | | |
| Parameters | | Aggregates (%) | CD-RAP content "as is" (mg/ml) | CD-RAP purity (%) | CD-RAP content total (mg/ml) | Impurity Ox-Met-SAR396049 | | Largest impurity besides Ox-Met-SAR396049 | | |
| | Storage temp. (°C) | | | | | RRT | Area% (%) | RRT | Area% (%) | |
| Time point (month) | | | | | | | | | | |
| 0 | NA | Not detected | 2 | 85.0 | 2. | 0.8 | 6.6 | 1.12 | 1.5 | |
| 1 | -80 | | | | | | | | | |
| | -20 | Not detected | 2 | 84.9 | 2. | 0.8 | 7.0 | 1.11 | 2.0 | |
| | 5 | Not detected | 2 | 84.8 | 2. | 0.8 | 7.1 | 1.11 | 1.9 | |
| | 25 | Not detected | 2 | 84.3 | 2. | 0.8 | 7.4 | 1.11 | 1.9 | |
| | 40 | Not detected | 2 | 81.6 | 2. | 0.8 | 9.1 | 1.11 | 2.0 | |
| 3 | -80 | | | | | | | | | |
| | -20 | Not detected | 2 | 84.2 | 2. | 0.8 | 7.0 | 1.10 | 1.7 | |
| | 5 | Not detected | 2 | 84.0 | 2. | 0.8 | 7.2 | 1.10 | 1.7 | |
| | 25 | Not detected | 1 | 81.9 | 2. | 0.8 | 8.2 | 1.10 | 1.7 | |
| | 40 | | | | | | | | | |
| 6 | -80 | Not detected | 2 | 84.1 | 2. | 0.8 | 7.0 | 1.12 | 1.9 | |
| | -20 | Not detected | 2 | 83.9 | 2. | 0.8 | 7.2 | 1.12 | 1.9 | |
| | 5 | Not detected | 2 | 83.5 | 2. | 0.8 | 7.5 | 1.12 | 1.9 | |
| | 25 | Not detected | 1 | 80.0 | 2. | 0.8 | 8.9 | 0.97 | 2.8 | |
| | 40 | | | | | | | | | |

Fig. 17

| Methods | | Visual inspection | | | pH | Osmolality | Results RP-HPLC | | HPSEC | SDS-PAGE | | Microbiology |
|---|---|---|---|---|---|---|---|---|---|---|---|---|
| Parameters | | Clarity | Color | Visible particles | pH | Osmolality (mOsm/kg) | CD-RAP Content (mg/ml) | CD-RAP purity (mg/ml) | Aggregates (%) | Main band MW (kDa) | Main band Purity (%) | TVAC |
| Time point (month) | Storage temp. (°C) | | | | | | | | | | | |
| 0 | NA | < Ref I | Not more colored than B9/BY7/Y7 | Practically free of visible particles | 6.1 | 313 | Not detected | Not detected | Not detected | No band detected | | < 1 CFU/5 ml |
| 1 | -80 | | | | | | | | | | | |
| | -20 | < Ref I | Not more colored than B9/BY7/Y7 | Practically free of visible particles | 6.1 | | Not detected | Not detected | Not detected | No band detected | | |
| | 5 | < Ref I | Not more colored than B9/BY7/Y7 | Practically free of visible particles | 6.0 | | Not detected | Not detected | Not detected | No band detected | | |
| | 25 | < Ref I | Not more colored than B9/BY7/Y7 | Practically free of visible particles [a] | 6.0 | | Not detected | Not detected | Not detected | No band detected | | |
| | 40 | < Ref I | Not more colored than B9/BY7/Y7 | Practically free of visible particles | 6.1 | | Not detected | Not detected | Not detected | No band detected | | |
| 3 | -80 | | | | | | | | | | | |
| | -20 | < Ref I | Not more colored than B9/BY7/Y7 | Practically free of visible particles | 6.0 | | Not detected | Not detected | Not detected | No band detected | | |
| | 5 | < Ref I | Not more colored than B9/BY7/Y7 | Practically free of visible particles [b] | 6.0 | | Not detected | Not detected | Not detected | No band detected | | |
| | 25 | < Ref I | Not more colored than B9/BY7/Y7 | Practically free of visible particles | 6.0 | | Not detected | Not detected | Not detected | No band detected | | |
| | 40 | | | | | | | | | | | |
| 6 | -80 | < Ref I | Not more colored than B9/BY7/Y7 | Practically free of visible particles [c] | 6.1 | 310 | Not detected | Not detected | Not detected | No band detected | | |
| | -20 | < Ref I | Not more colored than B9/BY7/Y7 | Practically free of visible particles | 6.0 | 310 | Not detected | Not detected | Not detected | No band detected | | |
| | 5 | < Ref I | Not more colored than B9/BY7/Y7 | Practically free of visible particles | 6.1 | 311 | Not detected | Not detected | Not detected | No band detected | | |
| | 25 | < Ref I | Not more colored than B9/BY7/Y7 | Practically free of visible particles | 6.1 | 309 | Not detected | Not detected | Not detected | No band detected | | |

Fig. 18
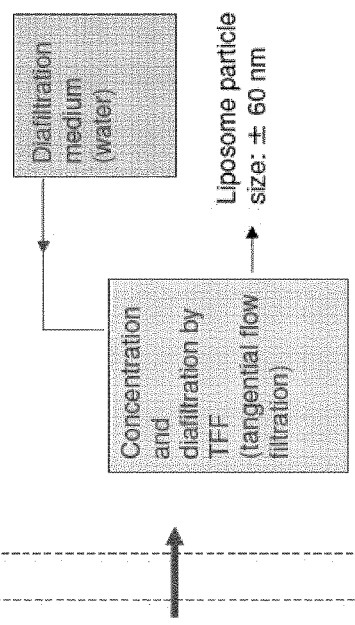
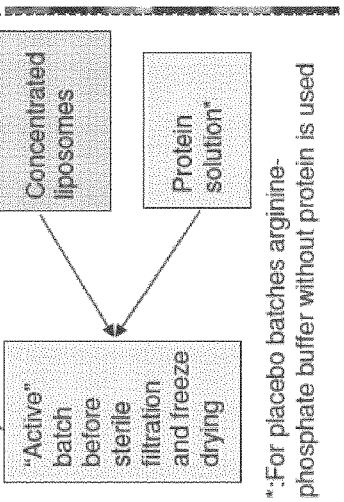
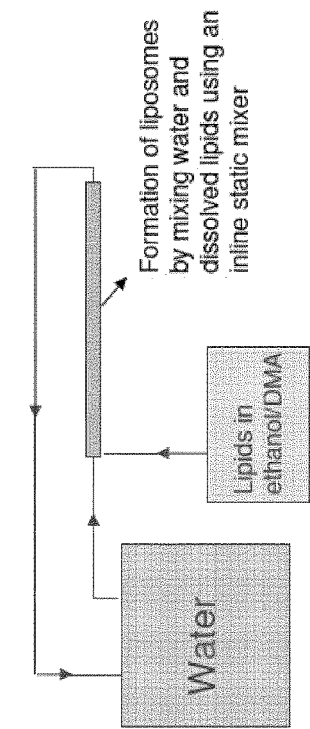
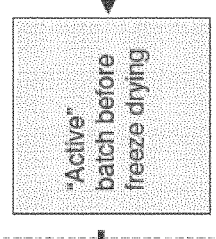
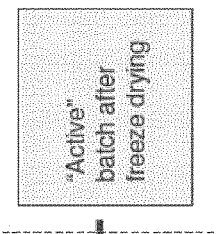
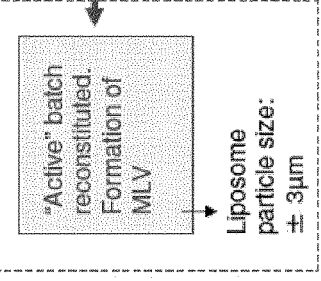

Fig. 19

| Lipid + solvent | Solubility (mg/ml) |
|---|---|
| Soy PC + ethanol | 1185 |
| Soy PC + TBA (95%) | 661 |
| Ascorbyl palmitate + ethanol | 75 |
| Ascorbyl palmitate + TBA | 94 |
| Cholesterol + Acetone | 46 |
| Cholesterol + DMSO | 47 |
| Cholesterol + DMA | 196 |

Fig. 20

| | Batch code | | |
|---|---|---|---|
| | F531-03-004p008E | F531-03-004p020C | F531-03-004p008E |
| Aqueous phase (ml/min) | 550 | 550 | 550 |
| Static mixer ID | Small | Small | Small |
| Lipid phase (ml/min) | 1 | 1 | 1 |
| Total lipid concentration (g/ml) | 0.329 | 0.061 | 0.033 |
| Concentration factor | 2 | 15 | 30 |
| Z-Ave (nm) | 1400 | 165 | 113 |
| PDI | 0.765 | 0.275 | 0.167 |

Fig. 21

|  | F531-03-004p020C | F531-03-004p025C |
|---|---|---|
| Aqueous phase (ml/min) | 550 | 550 |
| Static mixer ID | Small | Large |
| Lipid phase (ml/min) | 1 | 1 |
| Lipid concentration (g/ml) | 0.061 | 0.066 |
| Concentration factor | 15 | 15 |
| Z-Ave (nm) | 165 | 147 |
| PDI | 0.275 | 0.213 |

Fig. 22

| | F531-03-004p025C | F531-03-004p025D |
|---|---|---|
| Aqueous phase (ml/min) | 550 | 1100 |
| Static mixer ID | Large | Large |
| Lipid phase (ml/min) | 1 | 1 |
| Lipid in organic phase (g/ml) | 0.066 | 0.066 |
| Conc. factor to target volume | 15x | 15x |
| Z-Ave (nm) | 147 | 106 |
| PDI | 0.213 | 0.193 |

Fig. 23

|  | F531-03-004p038 |
|---|---|
| Aqueous phase (ml/min) | 1100 |
| Static mixer ID | Large |
| Lipid phase (ml/min) | 1 |
| Lipid in organic phase (g/ml) | 0.033 |
| Conc. factor to target volume | 30x |
| Z-Ave (nm) | 72 |
| PDI | 0.132 |

Fig. 24

| Sample Name | Z-Ave (nm) | PdI |
|---|---|---|
| F531-03-004p038F | 76.7 | 0.117 |
| F531-03-004p038G | 77.4 | 0.116 |

F531-03-004p038F: empty liposomes mixed with arginine phosphate buffer
F531-03-004p038G: empty liposomes mixed with protein solution (DS)

Fig. 25

A

Freezing steps

| Step | Temp / °C | Time / min |
|---|---|---|
| 1 | 5.0 | 1 |
| 2 | 5.0 | 60 |
| 3 | -45.0 | 30 |
| 4 | -45.0 | 120 |
| 5 | 0.0 | 0 |
| 6 | 0.0 | 0 |
| 7 | 0.0 | 0 |
| 8 | 0.0 | 0 |
| 9 | 0.0 | 0 |
| 10 | full cooling | |

FT Product / °C: -35.0

Drying steps

| Step | Temp / °C | Pressure / mbar | Time / min |
|---|---|---|---|
| 1 | -45.0 | 0.056 | 30 |
| 2 | 5.0 | 0.056 | 1 |
| 3 | 5.0 | 0.056 | 999 |
| 4 | 5.0 | 0.056 | 321 |
| 5 | 25.0 | 0.056 | 240 |
| 6 | 0.0 | 0.000 | 0 |
| 7 | 0.0 | 0.000 | 0 |
| 8 | 0.0 | 0.000 | 0 |
| 9 | 0.0 | 0.000 | 0 |
| 10 | 0.0 | 0.000 | 0 |

Past drying steps

| Step | Temp / °C | Pressure / mbar | Time / min |
|---|---|---|---|
| 1 | 25.0 | 0.056 | 300 |
| 2 | 5.0 | 0.056 | 1 |
| 3 | 5.0 | 0.056 | 999 |
| 4 | 5.0 | 0.056 | 681 |
| 5 | 0.0 | 0.000 | 0 |
| 6 | 0.0 | 0.000 | 0 |
| 7 | 0.0 | 0.000 | 0 |
| 8 | 0.0 | 0.000 | 0 |
| 9 | 0.0 | 0.000 | 0 |
| 10 | 0.0 | 0.000 | 0 |

B

Freezing steps

| Step | Temp / °C | Time / min |
|---|---|---|
| 1 | 5.0 | 1 |
| 2 | 5.0 | 60 |
| 3 | -45.0 | 30 |
| 4 | -45.0 | 120 |
| 5 | 0.0 | 0 |
| 6 | 0.0 | 0 |
| 7 | 0.0 | 0 |
| 8 | 0.0 | 0 |
| 9 | 0.0 | 0 |
| 10 | full cooling | |

FT Product / °C: -35.0

Drying steps

| Step | Temp / °C | Pressure / mbar | Time / min |
|---|---|---|---|
| 1 | -45.0 | 0.056 | 30 |
| 2 | -10.0 | 0.056 | 1 |
| 3 | -10.0 | 0.056 | 999 |
| 4 | -10.0 | 0.056 | 321 |
| 5 | 25.0 | 0.056 | 240 |
| 6 | 0.0 | 0.000 | 0 |
| 7 | 0.0 | 0.000 | 0 |
| 8 | 0.0 | 0.000 | 0 |
| 9 | 0.0 | 0.000 | 0 |
| 10 | 0.0 | 0.000 | 0 |

Past drying steps

| Step | Temp / °C | Pressure / mbar | Time / min |
|---|---|---|---|
| 1 | 25.0 | 0.056 | 300 |
| 2 | 5.0 | 0.056 | 1 |
| 3 | 5.0 | 0.056 | 999 |
| 4 | 5.0 | 0.056 | 681 |
| 5 | 0.0 | 0.000 | 0 |
| 6 | 0.0 | 0.000 | 0 |
| 7 | 0.0 | 0.000 | 0 |
| 8 | 0.0 | 0.000 | 0 |
| 9 | 0.0 | 0.000 | 0 |
| 10 | 0.0 | 0.000 | 0 |

Fig. 26

| Formulation code | Lipid content | Freeze-drying | Annealing (Y/N) | Product type | Reconstitution method | EE% (RP-HPLC) | Parameter |
|---|---|---|---|---|---|---|---|
| F531-03-008p033E | Standard | Christ | N | DP | Step-by-step | 20 | Reproducibility test |
| F531-03-008p033E | Standard | Christ | N | DP | Step-by-step | 17 | |
| F531-03-008p033E | Standard | Christ | N | DP | Step-by-step | 20 | |
| F531-03-008p031C | Standard | Controlled | Y | DP | Step-by-step | 29 | Effect of freeze-drying |
| F531-03-008P027K | 2X, double fill* | Christ | N | DP | Step-by-step | 41 | Effect of lipid content |
| F531-03-008p027F | 2X, concentrated** | Christ | N | DP | Step-by-step | 41 | |
| F531-03-008p027H | Standard, half protein | Christ | N | DP | Step-by-step | 27 | |
| F531-03-008p031A | 2X, concentrated** | Controlled | Y | DP | Step-by-step | 32 | Effect of annealing |
| F531-03-008p033E | Standard | Christ | N | DP | One step | 29 | Effect of reconstitution method and lipid content |
| F531-03-008p033E | Standard | Christ | N | DP | One step | 30 | |
| F531-03-008p033A | 2X, concentrated** | Christ | N | DP | One step | 43 | |
| F531-03-008p033A | 2X, concentrated** | Christ | N | DP | One step | 53 | |

*Prepared by filling the double volume of liposome suspension in the vial and reconstituting in the standard reconstitution volume
**Prepared by filling the standard volume of liposome suspension with twice the standard lipid concentration and reconstituting in the standard reconstitution volume

Fig. 27

A

| Formulation code | Lipid content | Freeze-drying | Annealing (Y/N) | Product type | Reconstitution method | EE% (RP-HPLC) |
|---|---|---|---|---|---|---|
| F531-03-008p033E | Standard | Christ | N | DP | Step-by-step | 20 |
| F531-03-008p033E | Standard | Christ | N | DP | Step-by-step | 17 |
| F531-03-008p033E | Standard | Christ | N | DP | Step-by-step | 20 |
| F531-03-008P027K | 2X, double fill | Christ | N | DP | Step-by-step | 41 |
| F531-03-008p027F | 2X, concentrated | Christ | N | DP | Step-by-step | 41 |
| F531-03-008p027H | Standard, half protein | Christ | N | DP | Step-by-step | 27 |

B

| Formulation code | Lipid content | Freeze-drying | Annealing (Y/N) | Product type | Reconstitution method | EE% (RP-HPLC) |
|---|---|---|---|---|---|---|
| F531-03-008p033E | Standard | Christ | N | DP | One step | 29 |
| F531-03-008p033E | Standard | Christ | N | DP | One step | 30 |
| F531-03-008p033A | 2X, concentrated | Christ | N | DP | One step | 43 |
| F531-03-008p033A | 2X, concentrated | Christ | N | DP | One step | 53 |

Fig. 28

A

| Formulation code | Lipid content | Freeze-drying | Annealing (Y/N) | Product type | Reconstitution method | EE% (RP-HPLC) |
|---|---|---|---|---|---|---|
| F531-03-008p033E | Standard | Christ | N | DP | Step-by-step | 20 |
| F531-03-008p033E | Standard | Christ | N | DP | Step-by-step | 17 |
| F531-03-008p033E | Standard | Christ | N | DP | Step-by-step | 20 |
| F531-03-008p031C | Standard | Controlled | Y | DP | Step-by-step | 29 |
| F531-03-008P027K | 2X, double fill | Christ | N | DP | Step-by-step | 41 |
| F531-03-008p027F | 2X, concentrated | Christ | N | DP | Step-by-step | 41 |
| F531-03-008p031A | 2X, concentrated | Controlled | Y | DP | Step-by-step | 32 |

B

| Formulation code | Lipid content | Freeze-drying | Annealing (Y/N) | Product type | Reconstitution method | EE% (RP-HPLC) |
|---|---|---|---|---|---|---|
| F531-03-008p033E | Standard | Christ | N | DP | Step-by-step | 20 |
| F531-03-008p033E | Standard | Christ | N | DP | Step-by-step | 17 |
| F531-03-008p033E | Standard | Christ | N | DP | Step-by-step | 20 |
| F531-03-008p033E | Standard | Christ | N | DP | One step | 29 |
| F531-03-008p033E | Standard | Christ | N | DP | One step | 30 |
| F531-03-008P027K | 2X, double fill | Christ | N | DP | Step-by-step | 41 |
| F531-03-008p027F | 2X, concentrated | Christ | N | DP | Step-by-step | 41 |
| F531-03-008p033A | 2X, concentrated | Christ | N | DP | One step | 43 |
| F531-03-008p033A | 2X, concentrated | Christ | N | DP | One step | 53 |

Fig. 29

| Formulation code | Lipid content* | Fill Volume (ml) | Vial size (ml) | recon. Volume (ml) | Freeze-drying | Buffer type | Rest period after | EE% RP-HPLC | Avearge EE% RP- | RSD% or Diff% (%) |
|---|---|---|---|---|---|---|---|---|---|---|
| F531-03- | 2x conc. Lipids | 3 | 10 | 1,64 | Christ | Phosphate | 1hr | 40 | 39 | 8% |
| F531-03- | 2x conc. Lipids | 3 | 10 | 1,64 | Christ | Phosphate | 1hr | 37 | | |
| F531-03- | 2x conc. Lipids | 3 | 10 | 1,64 | Christ | Phosphate | no incubation | 38 | 42 | 19% |
| F531-03- | 2x conc. Lipids | 3 | 10 | 1,64 | Christ | Phosphate | no incubation | 46 | | |
| F531-03- | 2x conc. Lipids | 3 | 10 | 1,64 | Controlled | Phosphate | 1hr | 37 | 41 | 20% |
| F531-03- | 2x conc. Lipids | 3 | 10 | 1,64 | Controlled | Phosphate | 1hr | 45 | | |
| F531-03- | 2x conc. Lipids | 3 | 10 | 1,64 | Controlled | Phosphate | no incubation | 45 | 48 | 11% |
| F531-03- | 2x conc. Lipids | 3 | 10 | 1,64 | Controlled | Phosphate | no incubation | 50 | | |
| F531-03- | 2x conc. Lipids | 1,8 | 6 | 1 | Controlled | Phosphate | no incubation | 47 | 45 | 9% |
| F531-03- | 2x conc. Lipids | 1,8 | 6 | 1 | Controlled | Phosphate | no incubation | 43 | | |
| F531-03- | 2x conc. Lipids | 1,8 | 3 | 1 | Controlled | Phosphate | no incubation | 48 | 46 | 6% |
| F531-03- | 2x conc. Lipids | 1,8 | 3 | 1 | Controlled | Phosphate | no incubation | 46 | | |
| F531-03- | 2x conc. Lipids | 1,8 | 3 | 1 | Controlled | Phosphate | no incubation | 43 | | |
| F531-03-008p050A | 2x conc. Lipids | 1,8 | 3 | 1 | Controlled | Phosphate | no incubation | 36 | 40 | 8% |
| F531-03-008p050A | 2x conc. Lipids | 1,8 | 3 | 1 | Controlled | Phosphate | no incubation | 42 | | |
| F531-03-008p050A | 2x conc. Lipids | 1,8 | 3 | 1 | Controlled | Phosphate | no incubation | 41 | | |
| F531-03- | 2x conc. Lipids | 1,8 | 3 | 1 | Controlled | Citrate | no incubation | 45 | 43 | 8% |
| F531-03- | 2x conc. Lipids | 1,8 | 3 | 1 | Controlled | Citrate | no incubation | 39 | | |
| F531-03- | 2x conc. Lipids | 1,8 | 3 | 1 | Controlled | Citrate | no incubation | 46 | | |
| F531-03-008p050E | 3x conc. Lipids | 2,3 | 3 | 1 | Controlled | Phosphate | no incubation | 50 | 51 | 3% |
| F531-03-008p050E | 3x conc. Lipids | 2,3 | 3 | 1 | Controlled | Phosphate | no incubation | 52 | | |
| F531-03- | 3x conc. Lipids | 2,3 | 3 | 1 | Controlled | Citrate | no incubation | 39 | 40 | 2% |
| F531-03- | 3x conc. Lipids | 2,3 | 3 | 1 | Controlled | Citrate | no incubation | 40 | | |
| F531-03-008p050J | 4x conc. Lipids | 2,8 | 3 | 1 | Controlled | Phosphate | no incubation | 62 | 62 | 2% |
| F531-03-008p050J | 4x conc. Lipids | 2,8 | 3 | 1 | Controlled | Phosphate | no incubation | 61 | | |
| F531-03-008p050L | 4x conc. Lipids | 2,8 | 3 | 1 | Controlled | Citrate | no incubation | 50 | 51 | 3% |
| F531-03-008p050L | 4x conc. Lipids | 2,8 | 3 | 1 | Controlled | Citrate | no incubation | 51 | | |

Note: All formulations were prepared by filling a higher volume of liposome suspension in the vial and reconstituting in the standard reconstitution volume

Fig. 30

A

| Samples | Description | Vial | RSD% | Content As is based on cake volume correction | | |
|---|---|---|---|---|---|---|
| | | | | Expected content (mg/mL) | AVG EE (%) | AVG EE (%) |
| F531-03-008p056E_1 | 4x lipid | 2R | 3,50 | 3,2 | 23 | 24 |
| F531-03-008p056E_1 | | | | | | |
| F531-03-008p056E_2 | | | 1,20 | 3,2 | 25 | |
| F531-03-008p056E_2 | | | | | | |
| F531-03-008p056F_1 | 4x lipid | 6R | 7,10 | 3,2 | 23 | 21 |
| F531-03-008p056F_1 | | | | | | |
| F531-03-008p056F_2 | | | 7,97 | 3,2 | 19 | |
| F531-03-008p056F_2 | | | | | | |
| F531-03-008p056J_1 | 6x lipid | 6R | 10,15 | 2,7 | 29 | 31 |
| F531-03-008p056J_1 | | | | | | |
| F531-03-008p056J_2 | | | 5,72 | 2,7 | 33 | |
| F531-03-008p056J_2 | | | | | | |

B

| Samples | Description | Vial | Freezing type | Content as is based on cake volume | | |
|---|---|---|---|---|---|---|
| | | | | Expected content (mg/mL) | EE (%) | AVG EE (%) |
| F531-03-008P064E1_1 | 4x lipid | 6R | slow | 3,3 | 26 | 22 |
| F531-03-008P064E1_2 | | | slow | | 18 | |
| F531-03-008P064E2_1 | | | fast | 3,1 | 22 | 19 |
| F531-03-008P064E2_2 | | | fast | | 16 | |
| F531-03-008P064F1_1 | 6x lipid | 6R | slow | 2,9 | 21 | 27 |
| F531-03-008P064F1_2 | | | slow | | 32 | |
| F531-03-008P064F2_1 | | | fast | 2,9 | 26 | 27 |
| F531-03-008P064F2_2 | | | fast | | 29 | |

Fig. 31

| Batch | Methods | | | | Results | | | | | | | | | | |
|---|---|---|---|---|---|---|---|---|---|---|---|---|---|---|---|
| | Parameters | | Visual inspection | | pH | Particle size after reconstitution (DLS) | | Particle size after reconstitution (laser diffraction) | | | | | Karl Fischer | Osmolality | Micro-biology |
| | Time point (month) | Storage temp. (°C) | Cake appearance | Appearance after reconstitution | pH | z-average (nm) | PdI | D(0.1) (mm) | D(0.5) (mm) | D(0.9) (mm) | D[4,3] (mm) | D[3,2] (mm) | Residual moisture (%) | Osmolality (mOsm/kg) | TVAC |
| F530-03-008P082K (Drug product) | 0 | NA | Off white cake | Homogeneous solution, no lumps observed | 6,2 | 2855 | 0,396 | 2,5 | 3,9 | 6,3 | 4,2 | 3,7 | 0,15 | 270 | <1 CFU/ 1 ml |
| | 1 | -80 | Off white cake | | | | | | | | | 3,5 | | | |
| | | -20 | Off white cake | Homogeneous solution, no | 6,2 | | | 2,4 | 3,7 | 5,9 | 4,0 | | | | |
| | | 5 | Off white cake | Homogeneous solution, no | 6,2 | | | 2,4 | 4,0 | 7,2 | 5,0 | 3,7 | | | |
| | | 25 | Off white cake | Homogeneous solution, 1 vial contained a lump, 1 vial was lump free | 6,2 | | | 2,3 | 3,8 | 6,2 | 4,1 | 3,5 | | | |
| | 3 | -80 | Off white cake | Homogeneous solution, no | 6,2 | | | 2,4 | 4,0 | 7,2 | 4,6 | 3,8 | 0,17 | | |
| | | -20 | Off white cake | Homogeneous solution, both | 6,2 | | | 2,4 | 3,8 | 6,0 | 4,0 | 3,6 | 0,18 | | |
| | | 5 | Off white cake | Homogeneous solution, 1 vial contained a lump, 1 vial was lump free | 6,2 | | | 2,5 | 3,9 | 6,3 | 4,2 | 3,7 | 0,23 | | |
| | | 25 | Off white cake | Homogeneous solution, both | 6,2 | | | 2,5 | 3,9 | 6,3 | 4,2 | 3,7 | 0,31 | | |

Fig. 31 continued

| Sample | Time | Temp | Appearance | Solution | 6.1 | 3641 | 0.423 | 2.6 | 4.3 | 7.1 | 4.7 | 4.0 | 0.11 | 253 | <1 CFU/5 ml |
|---|---|---|---|---|---|---|---|---|---|---|---|---|---|---|---|
| F530-03-008P082L (Placebo) | 0 | NA | Off white cake | Homogeneous solution, no lumps observed | | 3641 | 0,423 | 2,6 | 4,3 | 7,1 | 4,7 | 4,0 | 0,11 | 253 | |
| | 1 | -80 | Off white cake | | | | | | | | | | | | |
| | | -20 | Off white cake | Homogeneous solution, no | 6,1 | | | 2,5 | 4,0 | 6,4 | 7,6 | 3,8 | | | |
| | | 5 | Off white cake | Homogeneous solution, 1 vial contained a lump, 1 vial was lump free | 6,1 | | | 2,5 | 3,8 | 5,8 | 4,0 | 3,6 | | | |
| | | 25 | Off white cake | Homogeneous solution, both | 6,1 | | | 2,6 | 4,0 | 6,2 | 4,3 | 3,8 | 0,15 | | |
| | 3 | -80 | Off white cake | Homogeneous solution, no | 6,1 | | | 2,6 | 4,0 | 6,4 | 4,3 | 3,8 | | | |
| | | -20 | Off white cake | Homogeneous solution, no | 6,1 | | | 2,6 | 4,1 | 6,7 | 4,4 | 3,9 | 0,14 | | |
| | | 5 | Off white cake | Homogeneous solution, 1 vial contained a lump, 1 vial was lump free | 6,1 | | | 2,5 | 3,9 | 5,9 | 4,1 | 3,7 | 0,19 | | |
| | | 25 | Off white cake | Homogeneous solution, both | 6,1 | | | 2,7 | 4,4 | 7,1 | 4,7 | 4,1 | 0,28 | | |

SEQUENCE LISTING

```
<160> NUMBER OF SEQ ID NOS: 21

<210> SEQ ID NO 1
<211> LENGTH: 107
<212> TYPE: PRT
<213> ORGANISM: Homo sapiens

<400> SEQUENCE: 1

Gly Pro Met Pro Lys Leu Ala Asp Arg Lys Leu Cys Ala Asp Gln Glu
1               5                   10                  15

Cys Ser His Pro Ile Ser Met Ala Val Ala Leu Gln Asp Tyr Met Ala
            20                  25                  30

Pro Asp Cys Arg Phe Leu Thr Ile His Arg Gly Gln Val Val Tyr Val
        35                  40                  45

Phe Ser Lys Leu Lys Gly Arg Gly Arg Leu Phe Trp Gly Gly Ser Val
    50                  55                  60

Gln Gly Asp Tyr Tyr Gly Asp Leu Ala Ala Arg Leu Gly Tyr Phe Pro
65                  70                  75                  80

Ser Ser Ile Val Arg Glu Asp Gln Thr Leu Lys Pro Gly Lys Val Asp
                85                  90                  95

Val Lys Thr Asp Lys Trp Asp Phe Tyr Cys Gln
                100                 105

<210> SEQ ID NO 2
<211> LENGTH: 6
<212> TYPE: PRT
<213> ORGANISM: Artificial Sequence
<220> FEATURE:
<223> OTHER INFORMATION: pre-sequence

<400> SEQUENCE: 2

Met Ala Thr Thr Ser Thr
1               5
```

```
<210> SEQ ID NO 3
<211> LENGTH: 6
<212> TYPE: PRT
<213> ORGANISM: Artificial Sequence
<220> FEATURE:
<223> OTHER INFORMATION: pre-sequence

<400> SEQUENCE: 3

Met Ala Thr Thr Leu Thr
1               5

<210> SEQ ID NO 4
<211> LENGTH: 7
<212> TYPE: PRT
<213> ORGANISM: Artificial Sequence
<220> FEATURE:
<223> OTHER INFORMATION: pre-sequence

<400> SEQUENCE: 4

Met Ala Thr Thr Ser Thr Gly
1               5

<210> SEQ ID NO 5
<211> LENGTH: 7
<212> TYPE: PRT
<213> ORGANISM: Artificial Sequence
<220> FEATURE:
<223> OTHER INFORMATION: pre-sequence

<400> SEQUENCE: 5

Met Ala Thr Thr Leu Thr Gly
1               5

<210> SEQ ID NO 6
<211> LENGTH: 8
<212> TYPE: PRT
<213> ORGANISM: Artificial Sequence
<220> FEATURE:
<223> OTHER INFORMATION: pre-sequence

<400> SEQUENCE: 6

Met Ala Thr Thr Ser Thr Gly Asn
1               5

<210> SEQ ID NO 7
<211> LENGTH: 8
<212> TYPE: PRT
<213> ORGANISM: Artificial Sequence
<220> FEATURE:
<223> OTHER INFORMATION: pre-sequence

<400> SEQUENCE: 7

Met Ala Thr Thr Leu Thr Gly Asn
1               5

<210> SEQ ID NO 8
<211> LENGTH: 9
<212> TYPE: PRT
<213> ORGANISM: Artificial Sequence
<220> FEATURE:
<223> OTHER INFORMATION: pre-sequence

<400> SEQUENCE: 8

Met Ala Thr Thr Ser Thr Gly Asn Ser
1               5
```

```
<210> SEQ ID NO 9
<211> LENGTH: 9
<212> TYPE: PRT
<213> ORGANISM: Artificial Sequence
<220> FEATURE:
<223> OTHER INFORMATION: pre-sequence

<400> SEQUENCE: 9

Met Ala Thr Thr Leu Thr Gly Asn Ser
1               5

<210> SEQ ID NO 10
<211> LENGTH: 10
<212> TYPE: PRT
<213> ORGANISM: Artificial Sequence
<220> FEATURE:
<223> OTHER INFORMATION: pre-sequence

<400> SEQUENCE: 10

Met Ala Thr Thr Ser Thr Gly Asn Ser Ala
1               5                   10

<210> SEQ ID NO 11
<211> LENGTH: 10
<212> TYPE: PRT
<213> ORGANISM: Artificial Sequence
<220> FEATURE:
<223> OTHER INFORMATION: pre-sequence

<400> SEQUENCE: 11

Met Ala Thr Thr Leu Thr Gly Asn Ser Ala
1               5                   10

<210> SEQ ID NO 12
<211> LENGTH: 7
<212> TYPE: PRT
<213> ORGANISM: Artificial Sequence
<220> FEATURE:
<223> OTHER INFORMATION: pre-sequence

<400> SEQUENCE: 12

Met Ala Thr Thr Ser Thr Arg
1               5

<210> SEQ ID NO 13
<211> LENGTH: 7
<212> TYPE: PRT
<213> ORGANISM: Artificial Sequence
<220> FEATURE:
<223> OTHER INFORMATION: pre-sequence

<400> SEQUENCE: 13

Met Ala Thr Thr Leu Thr Arg
1               5

<210> SEQ ID NO 14
<211> LENGTH: 11
<212> TYPE: PRT
<213> ORGANISM: Artificial Sequence
<220> FEATURE:
<223> OTHER INFORMATION: pre-sequence

<400> SEQUENCE: 14

Met Ala Thr Thr Ser Thr Gly Asn Ser Ala Arg
1               5                   10
```

```
<210> SEQ ID NO 15
<211> LENGTH: 11
<212> TYPE: PRT
<213> ORGANISM: Artificial Sequence
<220> FEATURE:
<223> OTHER INFORMATION: pre-sequence

<400> SEQUENCE: 15

Met Ala Thr Thr Leu Thr Gly Asn Ser Ala Arg
1               5                   10

<210> SEQ ID NO 16
<211> LENGTH: 19
<212> TYPE: PRT
<213> ORGANISM: Artificial Sequence
<220> FEATURE:
<223> OTHER INFORMATION: pre-sequence

<400> SEQUENCE: 16

Met Ala Thr Thr Ser Thr Leu Thr Thr His Trp His Trp His Gly Asn
1               5                   10                  15

Ser Ala Arg

<210> SEQ ID NO 17
<211> LENGTH: 21
<212> TYPE: PRT
<213> ORGANISM: Artificial Sequence
<220> FEATURE:
<223> OTHER INFORMATION: pre-sequence

<400> SEQUENCE: 17

Met Ala Thr Thr Ser Thr Gly Asn Ser Ala His Phe Gln His His His
1               5                   10                  15

Gly Ser Leu Ala Arg
            20

<210> SEQ ID NO 18
<211> LENGTH: 21
<212> TYPE: PRT
<213> ORGANISM: Artificial Sequence
<220> FEATURE:
<223> OTHER INFORMATION: pre-sequence

<400> SEQUENCE: 18

Met Ala Thr Thr Ser Thr Gly Asn Ser Ala His Phe Gln His His His
1               5                   10                  15

Gly Ser Leu Ala Arg
            20

<210> SEQ ID NO 19
<211> LENGTH: 34
<212> TYPE: PRT
<213> ORGANISM: Artificial Sequence
<220> FEATURE:
<223> OTHER INFORMATION: pre-sequence

<400> SEQUENCE: 19

Met Ala Thr Thr Ser Thr Gly Asn Ser Ala Arg Phe Val Asn Gln His
1               5                   10                  15

Leu His His His His His His His His Gly Gly Gly Glu Asn Gln Gln
            20                  25                  30

Gln Arg
```

```
<210> SEQ ID NO 20
<211> LENGTH: 141
<212> TYPE: PRT
<213> ORGANISM: Artificial Sequence
<220> FEATURE:
<223> OTHER INFORMATION: CD-RAP precursor protein

<400> SEQUENCE: 20

Met Ala Thr Thr Ser Thr Gly Asn Ser Ala Arg Phe Val Asn Gln His
1               5                   10                  15

Leu His His His His His His His Gly Gly Gly Glu Asn Gln Gln
            20                  25                  30

Gln Arg Gly Pro Met Pro Lys Leu Ala Asp Arg Lys Leu Cys Ala Asp
        35                  40                  45

Gln Glu Cys Ser His Pro Ile Ser Met Ala Val Ala Leu Gln Asp Tyr
    50                  55                  60

Met Ala Pro Asp Cys Arg Phe Leu Thr Ile His Arg Gly Gln Val Val
65                  70                  75                  80

Tyr Val Phe Ser Lys Leu Lys Gly Arg Gly Arg Leu Phe Trp Gly Gly
                85                  90                  95

Ser Val Gln Gly Asp Tyr Tyr Gly Asp Leu Ala Ala Arg Leu Gly Tyr
            100                 105                 110

Phe Pro Ser Ser Ile Val Arg Glu Asp Gln Thr Leu Lys Pro Gly Lys
        115                 120                 125

Val Asp Val Lys Thr Asp Lys Trp Asp Phe Tyr Cys Gln
    130                 135                 140

<210> SEQ ID NO 21
<211> LENGTH: 105
<212> TYPE: PRT
<213> ORGANISM: Homo sapiens

<400> SEQUENCE: 21

Met Pro Lys Leu Ala Asp Arg Lys Leu Cys Ala Asp Gln Glu Cys Ser
1               5                   10                  15

His Pro Ile Ser Met Ala Val Ala Leu Gln Asp Tyr Met Ala Pro Asp
            20                  25                  30

Cys Arg Phe Leu Thr Ile His Arg Gly Gln Val Val Tyr Val Phe Ser
        35                  40                  45

Lys Leu Lys Gly Arg Gly Arg Leu Phe Trp Gly Gly Ser Val Gln Gly
    50                  55                  60

Asp Tyr Tyr Gly Asp Leu Ala Ala Arg Leu Gly Tyr Phe Pro Ser Ser
65                  70                  75                  80

Ile Val Arg Glu Asp Gln Thr Leu Lys Pro Gly Lys Val Asp Val Lys
                85                  90                  95

Thr Asp Lys Trp Asp Phe Tyr Cys Gln
            100                 105
```

EXPRESSION AND FOLDING IN THE MANUFACTURING PROCESS OF CD-RAP BY USING A CD-RAP PRECURSOR PROTEIN

The present invention relates to a CD-RAP precursor protein comprising a pre-sequence and CD-RAP, and its use in manufacturing of native CD-RAP. The present invention further relates to a composition comprising CD-RAP and at least one positively charged amino acid and a buffer, pharmaceuticals comprising said composition, their use in methods of treating and/or preventing cartilage disease or injury in patients suffering from aggrecan degradation, and/or increased influx of water into the cartilage, and/or decreased CD-RAP expression, as well as methods of producing said composition and methods of storing CD-RAP in said composition. The present invention further relates to a composition comprising liposomes comprising encapsulated CD-RAP or a variant thereof, its use in methods of treating joint disease or injury, and methods of producing such liposomal composition as well as storing CD-RAP therein.

BACKGROUND

Osteoarthritis (OA) is a highly prevalent degenerative joint disease, which develops very slowly. Hallmarks of OA are destruction of the joint cartilage (loss of proteoglycans and collagens from the cartilage matrix), accompanied with damage to the underlying bone formation of osteophytes (bony projections along joint margins) and changes in the synovial membrane, leading to joint inflammation (synovitis). Altogether, these processes cause pain, misalignment and loss of function of the affected joints. Osteoarthritis is characterized by loss of joint cartilage that leads to pain and loss of function, typically in the knees and hips, and affects 81.4 million individuals in seven major markets, which are the US, Japan, France, Germany, Italy and Spain (Datamonitor Report DMHC2493, December 2009). In the US, the Center for Disease Control and Prevention (CDC) reports that, overall OA affects 13.9% of adults aged 25 and older and 33.6% (12.4 million) of those 65+(an estimated 26.9 million US adults in 2005 up from 21 million in 1990). Increases in life expectancy and ageing populations are expected to make osteoarthritis the fourth leading cause of disability by the year 2020 (Anthony D. Woolf & Bruce Pfleger, Burden of major musculoskeletal conditions, Bulletin of the World Health Organization 2003; 81:646-656). From the medical perspective, OA is also associated with other chronic disorders such as over-weight, diabetes, hypertension, dyslipidemia and coronary artery disease, which account for the multi-morbidity of subjects diagnosed with OA.

Currently, at the exclusion of replacement surgery, there is no cure for OA and available treatments aim at relieving symptoms and improving function. These include a combination of patient education, physical therapy, weight control, and use of medications (nutritional supplements, simple analgesics, topical NSAIDS, oral NSAIDS, cox-2-inhibitors, and oral steroids, intra-articularly administered steroids and hyaluronic acid).

In the past several attempts were made to inhibit the activity of those enzymes mainly involved in the degradation of the cartilage. Unfortunately with little success so far. Anti protease treatments lacked the required potency and clinical benefit (Lewis E J, Bishop J, Bottomley K M, Bradshaw D, Brewster M, Broadhurst M J, et al. Ro 32-3555, an orally active collagenase inhibitor, prevents cartilage breakdown in vitro and in vivo. Br J Pharmacol 1997; 121:540-6; Brown P D. Ongoing trials with matrix metalloproteinase inhibitors. Expert Opin Investig Drugs 2000; 9:2167-77), were not sufficiently bioavailable or orally active and/or lacked specificity to the targeted enzymes. Specifically, MMP inhibitors showed dose- and duration-dependent muskuloskeletal side effects consisting of joint stiffness, joint fibroplasias and accumulation of collagen type I in the osteoarthritic joints (Renkiewicz R, Qiu L, Lesch C, Sun X, Devalaraja R, Cody T, et al. Broad-spectrum matrix metalloproteinase inhibitor marimastat-induced musculoskeletal side effects in rats. Arthritis Rheum 2003; 48:1742-9; Rao B G. Recent developments in the design of specific Matrix Metalloproteinase inhibitors aided by structural and computational studies. Curr Pharm Des 2005; 11:295-322). With the increasing number of patients suffering from the disease, novel therapeutics are highly desirable and much sought after which are less invasive, do not only relieve the symptoms but improve the underlying cause of the disease or injury, i.e. the degradation of the cartilage.

With the increasing number of patients suffering from the disease, novel therapeutics are highly desirable and much sought after which are less invasive, do not only relieve the symptoms but improve the underlying cause of the disease or injury, i.e. the degradation of the cartilage.

The therapeutic protein CD-RAP was shown to be able to slow the degradation of cartilage as well as to improve the regeneration of damaged cartilage. However, in order to serve as source for a sufficient drug supply, CD-RAP also needs to meet the commercial requirements of high yield in production. Thus, it is desirable to produce CD-RAP by recombiant DNA-technology. A recombinant bacterial process could solve the problem by expressing the gene encoding CD-RAP under control of a strong bacterial promoter. Bacterial direct expression requires a Methionin at position −1 for initiation of translation. The codon has to be added to the sequence encoding CD-RAP sequence. The native CD-RAP contains at Position 3 of its sequence a Methionin. During expression this Methionin could be also used for translational initiation. Thus two expression products would be observed, one starting with Glycin to give rise to native CD-RAP and one starting with Proline to give rise to a truncated form of CD-RAP. Analysis of hitherto available CD-RAP preparations revealed that these preparations, in fact, contain at least three different CD-RAP species. In particular, the amino terminus of CD-RAP, e.g. expressed in *E. coli*, is sensitive to degradation, resulting in an about 10% N-terminal heterogeneity of the CD-RAP product. CD-RAP obtained by expression in *E. coli* contains at least the following three different protein species:

a) CD-RAP (108AA) having an additional N-terminal methionine, i.e. in total 108 amino acids, which is the major species (?. 90%) and has the N-terminus: MGPMPKL . . .
b) CD-RAP (107AA) consisting of the mature CD-RAP sequence without an additional N-terminal methionine and having the N-terminus GPMPKL . . . as well as
c) CD-RAP (105AA) being an N-terminal truncated CD-RAP having the N-terminal sequence: MPKL . . . , i.e. two amino acids less than the mature CD-RAP sequence.

This heterogeneity in product is not desirable as further purification steps lowering yield would become necessary. The heterogeneity could become even higher if the F-methionin would not be quantitatively removed posttranslationally. Furthermore, native CD-RAP exhibits a high hydrophobicity, which results in a restricted expression in bacteria due it its relative toxicity for the cells.

The recombinant expression of CD-RAP further requires the folding of the protein subsequent to its expression. However, folding yields of native CD-RAP were found to be very low, partially due to the high hydrophobicity.

To overcome these problems in the production of CD-RAP, a fusion protein of CD-RAP with a pre-sequence was designed, which leads to high yield in expression of this precursor CD-RAP protein, which may, amongst others, be due to the reduced hydrophobicity of the precursor protein. Moreover, the folding of the fusion protein was found to be much easier than that of the native CD-RAP. To constitute the native CD-RAP after the folding it is however necessary to remove the pre-sequence by an enzymatic cleavage. To achieve this, the interface between the amino acid sequence of the native CD-RAP and the pre-sequence was designed as cleavage site, in particular as cleavage site for an endoprotease. Overall, the productivity of CD-RAP is increased after its expression with a pre-sequence and the subsequent removal of the pre-sequence, up to 60 fold compared to expression without pre-sequence. Preparation of CD-RAP using the CD-RAP precursor protein disclosed herein allows for the provision of a CD-RAP preparation having a defined length of 107 amino acids and having a defined N-terminus. This is an essential advantage in addition to improved yield at the manufacture of CD-RAP.

To specifically target effected joints and decrease possible (e.g. systemic) side effects, there is also a need for formulations allowing for intra-articular administration of CD-RAP.

In this context, formulations are desired which are suitable for intravenous and intra-articular administration. Desirably, these formulations comprise excipients and buffer combinations that leads to increased stabilisation of the CD-RAP protein allowing for longer storage of the formulation. In particular, formulations are desired which allow CD-RAP to remain at the effected side for a longer period of time and to reach chondrocytes more effectively. To allow therapeutic and/or preventive administration such formulation needs to be sterilisable as well as exhibit e long shelf-life allowing for its storage. Therefore, a liposomal formulation of CD-RAP was developed which is suitable for intra-articular administration. A scalable process was developed to produce empty liposomes small enough to be sterilized by filtration. Formulation development studies allowed identifying the parameters influencing CD-RAP encapsulation efficiency in the liposomal product, which were found to be the buffer type, and the lipid content, as well as the reconstitution method for a freeze-dried formulation.

The general process of producing liposomal formulations involves the following steps used are: —Preparation of empty liposomes (small unilamellar vesicles, SUVs) by preparing a lipid blend which is hydrated and homogenised, and liposomes are then extruded; —Mixing of SUV suspension with CD-RAP aqueous solution, —Freeze-drying, —Reconstitution with water for injection (WFI).

At the end of this process, the polydispersity of the liposomes is rather large (about 0.3), which leads to sterile filtration problems. In order to simplify the process and reduce polydispersity, a solvent injection method was developed to prepare the empty liposomes. In this method there is no need to produce a lipid blend, thereby avoiding the preparation of an intermediate product and eliminating a process step. Solvent injection is a scalable method which allows for a straightforward scale up as well as avoiding sizing steps such as homogenisation and extrusion.

SUMMARY OF THE INVENTION

In a first aspect, the present invention relates to a CD-RAP precursor protein comprising
a) a pre-sequence, which comprises at its C-terminus a cleavage site, and
b) CD-RAP or a variant thereof.

In a second aspect, the present invention relates to a nucleic acid encoding the precursor CD-RAP protein of the first aspect.

In a third aspect, the present invention relates to a vector comprising the nucleic acid of the second aspect.

In a fourth aspect, the present invention relates to a host cell comprising the precursor CD-RAP protein of the first aspect, the nucleic acid of the second aspect, or the vector of the third aspect.

In a fifth aspect, the present invention relates to a method of producing native CD-RAP comprising the steps
a) providing a CD-RAP precursor protein of the first aspect, and
b) removing the pre-sequence to obtain native CD-RAP.

In a sixth aspect, the present invention relates to a CD-RAP protein preparation comprising a CD-RAP protein having the mature CD-RAP sequence of SEQ ID NO: 1 with a length of 107 amino acids.

In a seventh aspect, the present invention relates to a composition comprising CD-RAP or a variant thereof, and at least one positively charged amino acid and a buffer.

In an eighth aspect, the present invention relates to the protein preparation of the sixth aspect, or the composition of the seventh aspect for use in a method of in treating and/or preventing cartilage disease or injury in patients suffering from aggrecan degradation, and/or increased influx of water into the cartilage, and/or decreased CD-RAP expression.

In a ninth aspect, the present invention relates to a pharmaceutical comprising the protein preparation of the sixth aspect, or the composition of the seventh aspect of the present invention.

In a tenth aspect, the present invention relates to a method of producing a composition of the seventh aspect of the present invention.

In a eleventh aspect, the present invention relates to a method of storing CD-RAP.

In an twelfths aspect, the present invention relates to a composition comprising liposomes comprising encapsulated CD-RAP (in particular according to SEQ ID NO: 1) or a variant thereof, wherein the size of the liposomes is below 200 nm.

In a thirteenth aspect, the present invention relates to the composition of the eleventh aspect for use in a method of in treating and/or preventing cartilage disease or injury in patients suffering from aggrecan degradation, and/or increased influx of water into the cartilage, and/or decreased CD-RAP expression.

In a fourteenth aspect, the present invention relates to pharmaceutical comprising the composition of the twelfths or thirteenth aspect.

In a fifteenth aspect, the present invention relates to method of producing a liposomal formulation comprising the steps of a) dissolving at least one lipid in an organic solvent, b) injecting the mixture of step a) into a circulating aqueous phase, and c) eliminating the solvent.

In a sixteenth aspect, the present invention relates to liposomal formulation producible by the method of the fourteenth aspect.

In a seventeenth aspect, the present invention provides a method of storing CD-RAP, comprising keeping CD-RAP in a liposomal formulation of the eleventh aspect of the present invention.

In an eighteenth aspect, the present invention provides a method of reducing the size of liposomes in a liposomal formulation comprising the steps of a) dissolving at least one lipid in an organic solvent, b) injecting the mixture of step a) into a circulating aqueous phase, and c) eliminating the solvent.

In a nineteenth aspect, the present invention relates to method of reducing the polydispersity of a liposomal formulation comprising the steps of a) dissolving at least one lipid in an organic solvent, b) injecting the mixture of step a) into a circulating aqueous phase, and c) eliminating the solvent.

LIST OF FIGURES

FIG. 1: Schematic drawing of the general process of preparing native CD-RAP from CD-RAP precursor protein FIG. 2: A: Chromatogram of CD-RAP precursor protein before cleavage (Zorbax Column, mobile phase gradient water to acetonitrile, 0.8 ml/min, oven at 60° C., wavelength 214 nm), B: Chromatogram of CD-RAP after cleavage FIG. 3: Fermentation yield data for CD-RAP-constructs with different chain length of the pre-sequence FIG. 4: Fermentation yield data of CD-RAP [g/L] plotted vs. the chain-length of the pre-sequence FIG. 5: Increase of CD-RAP over time after cleavage with different trypsin concentrations (expressed in Units/Litre and in brackets as units per mg of Pre-CD-RAP)

Figure 6:
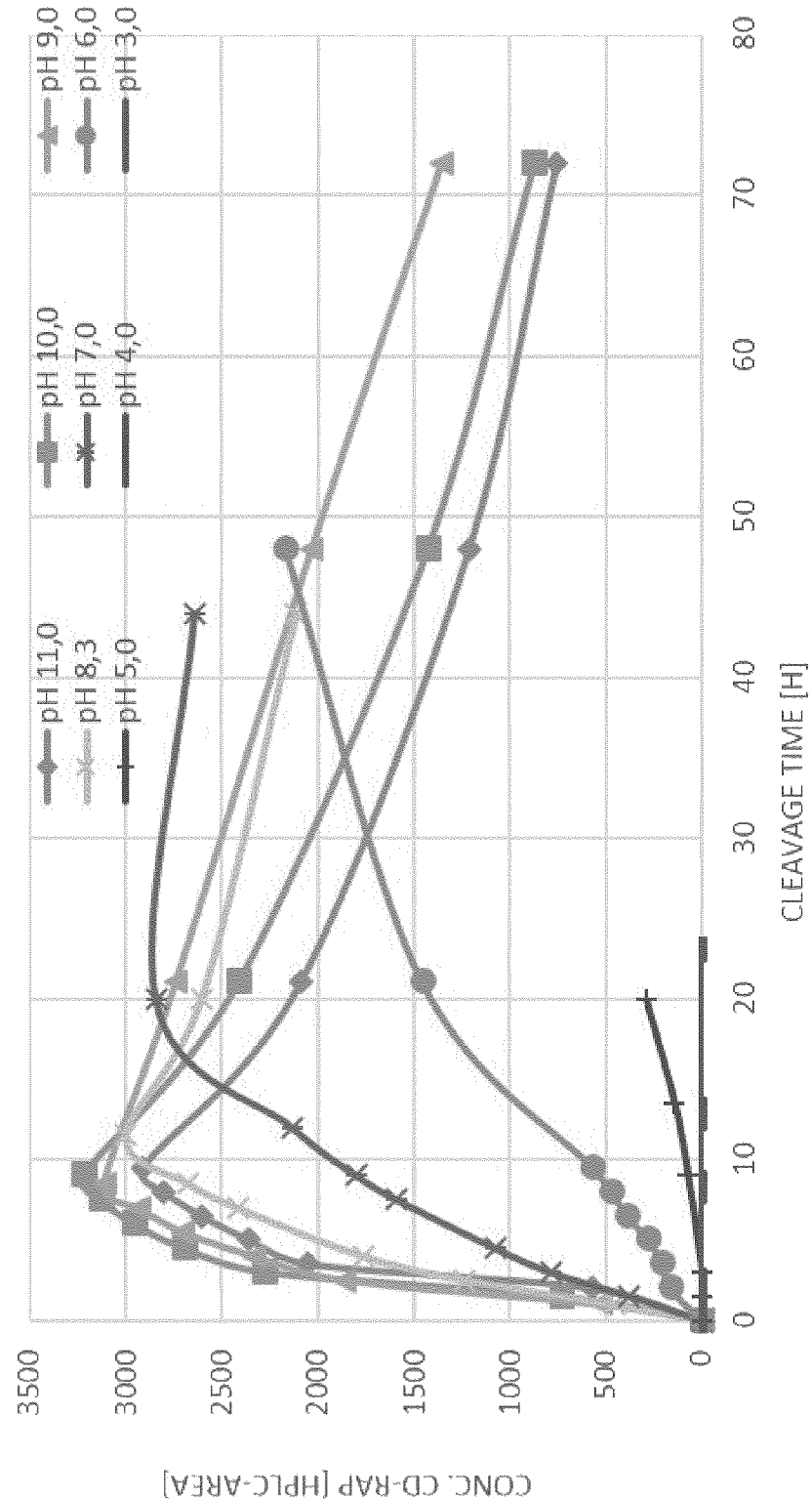

FIG. 6: Trypsin cleavage at different pH increase of CD-RAP

Figure 7:
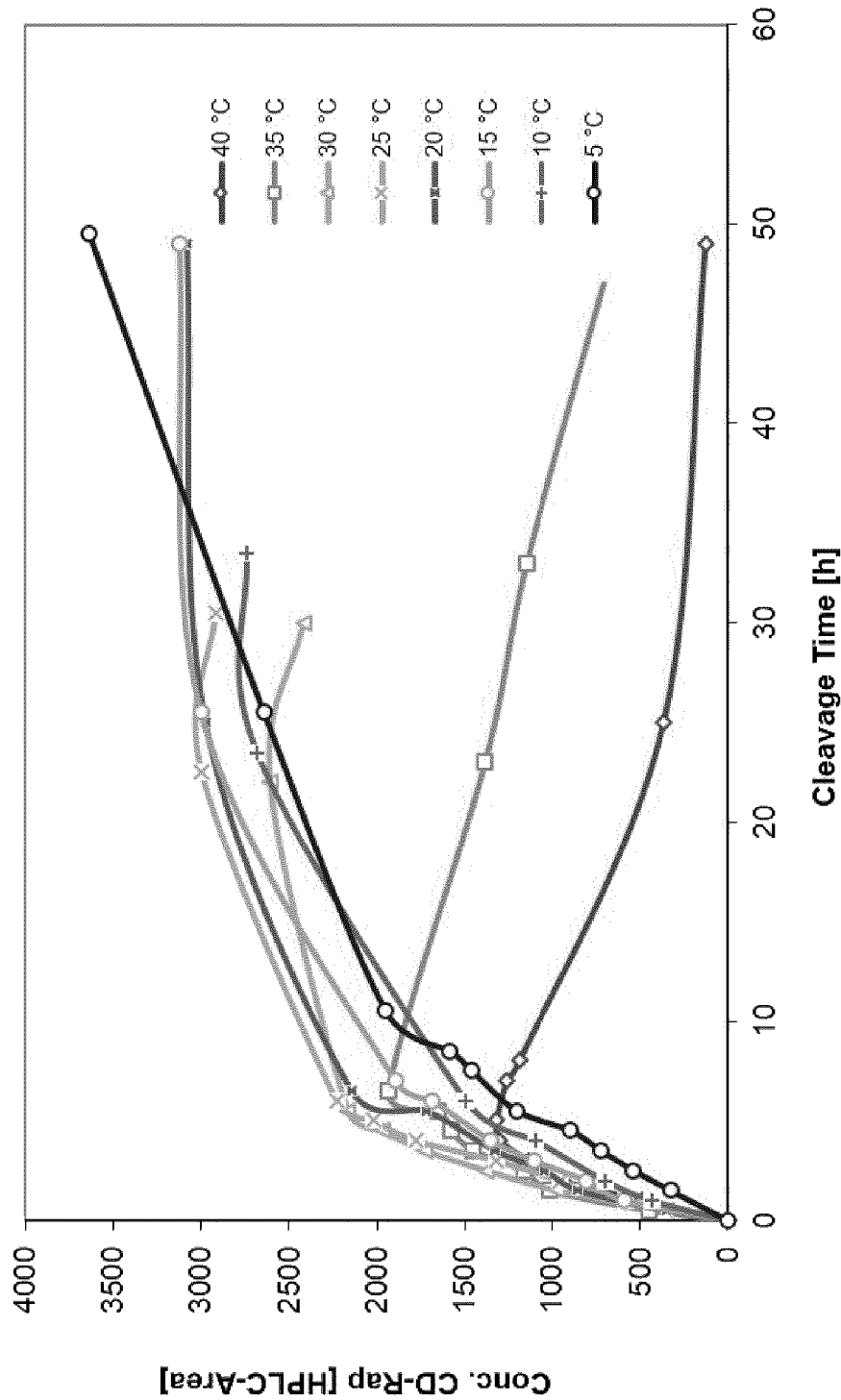

FIG. 7: Trypsin cleavage at different temperatures increase of CD-RAP

FIG. 8: Melting point determination of different rhCD-RAP batches in two buffer systems by DSF; assay concentration of 0.5 mg/mL FIG. 9: pH and osmolality of the formulations prepared in Round 1

FIG. 10: Appearance of the formulations prepared in Round 1 at T=0 and after stress FIG. 11: RP-HPLC results obtained in Round 1 with CD-RAP FIG. 12: pH of the formulations after the third washing step and after pH adjustment with diluted HCl solutions FIG. 13: pH and osmolality of the formulations prepared in Round 2

FIG. 14: Appearance of the formulations prepared in Round 2 at T=0 and after stress FIG. 15: RP-HPLC results obtained in Round 2

FIG. 16: Stability results of CD-RAP drug product batch F531-03-003p064b

FIG. 17: Stability results of placebo batch F531-03-003p063

FIG. 18: Process setup

FIG. 19: Lipid solubility results

FIG. 20: Effect of lipid concentration in the organic phase on particle size

FIG. 21: Effect of the static mixer internal diameter on liposome size

FIG. 22: Effect of aqueous phase flow rate on liposome size

FIG. 23: Combining tested parameters in one batch

FIG. 24: Particle size of the liposomes after mixing with buffer and drug substance FIG. 25: A: Freeze drying program Run 1; B: Freeze drying program Run 2

FIG. 26: Overview of the formulations tested and obtained EE %

FIG. 27: Effect of lipid content on EE % A: step-by-step reconstitution; B: one step reconstitution)

FIG. 28: A: Effect of freeze-drying method on EE %; B: Effect of the reconstitution method on EE %

FIG. 29: Overview of the of formulations tested and obtained EE %

FIG. 30: A: EE % results obtained for the sub-batches of form. F531-03-008P056; B: EE % results obtained for the sub-batches of form. F531-03-008P064

FIG. 31: Stability Results of Liposomal CD-RAP Pk Batches

LIST OF SEQUENCES

SEQ ID NO: 1 amino acid sequence of CD-RAP (107 amino acids):

```
GPMPKLADRKLCADQECSHPISMAVALQDYMAPDCRFLTIHRGQVVY
VFSKLKGRGRLFWGGSVQGDYYGDLAARLGYFPSSIVREDQTLKPGK
VDVKTDKWDFYCQ
```

SEQ ID NO: 2 amino acid sequence of pre-sequence: MATTST

SEQ ID NO: 3 amino acid sequence of pre-sequence: MATTLT

SEQ ID NO: 4 amino acid sequence of pre-sequence: MATTSTG

SEQ ID NO: 5 amino acid sequence of pre-sequence: MATTLTG

SEQ ID NO: 6 amino acid sequence of pre-sequence: MATTSTGN

SEQ ID NO: 7 amino acid sequence of pre-sequence: MATTLTGN

SEQ ID NO: 8 amino acid sequence of pre-sequence: MATTSTGNS

SEQ ID NO: 9 amino acid sequence of pre-sequence: MATTLTGNS

SEQ ID NO: 10 amino acid sequence of pre-sequence: MATTSTGNSA

SEQ ID NO: 11 amino acid sequence of pre-sequence: MATTLTGNSA

SEQ ID NO: 12 amino acid sequence of pre-sequence: MATTSTR

SEQ ID NO: 13 amino acid sequence of pre-sequence: MATTLTR

SEQ ID NO: 14 amino acid sequence of pre-sequence: MATTSTGNSAR

SEQ ID NO: 15 amino acid sequence of pre-sequence: MATTLTGNSAR

SEQ ID NO: 16 amino acid sequence of pre-sequence: MATTSTLTTHWHWHGNSAR

SEQ ID NO: 17 amino acid sequence of pre-sequence: MATTSTGNSAHFQHHHGSLAR

SEQ ID NO: 18 amino acid sequence of pre-sequence: MATTSTGNSAHFQHHHGSLAR

SEQ ID NO: 19 amino acid sequence of pre-sequence: MATTSTGNSARFVNQHLH HHHHHHHGGGENQQQR SEQ ID NO: 20 amino acid sequence of the precursor protein:

MATTSTGNSARFVNQHLHHHHHHHHGGGENQQQRGPMPKLADRKL

CADQECSHPISMAVALQDYMAPDCRFLTIHRGQVVYVFSKLKGRGRL

FWGGSVQGDYYGDLAARLGYFPSSIVREDQTLKPGKVDVKTDKWDF

YCQ

SEQ ID NO: 21 amino acid sequence of CD-RAP (105 amino acids):

MPKLADRKLCADQECSHPISMAVALQDYMAPDCRFLTIHRGQVVYVF
SKLKGRGRLFWGGSVQGDYYGDLAARLGYFPSSIVREDQTLKPGKVD
VKTDKWDFYCQ

DETAILED DESCRIPTION OF THE INVENTION

Definitions

Before the present invention is described in detail below, it is to be understood that this invention is not limited to the particular methodology, protocols and reagents described herein as these may vary. It is also to be understood that the terminology used herein is for the purpose of describing particular embodiments only, and is not intended to limit the scope of the present invention which will be limited only by the appended claims. Unless defined otherwise, all technical and scientific terms used herein have the same meanings as commonly understood by one of ordinary skill in the art.

Several documents are cited throughout the text of this specification. Each of the documents cited herein (including all patents, patent applications, scientific publications, manufacturer's specifications, instructions etc.), whether supra or infra, is hereby incorporated by reference in its entirety. Nothing herein is to be construed as an admission that the invention is not entitled to antedate such disclosure by virtue of prior invention. Some of the documents cited herein are characterized as being "incorporated by reference". In the event of a conflict between the definitions or teachings of such incorporated references and definitions or teachings recited in the present specification, the text of the present specification takes precedence.

In the following, the elements of the present invention will be described. These elements are listed with specific embodiments, however, it should be understood that they may be combined in any manner and in any number to create additional embodiments. The variously described examples and preferred embodiments should not be construed to limit the present invention to only the explicitly described embodiments. This description should be understood to support and encompass embodiments which combine the explicitly described embodiments with any number of the disclosed and/or preferred elements. Furthermore, any permutations and combinations of all described elements in this application should be considered disclosed by the description of the present application unless the context indicates otherwise.

Throughout this specification and the claims which follow, unless the context requires otherwise, the word "comprise", and variations such as "comprises" and "comprising", will be understood to imply the inclusion of a stated integer or step or group of integers or steps but not the exclusion of any other integer or step or group of integers or steps.

As used in this specification and the appended claims, the singular forms "a", "an", and "the" include plural referents, unless the content clearly dictates otherwise.

The term "about" when used in connection with a numerical value is meant to encompass numerical values within a range having a lower limit that is 5% smaller than the indicated numerical value and having an upper limit that is 5% larger than the indicated numerical value.

The term "lipid" as used herein denotes any fat-soluble molecule. Lipids typically consist of an aliphatic hydrocarbon chain, are poorly soluble in water but dissolve in non-polar organic solvents. Lipids are an essential group of molecules in living cells having an important role in energy storage, as structural components of cell membranes, and as signalling molecules. Examples of lipids include but are not limited to fatty acyls, fatty alcohols, sterol lipids such as cholesterol, glycerolipids such as monoglycerides (monoacylglycerol), diglycerides (diacylglycerol) or triglycerides (triacylglycerol, TAG), glycerophospholipids, saccharolipids, sphingolipids, sulfolipids, polyketides, prenol lipids.

The term "fatty acyls" as used herein refers to a diverse group of molecules synthesized by chain elongation of an acetyl-CoA primer with malonyl-CoA (or methylmalonyl-CoA) groups that may contain a cyclic functionality and/or are substituted with heteroatoms. Examples of fatty acyls include but are not limited to fatty acids and conjugates (FA01) such as straight chain fatty acids (FA0101), branched fatty acids (FA0102), unsaturated fatty acids (FA0103), hydroperoxy fatty acids (FA0104), hydroxy fatty acids (FA0105), oxo fatty acids (FA0106), epoxy fatty acids (FA0107), methoxy fatty acids (FA0108), halogenated fatty acids (FA0109), amino fatty acids (FA0110), cyano fatty acids (FA0111), nitro fatty acids (FA0112), thia fatty acids (FA0113), carbocyclic fatty acids (FA0114), heterocyclic fatty acids (FA0115), mycolic acids (FA0116), and dicarboxylic acids (FA0117); octadecanoids (FA02) such as 12-oxophytodienoic acid metabolites (FA0201), jasmonic acids (FA0202), and other octadecanoids (FA0200); eicosanoids (FA03) such as prostaglandins (FA0301), leukotrienes (FA0302), thromboxanes (FA0303), lipoxins (FA0304), hydroxy/hydroperoxyeicosatrienoic acids (FA0305), hdroWhydroperoxyeicosatetraenoic acids (FA0306), hydroxy/hydroperoxyeicosapentaenoic acids (FA0307), epoxyeicosatrienoic acids (FA0308), hepoxilins (FA0309), levuglandins (FA0310), isoprostanes (FA0311), clavulones and derivatives (FA0312), and other Eicosanoids (FA0300); docosanoids (FA04); fatty alcohols (FA05); fatty aldehydes (FA06), fatty esters (FA07) such as wax monoesters (FA0701), wax diesters (FA0702), cyano esters (FA0703), lactones (FA0704), fatty acyl CoAs (FA0705), fatty acyl ACPs (FA0706), fatty acyl carnitines (FA0707), and fatty acyl adenylates (FA0708); fatty amides (FA08) such as primary amides (FA0801), N-acyl amines (FA0802), fatty acyl homoserine lactones (FA0803), and N-acyl ethanolamines (endocannabinoids) (FA0804); fatty nitriles (FA09); fatty ethers (FA10); hydrocarbons (FA11); oxygenated hydrocarbons (FA12); fatty acyl glycosides (FA13); and other fatty acyls (FA00). The fatty acid structure is one of the most fundamental structures of biological lipids, and is commonly used as building-blocks of lipids which are structurally more complex. "Fatty acids" are made of a hydrocarbon chain that comprises a carboxylic acid group conferring to the molecule a polar, hydrophilic head (e.g. glycerol, sphingosine), and a non-polar, hydrophobic tail that is insoluble in water. The carbon chain may be saturated or unsaturated, i.e. may comprise none, or one or more double bonds between two carbon atoms, and may have between 4 and 28 carbon atoms, i.e. 4, 5, 6, 7, 8, 9, 10, 11, 12, 13, 14, 15, 16, 17, 18, 19, 20, 21, 22, 23, 24, 25, 26, 27, or 28 carbon atoms. The double bonds in unsaturated fatty acids exist either as cis or as trans geometric isomerism affecting the molecule's molecular configuration. Further functional groups containing oxygen, halogens, nitrogen, and/or sulfur may also be attached. In living cells, fatty acids are synthesized by chain-elongation of an acetyl-CoA primer with malonyl-CoA or methylmalonyl-CoA groups through the enzyme fatty acid synthases in a process called fatty acid synthesis. Examples of saturated fatty acids include but are not limited to caprylic acid ($CH_3(CH_2)_6COOH$; 8:0), capric acid ($CH_3(CH_2)_8COOH$; 10:0), lauric acid ($CH_3(CH_2)_{10}COOH$; 12:0), myristic acid ($CH_3(CH_2)_{12}COOH$; 14:0), palmitic acid ($CH_3(CH_2)_{14}COOH$; 16:0), stearic acid ($CH_3(CH_2)_{16}COOH$; 18:0), arachidic acid ($CH_3(CH_2)_{18}COOH$; 20:0), behenic acid ($CH_3(CH_2)_{20}COOH$; 22:0), lignoceric acid ($CH_3(CH_2)_{22}COOH$; 24:0), and cerotic acid ($CH_3(CH_2)_{24}COOH$; 26:0).

Examples of unsaturated fatty acids include but are not limited to myristoleic acid ($CH_3(CH_2)_3CH=CH(CH_2)_7COOH$; 14:1), palmitoleic acid ($CH_3(CH_2)_5CH=CH(CH_2)_7COOH$; 16:1), sapienic acid ($CH_3(CH_2)_8CH=CH(CH_2)_4COOH$; 16:1), oleic acid ($CH_3(CH_2)_7CH=CH(CH_2)_7COOH$; 18:1), Elaidic acid ($CH_3(CH_2)_7CH=CH(CH_2)_7COOH$; 18:1), Vaccenic acid ($CH_3(CH_2)_5CH=CH(CH_2)_9COOH$; 18:1), linoleic acid ($CH_3(CH_2)_4CH=CHCH_2CH=CH(CH_2)_7COOH$; 18:2), Linoelaidic acid ($CH_3(CH_2)_4CH=CHCH_2CH=CH(CH_2)_7COOH$, 18:2), and α-linolenic acid ($CH_3CH_2CH=CHCH_2CH=CHCH_2CH=CH(CH_2)_7COOH$; 18:3).

The term "glycerolipids" or "glyceride" refers to esterified glycerol which are mainly composed of mono-, di-, and tri-substituted glycerol with the most prominent member being the fatty acid triesters of glycerol (so-called triglycerides) wherein the three hydroxyl groups of glycerol are each esterified, typically by different fatty acids. Glycerolipids mainly function as energy storage, and thus, constitute the bulk of storage fat in animal tissues. Examples of glycerolipids include but are not limited to monoradylglycerols, diradylglycerols (GL02), triradylglycerols (GL03) such as e.g. glyceryl tristearate (stearin); glycosylmonoradylglycerols (GL04), glycosyldiradylglycerols (GL05), and other glycerolipids (GL00).

Phospholipids are key components of the lipid bilayers of cells serving as a primary component of cellular membranes and binding sites for intra- and intercellular proteins. Phospholipids contain glycerol (glycerophospholipids) or sphingosine (sphingolipids), fatty acids bound to glycerol or sphingosine through ester linkages, a phosphate group, and a simple organic molecule such as e.g. choline, serine, or ethanolamine.

Glycerophosphinolipids comprise glycerol as alcohol to which hydroxyl groups two fatty acids and a phosphine (IUPAC name: phosphane) are esterified. Glycerophosphonolipids comprise glycerol as alcohol to which hydroxyl groups two fatty acids and a phosphorous acid are esterified.

Some glycerophospholipids in eukaryotic cells, such as phosphatidylinositols and phosphatidic acids, also function as either precursors of or directly as membrane-derived second messengers. Furthermore, they are involved in metabolism and cell signalling. Further, there are also alkyl-linked and 1Z-alkenyl-linked (plasmalogen) glycerophospholipids, as well as dialkylether variants in archaebacteria. Examples of glycerophospholipids include but are not limited to glycerophosphocholines (GP01) such as diacylglycerophosphocholines (GP0101), 1-alkyl,2-acylglycerophosphocholines (GP0102), 1-(1Z-alkenyl),2-acylglycerophosphocholines (GP0103), dialkylglycerophosphocholines (GP0104), monoacylglycerophosphocholines (GP0105), monoalkylglycerophosphocholines (GP0106), 1Z-alkenylglycerophosphocholines (GP0107), 1-acyl,2-alkylglycerophosphocholines (GP0108), and 1-acyl,2-(1Z-alkenyl)-glycerophosphocholines (GP0109); glycerophosphoethanolamines (GP02) such as diacylglycerophosphoethanolamines (GP0201), 1-alkyl,2-acylglycerophosphoethanolamines (GP0202), 1-(1Z-alkenyl),2-acylglycerophosphoethanolamines (GP0203), dialkylglycerophosphoethanolamines (GP0204), monoacylglycerophosphoethanolamines (GP0205), monoalkylglycerophosphoethanolamines (GP0206), 1Z-alkenylglycerophosphoethanolamines (GP0207), and 1-acyl,2-alkylglycerophosphoethanolamines (GP0208); glycerophosphoserines (GP03) such as diacylglycerophosphoserines (GP0301), 1-alkyl,2-acylglycerophosphoserines (GP0302), 1-(1Z-alkenyl),2-acylglycerophosphoserines (GP0303), dialkylglycerophosphoserines (GP0304), monoacylglycerophosphoserines (GP0305), monoalkylglycerophosphoserines (GP0306), and 1Z-alkenylglycerophosphoserines (GP0307); glycerophosphoglycerols (GP04) such as diacylglycerophosphoglycerols (GP0401), 1-alkyl,2-acylglycerophosphoglycerols (GP0402), 1-(1Z-alkenyl),2-acylglycerophosphoglycerols (GP0403), dialkylglycerophosphoglycerols (GP0404), monoacylglycerophosphoglycerols (GP0405), monoalkylglycerophosphoglycerols (GP0406), 1Z-alkenylglycerophosphoglycerols (GP0407), diacylglycerophosphodiradylglycerols (GP0408), diacylglycerophosphomonoradylglycerols (GP0409), monoacylglycerophosphomonoradylglycerols (GP0410), and 1-acyl,2-alkylglycerophosphoglycerols (GP0411); glycerophosphoglycerophosphates (GP05) such as diacylglycerophosphoglycerophosphates (GP0501), 1-alkyl,2-acylglycerophosphoglycerophosphates (GP0502), 1-(1Z-alkenyl),2-acylglycerophosphoglycerophosphates (GP0503), dialkylglycerophosphoglycerophosphates (GP0504), monoacylglycerophosphoglycerophosphates (GP0505), monoalkylglycerophosphoglycerophosphates (GP0506), and 1Z-alkenylglycerophosphoglycerophosphates (GP0507); Glycerophosphoinositols (GP06) such as diacylglycerophosphoinositols (GP0601), 1-alkyl,2-acylglycerophosphoinositols (GP0602), 1-(1Z-alkenyl),2-acylglycerophosphoinositols (GP0603), dialkylglycerophosphoinositols (GP0604), monoacylglycerophosphoinositols (GP0605), monoalkylglycerophosphoinositols (GP0606), and 1Z-alkenylglycerophosphoinositols (GP0607); glycerophosphoinositol monophosphates (GP07) such as diacylglycerophosphoinositol monophosphates (GP0701), 1-alkyl,2-acylglycerophosphoinositol monophosphates (GP0702), 1-(1Z-alkenyl),2-acylglycerophosphoinositol monophosphates (GP0703), dialkylglycerophosphoinositol monophosphates (GP0704), monoacylglycerophosphoinositol monophosphates (GP0705), monoalkylglycerophosphoinositol monophosphates (GP0706), and 1Z-alkenylglycerophosphoinositol monophosphates (GP0707); glycerophosphoinositol bisphosphates (GP08) such as diacylglycerophosphoinositol bisphosphates (GP0801), 1-alkyl,2-acylglycerophosphoinositol bisphosphates (GP0802), 1-(1Z-alkenyl),2-acylglycerophosphoinositol bisphosphates (GP0803), monoacylglycerophosphoinositol bisphosphates (GP0804), monoalkylglycerophosphoinositol bisphosphates (GP0805), and 1Z-alkenylglycerophosphoinositol bisphosphates (GP0806); glycerophosphoinositol trisphosphates (GP09) such as diacylglycerophosphoinositol trisphosphates (GP0901), 1-alkyl,2-acylglycerophoshoinositol trisphosphates (GP0902), 1-(1Z-alkenyl),2-acylglycerophosphoinositol trisphosphates (GP0903), monoacylglycerophosphoinositol trisphosphates (GP0904), monoalkylglycerophosphoinositol trisphosphates (GP0905), and 1 Z-alkenylglycerophosphoinositol trisphosphates (GP0906); glycerophosphates (GP10) such as diacylglycerophosphates (GP1001), 1-alkyl,2-acylglycerophosphates (GP1002), 1-(1Z-alkenyl),2-acylglycerophosphates (GP1003), dialkylglycerophosphates (GP1004), monoacylglycerophosphates (GP1005), monoalkylglycerophosphates (GP1006), and 1Z-alkenylglycerophosphates (GP1007); Glyceropyrophosphates (GP11) such as diacylglyceropyrophosphates (GP1101) and monoacylglyceropyrophosphates (GP1102); glycerophosphoglycerophosphoglycerols (GP12) such as diacylglycerophosphoglycerophosphodiradylglycerols (GP1201), diacylglycerophosphoglycerophosphomonoradylglycerols (GP1202), 1-alkyl,2-acylglycerophosphoglycerophosphodiradylglycerols (GP1203), 1-alkyl,2-acylglycerophosphoglycerophosphomonoradylglycerols (GP1204), 1-(1Z-alkenyl),2-acylglycerophosphoglycerophosphodiradylglycerols (GP1205), 1-(1Z-alkenyl),2-acylglycerophosphoglycerophosphomonoradylglycerols (GP1206), monoacylglycerophosphoglycerophosphomonoradylglycerols (GP1207), monoalkylglycerophosphoglycerophosphodiradylglycerols (GP1208), monoalkylglycerophosphoglycerophosphomonoradylglycerols (GP1209), 1Z-alkenylglycerophosphoglycerophosphodiradylglycerols (GP1210), 1Z-alkenylglycerophosphoglycerophosphomonoradylglycerols (GP1211), dialkylglycerophosphoglycerophosphodiradylglycerols (GP1212) and dialkylglycerophosphoglycerophosphomonoradylglycerols (GP1213); CDP-Glycerols (GP13) such as CDP-diacylglycerols (GP1301), CDP-1-alkyl,2-acylglycerols (GP1302), CDP-1-(1Z-alkenyl),2-acylglycerols (GP1303), CDP-dialkylglycerols (GP1304), CDP-monoacylglycerols (GP1305), CDP-monoalkylglycerols (GP1306), and CDP-1Z-alkenylglycerols (GP1307); glycosylglycerophospholipids (GP14) such as diacylglycosylglycerophospholipids (GP1401), 1-alkyl,2-acylglycosylglycerophospholipids (GP1402), 1-(1 Z-alkenyl),2-acylglycosylglycerophospholipids (GP1403), monoacylglycosylglycerophospholipids (GP1404), monoalkylglycosylglycerophospholipids (GP1405), 1Z-alkenylglycosylglycerophospholipids (GP1406), and dialkylglycosylglycerophospholipids (GP1407); glycerophosphoinositolglycans (GP15) such as diacylglycerophosphoinositolglycans (GP1501), 1-alkyl,2-acylglycerophosphoinositolglycans (GP1502), 1-(1Z-alkenyl),2-acylglycerophosphoinositolglycans (GP1503), monoacylglycerophosphoinositolglycans (GP1504), monoalkylglycerophosphoinositolglycans (GP1505), 1Z-alkenylglycerophosphoinositolglycans (GP1506), and dialkylglycerophosphoinositolglycans (GP1507); glycerophosphonocholines (GP16) such as diacylglycerophosphonocholines (GP1601), 1-alkyl,2-acylglycerophosphonocholines (GP1602), 1-(1Z-alkenyl),2-acylglycerophosphonocholines (GP1603), dialkylglycerophosphonocholines (GP1604), monoacylglycerophosphonocholines (GP1605), monoalkylglycerophosphonocholines (GP1606), and 1Z-alkenylglycerophosphonocholines (GP1607); glycerophosphonoethanolamines (GP17) such as diacylglycerophosphonoethanolamines (GP1701), 1-alkyl,2-acylglycerophosphonoethanolamines (GP1702), 1-(1Z-alkenyl), 2-acylglycerophosphonoethanolamines (GP1703), dialkylglycerophosphonoethanolamines (GP1704), monoacylglycerophosphonoethanolamines (GP1705), monoalkylglycerophosphonoethanolamines (GP1706), and 1Z-alkenylglycerophosphonoethanolamines (GP1707); di-glycerol tetraether phospholipids (caldarchaeols) (GP18); glycerol-nonitol tetraether phospholipids (GP19); oxidized glycerophospholipids (GP20) such as oxidized glycerophosphocholines (GP2001), oxidized glycerophosphoethanolamines (GP2002), and oxidized Cardiolipins (GP2003); and other Glycerophospholipids (GP00).

In biological membranes glycerophospholipids including but not limited to phosphatidic acid (phosphatidate) (PA), phosphatidylethanolamine (cephalin) (PE), phosphatidylcholine (lecithin) (PC), phosphatidylserine (PS), and phosphoinositides such as phosphatidylinositol (PI), phosphatidylinositol phosphate (PIP), phosphatidylinositol bisphosphate (PIP2), phosphatidylinositol triphosphate (PIP3), cardiolipin and lysophospholipids, are most prominent.

Naturally occurring phospholipid derivates include but are not limited to egg PC, egg PG, soy PC, hydrogenated soy PC, and sphingomyelin. Synthetic phospholipid derivates include but are not limited to phosphatidic acid (DMPA, DPPA, DSPA), phosphatidylcholine (DDPC, DLPC, DMPC, DPPC, DSPC, DOPC, POPC, DEPC), phosphatidylglycerol (DMPG, DPPG, DSPG, POPG), phosphatidylethanolamine (DMPE, DPPE, DSPE DOPE), phosphatidylserine (DOPS), and PEG phospholipid (mPEG-phospholipid, polyglycerin-phospholipid, funcitionalized-phospholipid, terminal activated-phospholipid).

"Sphingolipids" comprise a sphingoid base backbone with the major sphingoid base of mammals being sphingosine. The main mammalian sphingoid bases are dihydrosphingosine and sphingosine, while dihydrosphingosine and phytosphingosine are the principle sphingoid bases in yeast. The sphingosine backbone may be O-linked to a typically charged head group such as ethanolamine, serine, or choline, and amide-linked to an acyl group, such as a fatty acid. The fatty acids are typically saturated or mono-unsaturated with chain lengths from 16 to 26 carbon atoms. Examples of sphingolipids include but are not limited to sphingoid bases (SP01) such as sphing-4-enines (Sphingosines) (SP0101), sphinganines (SP0102), 4-Hydroxysphinganines (Phytosphingosines) (SP0103), Sphingoid base homologs and variants (SP0104), Sphingoid base 1-phosphates (SP0105), Lysosphingomyelins and lysoglycosphingolipids (SP0106), N-methylated sphingoid bases (SP0107), and Sphingoid base analogs (SP0108); ceramides (SP02) such as N-acylsphingosines (ceramides) (SP0201), N-acyl-sphinganines (dihydroceramides) (SP0202), N-acyl-4-hydroxysphinganines (phytoceramides) (SP0203), acylceramides (SP0204), and ceramide 1-phosphates (SP0205); phosphosphingolipids (SP03) such as ceramide phosphocholines (sphingomyelins) (SP0301), ceramide phosphoethanolamines (SP0302), and ceramide phosphoinositols (SP0303); phosphonosphingolipids (SP04); neutral glycosphingolipids (SP05) such as simple Glc series (SP0501), GalNAc31-3Galα1-4Galβ1-4Glc- (Globo series) (SP0502), GalNAβ1-4Galβ1-4Glc- (Ganglio series) (SP0503), Galβ1-3GlcNAcβ1-3Galβ1-4Glc- (Lacto series) (SP0504), Galfβ1-4GlcNAcβ1-3Galβ1-4Glc- (Neolacto series) (SP0505), GalNAcβ1-3Galα1-3Galβ1-4Glc- (Isoglobo series) (SP0506), GlcNAcβ1-2Manα1-3Manβ1-4Glc- (Mollu series) (SP0507), GalNAcβ1-4GlcNAcβ1-3Manβ1-4Glc-(Arthro series) (SP0508), Gal- (Gala series) (SP0509) and other neutral glycosphingolipids (SP0500); acidic glycosphingolipids (SP06) such as gangliosides (SP0601), sulfoglycosphingolipids (sulfatides) (SP0602), glucuronosphingolipids (SP0603), phosphoglycosphingolipids (SP0604), and other acidic glycosphingolipids (SP0600); basic glycosphingolipids (SP07); amphoteric glycosphingolipids (SP08); arsenosphingolipids (SP09); and other sphingolipids (SP00).

Ceramides (N-acyl-sphingoid bases) are a major subclass of sphingoid base derivatives with amide-linked fatty acids. Biologically relevant examples of ceramides include but are not limited to ceramide phosphorylcholine (SPH), ceramide phosphorylethanolamine (Cer-PE), and ceramide phosphorylglycerol. The major phosphosphingolipids of mammals are sphingomyelins (e.g. ceramide, phosphocholines). "Glycosphingolipids" are composed of one or more sugar residues linked via a glycosidic bond to the sphingoid base. Examples are glycosphingolipids such as but not limited to cerebrosides and gangliosides.

The term "saccharolipids" refers to molecules in which fatty acids are linked directly to a sugar backbone, forming structures that are compatible with membrane bilayers. Examples of saccharolipids include but are not limited to acylaminosugars (SL01), such as monoacylaminosugars (SL0101), diacylaminosugars (SL0102), triacylaminosugars (SL0103), tetraacylaminosugars (SL0104), pentaacylaminosugars (SL0105), hexaacylaminosugars (SL0106), and heptaacylaminosugars (SL0107); acylaminosugar glycans (SL02); acyltrehaloses (SL03); acyltrehalose glycans (SL04); other acyl sugars (SL05); and other saccharolipids (SL00).

Along with glycerophospholipids and sphingolipids "sterol lipids", also called "steroids", such as but not limited to cholesterol and its derivatives, are important components of cellular membrane lipids playing various biological roles as hormones and as signaling molecules. Steroids have a core structure of four fused carbon rings which may be esterified to a carbon chain. The eighteen-carbon (C18) steroids include the estrogen family whereas the C19 steroids comprise the androgens such as testosterone and androsterone. The C21 subclass includes the progestogens as well as the glucocorticoids and mineralocorticoids. The secosteroids, comprising various forms of vitamin D, are characterized by cleavage of the B ring of the core structure. Other examples of sterols are bile acids and their conjugates, which in mammals are oxidized derivatives of cholesterol and are synthesized in the liver. The plant equivalents are the phytosterols, such as β-sitosterol, stigmasterol, and brassicasterol; the latter compound is also used as a biomarker for algal growth. The predominant sterol in fungal cell membranes is ergosterol. Examples of sterol lipids include but are not limited to sterols (ST01) such as cholesterol and derivatives (ST0101), cholesteryl esters (ST0102), ergosterols and C24-methyl derivatives (ST0103), stigmasterols and C24-ethyl derivatives (ST0104), C24-propyl sterols and derivatives (ST0105), gorgosterols and derivatives (ST0106), furostanols and derivatives (ST0107), spirostanols and derivatives (ST0108), furospirostanols and derivatives (ST0109), cycloartanols and derivatives (ST0110), calysterols and cyclopropyl sidechain derivatives (ST0111), cardanolides and derivatives (ST0112), bufanolides and derivatives (ST0113), brassinolides and derivatives (ST0114), solanidines and alkaloid derivatives (ST0115), and withanolides and derivatives (ST0116); steroids (ST02) such as C18 steroids (estrogens) and derivatives (ST0201), C19 steroids (androgens) and derivatives (ST0202), and C21 steroids (gluco/mineralocorticoids, progestogins) and derivatives (ST0203); secosteroids (ST03) such as vitamin D2 and derivatives (ST0301), vitamin D3 and derivatives (ST0302), vitamin D4 and derivatives (ST0303), vitamin D5 and derivatives (ST0304), vitamin D6 and derivatives (ST0305), and vitamin D7 and derivatives (ST0306); Bile acids and derivatives (ST04) such as C24 bile acids, alcohols, and derivatives (ST0401), C26 bile acids, alcohols, and derivatives (ST0402), C27 bile acids, alcohols, and derivatives (ST0403), C28 bile acids, alcohols, and derivatives (ST0404), C22 bile acids, alcohols, and derivatives (ST0405), C23 bile acids, alcohols, and derivatives (ST0406), C25 bile acids, alcohols, and derivatives (ST0407), and C29 bile acids, alcohols, and derivatives (ST0408); Steroid conjugates (ST05) such as glucuronides (ST0501), sulfates (ST0502), glycine conjugates (ST0503), taurine conjugates (ST0504) and other Steroid conjugates (ST0505); and other sterol lipids (ST00).

The term "polyketides" as used herein refers to a family comprising structurally very diverse members all of which are synthesized via the polyketide synthase pathway through the decarboxylative condensation of malonyl-CoA derived extender units in a similar process to fatty acid synthesis. Polyketides are broadly divided into three classes: type I polyketides (typically macrolides produced by multimodular megasynthases), type II polyketides (typically aromatic molecules produced by the iterative action of dissociated enzymes), and type III polyketides (typically small aromatic molecules produced by fungal species). Commercially used polyketide include natural antibiotics, antifungals, cytostatics, anticholesteremic, antiparasitics, coccidiostats, animal growth promoters and insecticides. Examples of polyketides include but are not limited to linear polyketides (PK01); halogenated acetogenins (PK02); annonaceae acetogenins (PK03); macrolides and lactone polyketides (PK04); ansamycins and related polyketides (PK05); polyenes (PK06); linear tetracyclines (PK07); angucyclines (PK08); polyether polyketides (PK09); aflatoxins and related substances (PK10); cytochalasins (PK11); flavonoids (PK12) such as anthocyanidins (PK1201), flavans, flavanols and leucoanthocyanidins (PK1202), proanthocyanidins (PK1203), biflavonoids and polyflavonoids (PK1204), isoflavonoids (PK1205), rotenoid flavonoids (PK1206), pterocarpans (PK1207), isoflavans (PK1208), coumestan flavonoids (PK1209), neoflavonoids (PK1210), flavones and flavonols (PK1211), chalcones and dihydrochalcones (PK1212), aurone flavonoids (PK1213), flavanones (PK1214), dihydroflavonols (PK1215), and other flavonoids (PK1216); aromatic polyketides (PK13) such as monocyclic aromatic polyketides (PK1301), naphthalenes and naphthoquinones (PK1302), benzoisochromanquinones (PK1303), anthracenes and phenanthrenes (PK1304), anthracyclinones (PK1305), dibenzofurans, griseofulvins, dibenzopyrans and xanthones (PK1306), diphenylmethanes, acylphloroglucinols and benzophenones (PK1307), depsides and depsidones (PK1308), diphenyl ethers, biphenyls, dibenzyls and stilbenes (PK1309), benzofuranoids (PK1310), benzopyranoids (PK1311), and other aromatic polyketides (PK1312); nonribosomal peptide/polyketide hybrids (PK14); and other polyketides (PK00).

The term "prenol lipids" or "isoprenolides" refers to molecules synthesized from the five carbon precursors isopentenyl diphosphate and dimethylallyl diphosphate and are mainly produced via the mevalonic acid pathway. In some bacteria (e.g. *Escherichia coli*) and plants, isoprenoid precursors are made via the methylerythritol phosphate pathway. Because simple isoprenoids (linear alcohols, diphosphates, etc.) are formed by the successive addition of C5 units, isoprenoids are conveniently classified accordingly, with a polyterpene subclass for those structures containing more than 40 carbons (i.e., 8 isoprenoid units). Prenol lipids and their phosphorylated derivatives play important roles in the transport of oligosaccharides across membranes. Polyprenol phosphate sugars and polyprenol diphosphate sugars function in extracytoplasmic glycosylation reactions, in extracellular polysaccharide biosynthesis (for instance, peptidoglycan polymerization in bacteria), and in eukaryotic protein N-glycosylation. Examples of prenol lipids include but are not limited to isoprenoids (PR01) such as C5 isoprenoids (hemiterpenes) (PR0101), C10 isoprenoids (monoterpenes) (PR0102), C15 isoprenoids (sesquiterpenes) (PR0103), C20 isoprenoids (diterpenes) (PR0104), C25 isoprenoids (sesterterpenes) (PR0105), C30 isoprenoids (triterpenes) (PR0106), C40 isoprenoids (tetraterpenes) (PR0107), polyterpenes (PR0108), and retinoids (PR0109); quinones and hydroquinones (PR02) such as ubiquinones (PR0201), vitamin E (PR0202), and vitamin K (PR0203); polyprenols (PR03) such as bactoprenols (PR0301), bactoprenol monophosphates (PR0302), bactoprenol diphosphates (PR0303), phytoprenols (PR0304), phytoprenol monophosphates (PR0305), phytoprenol diphosphates (PR0306), dolichols (PR0307), dolichol monophosphates (PR0308), and dolichol diphosphates (PR0309); hopanoids (PR04); and other prenol lipids (PR00).

The term "lipid bilayer" as used herein refers to a double layer structure of lipids, typically spontaneously formed in aqueous environments, wherein the hydrophilic heads face the water at each surface of the bilayer, and the hydrophobic tails are shielded from the water in the interior. As used herein, the term encompasses bilayers of all geometries including but not limited to planar and curved bilayers.

The term "micelle" as used herein refers to an aggregate of lipids dispersed in a liquid colloid. A typical micelle in aqueous solution forms an aggregate wherein the hydrophilic heads are in contact with the surrounding solution and the hydrophobic tails are in the center of the micelle. In a non-polar solvent, certain lipids may also form inverted micelles.

The term "liposome" as used throughout the description and the claims refers to a vesicle comprising a lipid bilayer membrane. Thus, liposomes differ from micelles in that they comprise a lipid bilayer whereas micelles are composed of lipid monolayers. The lipid membrane of the liposome may comprise components such as but not limited to lipids, proteins, and other membrane-associated components. The major types of liposomes include multilamellar vesicle (MLV), small unilamellar vesicle (SUV), large unilamellar vesicle (LUV), giant unilamellar vesicle (GUV). Typically, the diameter of SUV and LUV liposomes is between 1 nm and 1 µm and the diameter of GUV liposomes is between 1 µm and 300 µm, i.e. 1, 2, 3, 4, 5, 10, 15, 20, 25, 50, 75, 100, 150, 200, 250, or 300 µm. Typically, liposomes encapsulate a liquid core, often an aqueous solution, inside the hydrophobic membrane. Whilst dissolved hydrophilic solutes cannot readily pass through the lipid bilayer, hydrophobic chemicals can be dissolved into the membrane, thus, a liposome may comprise both hydrophobic and hydrophilic molecules. The lipid bilayer of a liposome may fuse with other bilayers such as other liposomes or cell membranes. Thereby liposomes may deliver their contents to the second liposome or to the cell. Thus, to avoid the fusion of two neighboring liposomes, these liposomes are typically kept at a certain distance from each other to prevent the fusion of the lipid bilayers. The extent of the distance between two liposomes depends on the size of the liposomes, the composition of liposomes and the chemical nature of the solvent.

The terms "nucleic acid" or "nucleic acid molecule" are used synonymously and are understood as single or double-stranded oligo- or polymers of deoxyribonucleotide or ribonucleotide bases or both. Typically, a nucleic acid is formed through phosphodiester bonds between the individual nucleotide monomers. In the context of the present invention, the term nucleic acid includes but is not limited to ribonucleic acid (RNA) and deoxyribonucleic acid (DNA) molecules. The depiction of a single strand of a nucleic acid also defines (at least partially) the sequence of the complementary strand. The nucleic acid may be single or double stranded, or may contain portions of both double and single stranded sequences. The nucleic acid may be obtained by biological, biochemical or chemical synthesis methods or any of the methods known in the art. As used herein, the term "nucleic acid" comprises the terms "polynucleotide" and "oligonucleotide". The term "oligonucleotide" when used in the context of one of the different aspects of present invention, refers to a nucleic acid of up to about 50 nucleotides, e.g. 2 to about 50 nucleotides in length. The term "polynucleotide" when used in the context of one of the different aspects of present invention, refers to a nucleic acid of more than about 50 nucleotides in length, e.g. 51 or more nucleotides in length. Probes and Primers are short polynucleotides or oligonucleotides for the detection of nucleic acids in a sample or in vivo by hybridizing (probe) to the target nucleic acid or by hybridization to and amplification of the target nucleic acid. The term "open reading frame" (ORF) refers to a sequence of nucleotides, that can be translated into amino acids. Typically, such an ORF contains a start codon, a subsequent region usually having a length which is a multiple of 3 nucleotides, but does not contain a stop codon (TAG, TAA, TGA, UAG, UAA, or UGA) in the given reading frame. Typically, ORFs occur naturally or are constructed artificially, i.e. by gene-technological means. An ORF codes for a protein where the amino acids into which it can be translated form a peptide-linked chain.

Amino acids are organic compounds composed of amine (—NH2) and carboxylic acid (—COOH) functional groups, along with a side-chain specific to each amino acid. Typically, amino acids are classified by the properties of their side-chain into four groups: the side-chain can make an amino acid a weak acid or a weak base, a hydrophile if the side-chain is polar or a hydrophobe if it is nonpolar. Standard amino acids are the following:

| Amino Acid | 3-Letter http://en.wikipedia.org/wiki/Amino acid-cite note Hausman 118 | 1-Letter | Side-chain polarity | Side-chain charge (pH 7.4) | Hydropathy index | MW (Weight) |
| --- | --- | --- | --- | --- | --- | --- |
| Alanine | Ala | A | nonpolar | neutral | 1.8 | 89 |
| Arginine | Arg | R | Basic polar | positive | −4.5 | 174 |
| Asparagine | Asn | N | polar | neutral | −3.5 | 132 |
| Aspartic acid | Asp | D | acidic polar | negative | −3.5 | 133 |

-continued

| Amino Acid | 3-Letter http://en.wikipedia.org/wiki/Amino acid-cite note Hausman 118 | 1-Letter | Side-chain polarity | Side-chain charge (pH 7.4) | Hydropathy index | MW (Weight) |
|---|---|---|---|---|---|---|
| Cysteine | Cys | C | nonpolar | neutral | 2.5 | 121 |
| Glutamic acid | Glu | E | acidic polar | negative | −3.5 | 147 |
| Glutamine | Gln | Q | polar | neutral | −3.5 | 146 |
| Glycine | Gly | G | nonpolar | neutral | −0.4 | 75 |
| Histidine | His | H | Basic polar | positive(10%) neutral(90%) | −3.2 | 155 |
| Isoleucine | Ile | I | nonpolar | neutral | 4.5 | 131 |
| Leucine | Leu | L | nonpolar | neutral | 3.8 | 131 |
| Lysine | Lys | K | Basic polar | positive | −3.9 | 146 |
| Methionine | Met | M | nonpolar | neutral | 1.9 | 149 |
| Phenylalanine | Phe | F | nonpolar | neutral | 2.8 | 165 |
| Proline | Pro | P | nonpolar | neutral | −1.6 | 115 |
| Serine | Ser | S | polar | neutral | −0.8 | 105 |
| Threonine | Thr | T | polar | neutral | −0.7 | 119 |
| Tryptophan | Trp | W | nonpolar | neutral | −0.9 | 204 |
| Tyrosine | Tyr | Y | polar | neutral | −1.3 | 181 |
| Valine | Val | V | nonpolar | neutral | 4.2 | 117 |

In the context of the different aspects of present invention, the term "peptide" refers to a short polymer of amino acids linked by peptide bonds. It has the same chemical (peptide) bonds as proteins, but is commonly shorter in length. The shortest peptide is a dipeptide, consisting of two amino acids joined by a single peptide bond. There can also be a tripeptide, tetrapeptide, pentapeptide, etc. Preferably, the peptide has a length of up to 8, 10, 12, 15, 18 or 20 amino acids. A peptide has an amino end and a carboxyl end, unless it is a cyclic peptide.

In the context of the different aspects of present invention, the term "polypeptide" refers to a single linear chain of amino acids bonded together by peptide bonds and preferably comprises at least about 21 amino acids. A polypeptide can be one chain of a protein that is composed of more than one chain or it can be the protein itself if the protein is composed of one chain.

In the context of the different aspects of present invention, the term "protein" refers to a molecule comprising one or more polypeptides that resume a secondary and tertiary structure and additionally refers to a protein that is made up of several polypeptides, i.e. several subunits, forming quaternary structures. In the context of present invention, the primary structure of a protein or polypeptide is the sequence of amino acids in the polypeptide chain. The secondary structure in a protein is the general three-dimensional form of local segments of the protein. It does not, however, describe specific atomic positions in three-dimensional space, which are considered to be tertiary structure. In proteins, the secondary structure is defined by patterns of hydrogen bonds between backbone amide and carboxyl groups. The tertiary structure of a protein is the three-dimensional structure of the protein determined by the atomic coordinates. The quaternary structure is the arrangement of multiple folded or coiled protein or polypeptide molecules molecules in a multi-subunit complex. The terms "amino acid chain" and "polypeptide chain" are used synonymously in the context of present invention.

The term "folding" or "protein folding" as used herein refers to the process by which a protein assumes its three-dimensional shape or conformation, i.e. whereby the protein is directed to form a specific three-dimensional shape through firstly non-covalent interactions, such as but not limited to hydrogen bonding, metal coordination, hydrophobic forces, van der Waals forces, pi-pi interactions, and/or electrostatic effects. Secondly, two intramolecular disulphide bonds are formed in the folding process. The term "folded protein" thus, refers to a protein its three-dimensional shape, such as its secondary, tertiary, or quaternary structure.

"Denaturation" is a process in which proteins lose their quaternary, tertiary and/or secondary structure which is present in their native state, typically resulting in a loss of their biological function. Denatured proteins can exhibit a wide range of characteristics, including but not limited to conformational change, loss of solubility, aggregation, or complete degradation Several environmental factors influence the stability of a protein, i.e. the structural, three-dimensional integrity allowing the protein to fulfil its function. These factor include but are not limited to temperature, radiation, pH value of the surrounding medium, presence of peptidases/proteases, protein concentration, salt concentration, solvent, as well as time.

The term "degradation" as used herein refers to the process, wherein proteins lose their primary, secondary, tertiary and/or quaternary structure. Accordingly, the term "degradation" encompasses the denaturation of the protein as well as the removal of single amino acids or several amino acids from the peptide chain or the cleavage of the peptide chain into two or more fragments The term "aggregation" as used herein refers to the process wherein two or more proteins accumulate and/or clump together. Aggregation may occur of intact, native proteins as well as of degraded protein. Often protein aggregation is caused by the exposure of hydrophobic groups of proteins which then accumulate.

CD-RAP is a secreted single-domain protein (107 aa mature protein, 12 kDa, Genbank Accession No.: AAH05910.1, GI:13543500), which contains an antiparallel beta-sheet and two disulfide bonds. TANGO, MIA-2, OTOR are CD-RAP homologous proteins (sequence identity of 44% and sequence homology of ~80%). The alias name of CD-RAP is MIA for autocrine-secreted melanoma tumour growth-inhibiting activity. Blesch et al., (1994) cloned MIA as a novel type of growth regulatory factor from supernatants of the malignant melanoma cell line HTZ-19 dM. Weilbach et al. (1990) hypothesized that MIA is part of a growth-regulatory network. Independently, CD-RAP was cloned by Dietz and Sandell (1996) from bovine chondrocytes as a protein whose expression is downregulated by retinoic acid treatment. As retinoic acid suppresses the differentiated phenotype of chondrocytes, the functional context of CD-RAP (cartilage-derived retinoic acid sensitive protein) is seen in maintaining the differentiated phenotype of chondrocytes, i.e. that chondrocytes maintain the synthesis of cartilage matrix.

CD-RAP is required for differentiation in cartilage upstream of the transcription factor Sox9 (Moser, Bosserhoff, Hunziker, Sandell, Fassler, Buettner 2002. Ultrastructural cartilage abnormalities in MIA/CD-RAP-deficient mice. Molecular and Cellular Biology (2002), 22(5), 1438-1445). In the presence of CD-RAP, human mesenchymal stem cells showed an upregulation of the cartilage markers Aggrecan, Osteocalcin and Collagen type II mRNA's in pellet cultures (Tscheudschilsuren, Bosserhoff, Schlegel, Vollmer, Anton, Alt, Schnettler, Brandt, Proetzel, 2006. Regulation of mesenchymal stem cell and chondrocyte differentiation by MIA. Exp Cell Res. 2006 Jan. 1; 312(1): 63-72). CD-RAP prevents osteogenic differentiation of chondrocytes by maintaining their phenotype in cooperation with BMP-2 and TGFbeta3 and thus preventing them to further differentiate into bone (Tscheudschilsuren, Bosserhoff, Schlegel, Vollmer, Anton, Alt, Schnettler, Brandt, Proetzel, 2006. Regulation of mesenchymal stem cell and chondrocyte differentiation by MIA. Exp Cell Res. 2006 Jan. 1; 312(1):63-72). CD-RAP is described to interact with fibronectin (found in many extracellular matrices), to bind directly to integrin alpha4 beta1 and alpha5 beta1 and negatively modulates integrin activity. Integrins serve chondrocytes as 'sensors' to detect changes in the matrix that surrounds them. Interaction with integrin alpha5 modulates ERK signaling (Schubert, Schlegel, Schmid, Opolka, Grassel, Humphries, Bosserhoff, 2010. Modulation of cartilage differentiation by melanoma inhibiting activity/cartilage-derived retinoic acid-sensitive protein (MIA/CD-RAP). Exp Mol Med. 2010 Mar. 31; 42(3):166-74) known to block chondrogenic differentiation.

Proteins and polypeptide of the present invention (including protein derivatives, protein variants, protein fragments, protein segments, protein epitops and protein domains) can be further modified by chemical modification. This means such a chemically modified polypeptide comprises other chemical groups than the 20 naturally occurring amino acids. Examples of such other chemical groups include without limitation glycosylated amino acids and phosphorylated amino acids. Chemical modifications of a polypeptide may provide advantageous properties as compared to the parent polypeptide, e.g. one or more of enhanced stability, increased biological half-life, or increased water solubility. Chemical modifications applicable to the variants usable in the present invention include without limitation: PEGylation, glycosylation of non-glycosylated parent polypeptides, or the modification of the glycosylation pattern present in the parent polypeptide. The protein may also have non-peptide groups attached, such as e.g. prosthetic groups or cofactors.

The term "expression level" refers to the amount of gene product present in the body or a sample at a certain point of time. The expression level can e.g. be measured/quantified/detected by means of the protein or mRNA expressed from the gene. The expression level can for example be quantified by normalizing the amount of gene product of interest present in a sample with the total amount of gene product of the same category (total protein or mRNA) in the same sample or a reference sample (e.g. a sample taken at the same time from the same individual or a part of identical size (weight, volume) of the same sample) or by identifying the amount of gene product of interest per defined sample size (weight, volume, etc.). The expression level can be measured or detected by means of any method as known in the art, e.g. methods for the direct detection and quantification of the gene product of interest (such as mass spectrometry) or methods for the indirect detection and measurement of the gene product of interest that usually work via binding of the gene product of interest with one or more different molecules or detection means (e.g. primer(s), probes, antibodies, protein scaffolds) specific for the gene product of interest. The determination of the level of gene copies comprises also the determination of the absence or presence of one or more fragments (e.g. via nucleic acid probes or primers, e.g. quantitative PCR, Multiplex ligation-dependent probe amplification (MLPA) PCR) is also within the knowledge of the skilled artisan.

The term "post-translational" used herein refers to events that occur after the translation of a nucleotide triplet into an amino acid and the formation of a peptide bond to the proceeding amino acid in the sequence. Such post-translational events may occur after the entire polypeptide was formed or already during the translation process on those parts of the polypeptide that have already been translated. Post-translational events typically alter or modify the chemical or structural properties of the resultant polypeptide. Examples of post-translational events include but are not limited to events such as glycosylation or phosphorylation of amino acids, or cleavage of the peptide chain, e.g. by an endopeptidase.

The term "co-translational" used herein refers to events that occur during the translation process of a nucleotide triplet into an amino acid chain. Those events typically alter or modify the chemical or structural properties of the resultant amino acid chain. Examples of co-translational events include but are not limited to events that may stop the translation process entirely or interrupted the peptide bond formation resulting in two discreet translation products.

As used herein, the term "variant" is to be understood as a polypeptide or protein which differs in comparison to the polypeptide or protein from which it is derived by one or more changes in its length or sequence. The polypeptide or protein from which a polypeptide variant or protein variant is derived is also known as the parent polypeptide or protein. The term "variant" comprises "fragments" or "derivatives" of the parent molecule. Typically, "fragments" are smaller in length or size than the parent molecule, whilst "derivatives" exhibit one or more differences in their sequence in comparison to the parent molecule. Also encompassed modified molecules such as but not limited to post-translationally modified proteins (e.g. glycosylated, biotinylated, phosphorylated, ubiquitinated, palmitoylated, or proteolytically cleaved proteins). A variant may be constructed artificially, preferably by gene-technological means whilst the parent polypeptide or protein is a wild-type polypeptide or protein. However, also naturally occurring variants are to be understood to be encompassed by the term "variant" as used herein. Further, the variants usable in the present invention may also be derived from homologs, orthologs, or paralogs of the parent molecule or from artificially constructed variants, provided that the variant exhibits at least one biological activity of the parent molecule, i.e. is functionally active.

A "variant" as used herein, can be characterized by a certain degree of sequence identity to the parent polypeptide or parent protein from which it is derived. More precisely, a protein variant in the context of the present invention exhibits at least 80% sequence identity to its parent polypeptide. The term "at least 80% sequence identity" is used throughout the specification with regard to polypeptide sequence comparisons. This expression preferably refers to a sequence identity of at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% to the respective reference polypeptide or to the respective reference polynucleotide. Preferably, the polypeptide in question and the reference polypeptide exhibit the indicated sequence identity over a continuous stretch of 20, 30, 40, 45, 50, 60, 70, 80, 90, 100 or more amino acids or over the entire length of the reference polypeptide.

A derivative of the present invention may exhibit a total number of up to 100 (up to 1, 2, 3, 4, 5, 6, 7, 8, 9, 10, 15, 20, 25, 30, 35, 40, 45, or 50) changes in the amino acid sequence (i.e. exchanges, insertions, deletions, N-terminal truncations, and/or C-terminal truncations). The amino acid exchanges may be conservative and/or non-conservative. In preferred embodiments, a derivative of the present invention differs from the polypeptide or protein or domain from which it is derived by up to 1, 2, 3, 4, 5, 6, 7, 8, 9, 10, 15, 20, 25, 30, 35, 40, 45, or 50 amino acid exchanges, preferably conservative amino acid changes.

The terms "deletion variant" and "fragment" are used interchangeably herein. Such variants comprise N-terminal truncations, C-terminal truncations and/or internal deletions. A fragment may be naturally occurring (e.g. splice variants) or it may be constructed artificially, preferably by gene-technological means. Preferably, a fragment (or deletion variant) has a deletion of up to 1, 2, 3, 4, 5, 6, 7, 8, 9, 10, 15, 20, 25, 30, 35, 40, 45, 50, 55, 60, 65, 70, 75, 80, 85, 90, 95, or 100 amino acids at its N-terminus and/or at its C-terminus and/or internally as compared to the parent polypeptide, preferably at its N-terminus, at its N- and C-terminus, or at its C-terminus.

In case where two sequences are compared and the reference sequence is not specified in comparison to which the sequence identity percentage is to be calculated, the sequence identity is to be calculated with reference to the longer of the two sequences to be compared, if not specifically indicated otherwise. If the reference sequence is indicated, the sequence identity is determined on the basis of the full length of the reference sequence indicated by the respective SEQ ID, if not specifically indicated otherwise. For example, a peptide sequence consisting of 20 amino acids compared to the amino acid sequence of CD-RAP according to SEQ ID NO: 1 may exhibit a maximum sequence identity percentage of 18.7% (20/107) while a sequence with a length of 54 amino acids may exhibit a maximum sequence identity percentage of 50.46% (54/107). The similarity of the amino acid sequences, i.e. the percentage of sequence identity, can be determined via sequence alignments. Such alignments can be carried out with several art-known algorithms, preferably with the mathematical algorithm of Karlin and Altschul (Karlin & Altschul (1993) Proc. Natl. Acad. Sci. USA 90: 5873-5877), with hmmalign (HMMER package, http://hmmer.wustl.edu/) or with the CLUSTAL algorithm (Thompson, J. D., Higgins, D. G. & Gibson, T. J. (1994) Nucleic Acids Res. 22, 4673-80) available e.g. on http://www.ebi.ac.uk/Tools/clustalw/ or on http://www.ebi.ac.uk/Tools/clustalw2/index.html or on http://npsa-pbil.ibcp.fr/cgi-bin/npsa_automat.pl?page=/NPSA/npsa_clustalw.html. Preferred parameters used are the default parameters as they are set on http://www.ebi-.ac.uk/Tools/clustalw/ or http://www.ebi.ac.uk/Tools/clustalw2/index.html. The grade of sequence identity (sequence matching) may be calculated using e.g. BLAST, BLAT or BlastZ (or BlastX). A similar algorithm is incorporated into the BLASTN and BLASTP programs of Altschul et al. (1990) J. Mol. Biol. 215: 403-410. BLAST protein searches are performed with the BLASTP program, score=50, word length=3, to obtain amino acid sequences homologous to the parent polypeptide. To obtain gapped alignments for comparative purposes, Gapped BLAST is utilized as described in Altschul et al. (1997) Nucleic Acids Res. 25: 3389-3402. When utilizing BLAST and Gapped BLAST programs, the default parameters of the respective programs are used. Sequence matching analysis may be supplemented by established homology mapping techniques like Shuffle-LAGAN (Brudno M., Bioinformatics 2003b, 19 Suppl 1:154-162) or Markov random fields. When percentages of sequence identity are referred to in the present application, these percentages are calculated in relation to the full length of the longer sequence, if not specifically indicated otherwise.

Additionally or alternatively, a deletion variant may occur not due to structural deletions of the respective amino acids as described above, but due to these amino acids being inhibited or otherwise not able to fulfil their biological function. Typically, such functional deletion occurs due to the insertions to or exchanges in the amino acid sequence that changes the functional properties of the resultant protein, such as but not limited to alterations in the chemical properties of the resultant protein (i.e. exchange of hydrophobic amino acids to hydrophilic amino acids), alterations in the post-translational modifications of the resultant protein (e.g. post-translational cleavage or glycosylation pattern), or alterations in the secondary or tertiary protein structure. Additionally or alternatively, a functional deletion may also occur due to transcriptional or post-transcriptional gene silencing (e.g. via siRNA) or the presence or absence of inhibitory molecules such as but not limited to protein inhibitors or inhibitory antibodies.

Semi-conservative and especially conservative amino acid substitutions, wherein an amino acid is substituted with a chemically related amino acid, are preferred. Typical substitutions are among the aliphatic amino acids, among the amino acids having aliphatic hydroxyl side chain, among the amino acids having acidic residues, among the amide derivatives, among the amino acids with basic residues, or the amino acids having aromatic residues. Typical semi-conservative and conservative substitutions are:

| Amino acid | Conservative substitution | Semi-conservative substitution |
|---|---|---|
| A | G; S; T | N; V; C |
| C | A; V; L | M; I; F; G |
| D | E; N; Q | A; S; T; K; R; H |
| E | D; Q; N | A; S; T; K; R; H |
| F | W; Y; L; M; H | I; V; A |
| G | A | S; N; T; D; E; N; Q |
| H | Y; F; K; R | L; M; A |
| I | V; L; M; A | F; Y; W; G |
| K | R; H | D; E; N; Q; S; T; A |
| L | M; I; V; A | F; Y; W; H; C |

-continued

| Amino acid | Conservative substitution | Semi-conservative substitution |
|---|---|---|
| M | L; I; V; A | F; Y; W; C; |
| N | Q | D; E; S; T; A; G; K; R |
| P | V; I | L; A; M; W; Y; S; T; C; F |
| Q | N | D; E; A; S; T; L; M; K; R |
| R | K; H | N; Q; S; T; D; E; A |
| S | A; T; G; N | D; E; R; K |
| T | A; S; G; N; V | D; E; R; K; I |
| V | A; L; I | M; T; C; N |
| W | F; Y; H | L; M; I; V; C |
| Y | F; W; H | L; M; I; V; C |

Changing from A, F, H, I, L, M, P, V, W or Y to C is semi-conservative if the new cysteine remains as a free thiol. Furthermore, the skilled person will appreciate that glycines at sterically demanding positions should not be substituted and that P should not be introduced into parts of the protein which have an alpha-helical or a beta-sheet structure.

The term "cleavage site" as used herein refers to an amino acid sequence or nucleotide sequence where this sequence directs the division, e.g. because it is recognized by a cleaving enzyme, and/or can be divided. Typically, a polypeptide chain is cleaved by hydrolysis of one or more peptide bonds that link the amino acids and a polynucleotide chain is cleaved by hydrolysis of one or more of the phosphodiester bond between the nucleotides. Cleavage of peptide- or phosphodiester-bonds may originate from chemical or enzymatic cleavage. Enzymatic cleavage refers to such cleavage being attained by proteolytic enzymes including but not limited to restriction endonuclease (e.g. type I, type II, type II, type IV or artificial restriction enzymes) and endo- or exo-peptidases or -proteases (e.g. serine-proteases, cysteine-proteases, metallo-proteases, threonine proteases, aspartate proteases, glutamic acid proteases). Typically, enzymatic cleavage occurs due to self-cleavage or is effected by an independent proteolytic enzyme. Enzymatic cleavage of a protein or polypeptide can happen either co- or post-translational. Accordingly, the term "endopeptidase cleavage site" used herein, refers to a cleavage cite within the amino acid or nucleotide sequence where this sequence is cleaved or is cleavable by an endopeptidase (e.g. an enteropeptidase or a PA clan protease). Examples of endopeptidases include but are not limited to trypsin, chymotrypsin, pepsin, elastase, thrombin, collagenase, furin, thermolysin, endopeptidase V8, cathepsins, glutamyl endopeptidase.

Alternatively, the term "cleavage site" refers to an amino acid sequence or nucleotide sequence that prevents the formation of peptide- or phosphodiester-bonds between amino acids or nucleotides, respectively. For instance, the bond formation may be prevented due to co-translational self-processing of the polypeptide or polyprotein resulting in two discontinuous translation products being derived from a single translation event of a single open reading frame. Typically, such self-processing is effected by a "ribosomal skip" caused by a pseudo stop-codon sequence that induces the translation complex to move from one codon to the next without forming a peptide bond. Examples of sequences inducing a ribosomal skip include but are not limited to viral 2A peptides or 2A-like peptide (herein both are collectively referred to as "2A peptide" or interchangeably as "2A site" or "2A cleavage site") which are used by several families of viruses, including Picornavirus, insect viruses, Aphtoviridae, Rotaviruses and Trypanosoma. Best known are 2A sites of rhinovirus and foot-and-mouth disease virus of the Picornaviridae family which are typically used for producing multiple polypeptides from a single ORF.

Accordingly, the term "self-cleavage site" as used herein refers to a cleavage site within the amino acid or nucleotide sequence where this sequence is cleaved or is cleavable without such cleavage involving any additional molecule or where the peptide- or phosphodiester-bond formation in this sequence is prevented in the first place (e.g. through co-translational self-processing as described above).

It is understood that cleavage sites typically comprise several amino acids or are encoded by several codons (e.g. in those cases, wherein the "cleavage site" is not translated into protein but leads to an interruption of translation). Thus, the cleavage site may also serve the purpose of a peptide linker, i.e. sterically separates two peptides. Thus, in some embodiments a "cleavage site" is both a peptide linker and provides above described cleavage function. In this embodiment the cleavage site may encompass additional N- and/or C-terminal amino acids.

The terms "hydrophil" or "hydrophillic" as used herein refers to the capacity of a molecular entity or of a substituent to interact with polar solvents, in particular with water, or with other polar groups (PAC, 1994, 66, 1077. Glossary of terms used in physical organic chemistry (IUPAC Recommendations 1994)). Typically, hydrophilic molecules dissolve well in water or other polar solvents. In contrast, the term "hydrophob" as used herein refers to a molecule or part of a molecule which is not attracted by water or does not interact with water. Hydrophobic molecules tend to be non-polar and, thus, prefer other neutral molecules and non-polar solvents, and often cluster together in water, forming micelles.

"Hydrophobicity scales" are values which define relative hydrophobicity of amino acid residues. The more positive the value, the more hydrophobic is the respective amino acids. There are marked differences between the different hydrophobicity scales due to the different methods used to measure hydrophobicity. Both, the Rose et al. scale [G. Rose, A. Geselowitz, G. Lesser, R. Lee and M. Zehfus, Science 229 (1985) 834-838] and the Janin scale [J. Janin, Nature, 277 (1979) 491-492] place cysteine as the most hydrophobic residue as both examine proteins with known 3-D structures and define the hydrophobic character as the tendency for a residue to be found inside of a protein rather than on its surface (since cysteine forms disulfide bonds that must occur inside a globular structure, cysteine is ranked as the most hydrophobic). The Kyte and Doolittle scale [Kyte, J. and Doolittle, R. F. (1982) A simple method for displaying the hydropathic character of a protein. J. Mol. Biol. 157, 105-132] as well as the Wolfenden scale [R. Wolfenden, L. Andersson, P. Cullis and C. Southgate, Biochemistry 20 (1981) 849-855] are derived from the physiochemical properties of the amino acid side chains. These scales result mainly from inspection of the amino acid structures. According to Kyte-Doolittle individual amino acids exhibit the following hydropathy values

| | |
|---|---|
| Alanine | 1.8 |
| Arginine | −4.5 |
| Asparagine | −3.5 |
| Aspartic acid | −3.5 |
| Cysteine | 2.5 |
| Glutamine | −3.5 |
| Glutamic acid | −3.5 |
| Glycine | −0.4 |
| Histidine | −3.2 |
| Isoleucine | 4.5 |

-continued

| | |
|---|---|
| Leucine | 3.8 |
| Lysine | −3.9 |
| Methionine | 1.9 |
| Phenylalanine | 2.8 |
| Proline | −1.6 |
| Serine | −0.8 |
| Threonine | −0.7 |
| Tryptophan | −0.9 |
| Tyrosine | −1.3 |
| Valine | 4.2 |

The "GRAVY (grand average of hydropathy) value" is one value of expressing the hydrophobicity of a polypeptide or protein and is defined by the sum of hydropathy values of all amino acids divided by the protein length. The calculation of the GRAVY value is based on the Kyte-Doolittle scale. An increasing positive score indicates greater hydrophobicity.

As used herein, the term "vector" refers to a protein or a polynucleotide or a mixture thereof which is capable of being introduced or of introducing the proteins and/or nucleic acid comprised therein into a cell. In the context of the present invention it is preferred that the genes of interest encoded by the introduced polynucleotide are expressed within the cell upon introduction of the vector or vectors. Examples of suitable vectors include but are not limited to plasmids, cosmids, phages, viruses or artificial chromosomes. A vector comprising one or more polynucleotides encoding for one or more gene products of interest may comprise further expression control sequences. In a vector comprising more than one polynucleotide encoding for one or more gene products of interest, the expression may be controlled together or separately by one or more expression control sequences. More specifically, each polynucleotide comprised on the vector may be control by a separate expression control sequence or all polynucleotides comprised on the vector may be controlled by a single expression control sequence. Polynucleotides comprised on a single vector controlled by a single expression control sequences preferably form an open reading frame.

The term "host cell" as used herein refers to a cell that harbours a vector (e.g. a plasmid or virus). A host cell may be a prokaryotic (e.g. a bacterial cell) or an eukaryotic cell (e.g. a fungal, insect, or mammal cell). Bacterial cells include but are not limited to *Escherichia coli* (*E. coli*) cells, such as e.g. *E. coli* BL21 or *E. coli* K12.

The term "buffer" or "buffer solution" as used herein, refers to an aqueous solution consisting of a mixture of a weak acid and its conjugate base, or vice versa. Its pH changes very little when a small or moderate amount of strong acid or base is added to it and thus it is used to prevent changes in the pH of a solution. Buffer solutions are used as a means of keeping pH at a nearly constant value in a wide variety of applications. For buffers in acid regions, the pH may be adjusted to a desired value by adding a strong acid such as hydrochloric acid to the buffering agent. For alkaline buffers, a strong base such as sodium hydroxide may be added. Alternatively, a buffer mixture can be made from a mixture of an acid and its conjugate base. For example, an acetate buffer can be made from a mixture of acetic acid and sodium acetate. Similarly an alkaline buffer can be made from a mixture of the base and its conjugate acid. Examples of buffers include but are not limited to phosphate buffer (e.g. PBS), citrate buffer (e.g. SSC), histidine buffer, APS, Bicine, Tris, Tricine, TAPSO, HEPES, TES, MOPS, PIPES, Cacodylate, MES, Succinic acid buffer.

Phosphate-buffered saline (abbreviated PBS) is a buffer solution commonly used in biological research. It is a water-based salt solution containing sodium phosphate, sodium chloride and, in some formulations, potassium chloride and potassium phosphate. The osmolarity and ion concentrations of the solutions match those of the human body (isotonic).

In citrate buffer solutions, including the commonly used SSC buffer, sodium citrate and sodium chloride are used to maintain a neutral pH 7.0.

The term "joint" as used herein, refers to a location where two or more bones make contact. The term may refer to a movable joint or an unmovable joint. Further, a joint may be a fibrous joint wherein the bones are attached by dense connective tissue rich in collagen or a cartilaginous joint wherein the bones are connected by cartilage. A joint may also be a synovial joint wherein the bones are not directly connected but have a synovial cavity and are attached by a capsule of articular cartilage which is associated with accessory ligaments and tendons. Synovial joints include but are not limited to ball-and-socket-joints, such as the hip or shoulder joints; ellipsoid joints and flat joints, such as the joints of the wrist; hinge joints, such as elbows, knees, ankles or the joints of fingers and toes; saddle joints such as the joint of the thumb; and pivot joint, such as the joint of atlas and axis.

The terms "tissue status", "status of a tissue", "tissue state" and "state of a tissue" are used interchangeably herein referring to the condition of a tissue. The state of a tissue may be characterised by a specific morphology of such tissue or may be characterised by the expression of one or more specific molecules such as but not limited to peptides, proteins, and nucleic acids, or combinations thereof. The status of a tissue may be regarded as "healthy" or "normal" in case it resembles the condition of such tissue when being free from illness or injury and efficiently fulfilling its specific function. The status of a tissue may be regarded as "degenerative", "diseased" or "abnormal" in case such tissue fails to fulfil its function due to an illness or injury. Additionally or alternatively, the status of a tissue may be regarded as "degenerative", "diseased" or "abnormal" in case the morphology of the tissue or its molecule expression pattern is "altered" or "changed" in comparison to normal tissue. Accordingly, the morphology of a tissue or the expression pattern of specific molecules in a tissue may be an indicator for the state of a tissue. Examples of a tissues status include but are not limited to tissue degradation such as cartilage degradation, bone degradation, and degradation of the synovium, tissue inflammation such as cartilage inflammation, or inflammation of the synovium, tissue remodelling such as bone remodelling or cartilage remodelling, sclerosis, liquid accumulation, or proliferative tissue such as proliferation in wound healing processes, cyst formations, or in cancer.

The term "reference sample" as used herein, refers to a sample which is analysed in a substantially identical manner as the sample of interest and whose information is compared to that of the sample of interest. A reference sample thereby provides a standard allowing for the evaluation of the information obtained from the sample of interest. A reference sample may be identical to the sample of interest except for one component which may be exchanged, missing or added. Exemplified, in the context of the present invention, a reference sample may comprise no aggrecan binding moiety or a different aggrecan binding moiety than the sample of interest.

The term "reference value" as used herein, refers to a value which is known to be indicative for a certain status. In the context of the present invention, the reference value may represent the degree of degradation known to be present in a sample lacking an aggrecan binding moiety. Alternatively, the reference value may represent the binding activity a previously known, different aggrecan binding moiety may exhibit. Alternatively, a reference value may represent the alteration of the binding activity of degree of degradation in the presence of absence of an antigen binding moiety. In the context of the present invention, the reference value may be the binding activity CD-RAP exhibits for aggrecan. Alternatively, the reference value may be the alteration in the degree of aggrecan degradation in the presence of CD-RAP.

The terms "lowered" or "decreased" level of protein refer to the level of such protein in the sample being reduced in comparison to the reference or reference sample. The terms "elevated" or "increased" level of a protein refers to the level of such protein in the sample being higher in comparison to the reference or reference sample.

The term "disorder" refers to an abnormal condition, especially an abnormal medical condition such as a disease or injury, wherein a tissue, an organ or an individual is not able to efficiently fulfil its function anymore.

Typically an "injury" refers to the damage to a tissue, an organ or an individual which is caused by physical harm. Examples of an injury include but are not limited to traumatic injury, repetitive strain injury, radiation injury, poisoning, burn or frostbite injury, injury from toxin or from adverse effect of a pharmaceutical drug (e.g. vaccine injury), and reperfusion injury. Depending on the tissue or organ affected the injury may also be classified accordingly, such as e.g. cartilage injury, bone injury, or joint injury.

The term "disease" refers to an abnormal physiological condition. Examples of a disease include but are not limited to inflammatory diseases, infectious diseases, genetic disorders, autoimmune diseases, degenerative disorders, and proliferative disorders (e.g. various types of cancer). In a patient a disease may affect a single or several different tissues and/or organs. Depending on the tissue or organ affected the disease may also be classified accordingly, such as e.g. cartilage disease, bone disease, or joint diseases.

Typically, but not necessarily, a disease or injury is associated with specific "symptoms" or "signs" indicating the presence of such disease or injury. The presence of such symptoms or signs may thus, be indicative for a tissue, an organ or an individual suffering from a disease or injury. An alteration of these symptoms or signs may be indicative for the progression of such a disease or injury. A progression of a disease or injury is typically characterised by an increase or decrease of such symptoms or signs which may indicate a "worsening" or "bettering" of the disease or injury. The "worsening" of a disease or injury is characterised by a decreasing ability of a tissue, organ or organism to fulfil its function efficiently, whereas the "bettering" of a disease or injury is typically characterised by an increase in the ability of a tissue, an organ or an individual to fulfil its function efficiently. A tissue, an organ or an individual being at "risk of developing" a disease or injury is in a healthy state but shows potential of a disease or injury emerging. Typically, the risk of developing a disease or injury is associated with early or weak signs or symptoms of such disease. In such case, the onset and/or progression of the disease or injury may still be prevented by treatment.

The term "joint injury" refers to the physical damage of the joints, in particular to traumatic injury, repetitive strain injury, radiation injury, poisoning, burn or frostbite injury, injury from toxin or from adverse effect of a pharmaceutical drug (e.g. vaccine injury), and reperfusion injury of the joint The term "joint disease" as used herein, refers to the abnormal physiological condition of the joints, in particular those due to degenerative, inflammatory, infectious or autoimmune causes. Joint diseases include but are not limited to arthritis, such as rheumatoid arthritis (RA), ankylosing spondylitis (AS), juvenile idiopathic arthritis (JIA), gout, septic arthritis, psoriatic arthritis, and osteoarthritis (OA), cancer, such as chondrosarcoma, osteosarcoma, fibrosarcoma, and multiple myeloma, tendinitis, bursitis, fractures, and damage to cartilage or bone. A joint disease may develop from an initial joint injury.

Osteoarthritis can be viewed as the clinical and pathological outcome of a range of disorders that result in structural and functional failure of synovial joints. It occurs when the dynamic equilibrium between the breakdown and the repair of joint tissues is overwhelmed. Structural failure of articular cartilage can result from abnormal mechanical strains injuring healthy cartilage, as well as from failure of pathologically impaired cartilage degenerating under the influence of physiological and mechanical strains. OA is characterised by a progressive degeneration of the articular cartilage, ultimately leading to a functional inability of the affected joint. During the chronical progression of OA the articular cartilage is destroyed setting free the underlying bone tissue, ultimately necessitating the surgical replacement of the affected joint. Besides the destruction of the cartilage, pathological degenerations of the synovial membranes and the ligaments are taking place. Inflammation takes place in OA as a secondary effect. Morphological changes observed in OA include cartilage erosion as well as a variable degree of synovial inflammation. These changes are attributed to a complex network of biochemical factors, including proteolytic enzymes that lead to a breakdown of the cartilage macromolecules, in particular collagen II, X and aggrecan. Cytokines such as IL-1 and TNF-α which are produced by activated synoviocytes, mononuclear cells or by articular cartilage itself, significantly up regulate matrix-metalloproteinases (MMPs) and cytokine gene expression, and blunt compensatory synthesis pathways. The exact etiology of OA is still not resolved, but some contributing factors are associated with the onset and progression of the disease. The most important factor is age, but also periodic overload, obesity, joint laxity, and a genetic predisposition play an important role. The degradation of cartilage matrix components is generally agreed to be due to an increased synthesis and activation of extracellular proteinases, and cytokines amplifying degenerative processes. Diagnosis of OA is commonly based on clinical examination of the joints in patients showing a gradual onset of symptoms and signs, with x-rays confirming the diagnosis. Typical changes observable via x-ray include a narrowing of the joint space, marginal osteophytes, subchondral sclerosis, subchondral cyst formation, bony remodelling, and joint effusions.

"Symptoms" of a disease are implication of the disease noticeable by the tissue, organ or organism having such disease and include but are not limited to pain, weakness, tenderness, strain, stiffness, and spasm of the tissue, an organ or an individual. "Signs" or "signals" of a disease include but are not limited to the change or alteration such as the presence, absence, increase or elevation, decrease or decline, of specific indicators such as biomarkers or molecular markers, or the development, presence, or worsening of symptoms. Symptoms of pain include, but are not limited to an unpleasant sensation that may be felt as a persistent or varying burning, throbbing, itching or stinging ache.

The term "indicator" as used herein, refers to a sign or signal for a condition or is used to monitor a condition. Such a "condition" refers to the biological status of a cell, tissue or organ or to the health and/or disease status of an individual. An indicator may be the presence or absence of a molecule, including but not limited to peptide, protein, and nucleic acid, or may be a change in the expression level or pattern of such molecule in a cell, or tissue, organ or individual. An indicator may be a sign for the onset, development or presence of a disease in an individual or for the further progression of such disease. An indicator may also be a sign for the risk of developing a disease in an individual. For instance, known indicators relating to arthritic diseases such as OA include but are not limited to transcription factors such as Sox-5, Sox-6, Sox-9, Nfat1, pitx1, FoxO, HIF2A, SAF-1, RUNX-2, cytokines such as IL-1p, IL-2, IL-7, IL-12, IL-18, GM-CFS, TNF-α, NF-κB, and INF-γ, phosphatases such as Alkaline Phosphatase (ALP), proteases such as metalloproteases (e.g. MMP-1, MMP-2, MMP-3, MMP-8, MMP-9, MMP-13, MMP-14), aggrecanases (e.g. ADAM-8, ADAM-12, ADAM-TS4, ADAM-TS5) and cysteinproteasen (e.g. cathepsin B, cathepsin K, cathepsin S, calpain, caspases-3, caspase-9), tissue inhibitors of metalloproteinases (e.g. TIMP-1, TIMP-2, TIMP-3, TIMP-4), extracellular matrix components, such as collagens (e.g. collagen II, VI, IX, X, XI), proteoglycans (e.g. heparan sulfate, chondroitin sulfate, keratan sulfate), aggrecan, elastin, hyaluronic acid, fibronectin, laminin, CDMPs, chondromodulin and pleiotrophin. Typically, in a tissue, organ, or individual suffering from arthritis, in particular OA, one or more of these indicators are expressed or activated to a higher or lower level than in a tissue, organ, or individual not suffering from arthritis. For instance, it is known that the levels of the extracellular matrix components collagen II and X, as well as aggrecan are lowered in a tissue, organ, or individual suffering or at risk of developing OA in comparison a tissue, organ, or individual not suffering or at risk of developing OA. It is further known that the level of the transcription factor Sox9 as well as the tissue inhibitors of metalloproteinases TIMP-1 and TIMP-4 are decreased in a tissue, organ, or individual suffering or at risk of developing OA in comparison a tissue, organ, or individual not suffering or at risk of developing OA. In contrast, the levels of the cytokine IL-1, IL-6 and TNF-α as well as of the metalloproteases MMP-1, MMP-2, MMP-3 and MMP-9, and phosphatase ALP are known to be enhanced in a tissue, organ, or individual suffering or at risk of developing OA in comparison a tissue, organ, or individual not suffering or at risk of developing OA. The terms "lowered" or "decreased" level of an indicator refer to the level of such indicator in the sample being reduced in comparison to the reference or reference sample. The terms "elevated" or "increased" level of an indicator refer to the level of such indicator in the sample being higher in comparison to the reference or reference sample.

As used herein, "treat", "treating" or "treatment" of a disease or injury means accomplishing one or more of the following: (a) reducing the severity of the disease or injury; (b) limiting or preventing development of symptoms characteristic of the disease or injury being treated; (c) inhibiting worsening of symptoms characteristic of the disease or injury being treated; (d) limiting or preventing recurrence of the disease or injury in an individual who has previously had the disease or injury; and (e) limiting or preventing recurrence of symptoms in individuals who were previously symptomatic for the disease or injury.

As used herein, "prevent", "preventing", "prevention", or "prophylaxis" of a disease or injury means preventing that such disease or injury occurs in patient.

The terms "pharmaceutical", "pharmaceutical composition", "medicament" and "drug" are used interchangeably herein referring to a substance and/or a combination of substances being used for the identification, prevention or treatment of a disease or injury.

As used herein, "administering" includes in vivo administration, as well as administration directly to tissue ex vivo, such as vein grafts. Administration includes but is not limited to intra-articular injection, i.e. application of the drug into the knee, the hip, the carpo-metacarpal joint, the metacarpo-phalangeal joint, shoulder or any other joint affected by disease or injury. Also included is the fluoroscopically guided (by x-ray or by computer-tomography) injection into vertebral discs.

An "effective amount" or "therapeutically effective amount" is an amount of a therapeutic agent sufficient to achieve the intended purpose. The effective amount of a given therapeutic agent will vary with factors such as the nature of the agent, the route of administration, the size and species of the animal to receive the therapeutic agent, and the purpose of the administration. The effective amount in each individual case may be determined empirically by a skilled artisan according to established methods in the art.

"Pharmaceutically acceptable" means approved by a regulatory agency of the Federal or a state government or listed in the U.S. Pharmacopeia or other generally recognized pharmacopeia for use in animals, and more particularly in humans.

The term "active ingredient" refers to the substance in a pharmaceutical composition or formulation that is biologically active, i.e. that provides pharmaceutical value. A pharmaceutical composition may comprise one or more active ingredients which may act in conjunction with or independently of each other. The active ingredient can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as but not limited to those derived from sodium, potassium, ammonium, calcium, ferric hydroxides, isopropylamine, triethylamine, 2-ethylamino ethanol, histidine, procaine, and the like.

The terms "preparation" and "composition" are intended to include the formulation of the active compound with encapsulating material as a carrier providing a capsule in which the active component with or without other carriers, is surrounded by a carrier, which is thus in association with it.

The term "carrier", as used herein, refers to a pharmacologically inactive substance such as but not limited to a diluent, excipient, or vehicle with which the therapeutically active ingredient is administered. Such pharmaceutical carriers can be liquid or solid. Liquid carrier include but are not limited to sterile liquids, such as saline solutions in water and oils, including those of petroleum, animal, vegetable or synthetic origin, such as peanut oil, soybean oil, mineral oil, sesame oil and the like. Saline solutions and aqueous dextrose and glycerol solutions can also be employed as liquid carriers, particularly for injectable solutions. A saline solution is a preferred carrier when the pharmaceutical composition is administered intravenously. Examples of suitable pharmaceutical carriers are described in "Remington's Pharmaceutical Sciences" by E. W. Martin.

Suitable pharmaceutical "excipients" include starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like.

The term "adjuvant" refers to agents that augment, stimulate, activate, potentiate, or modulate the therapeutic effect of the active ingredient. Examples of such adjuvants include but are not limited to inorganic adjuvants (e.g. inorganic metal salts such as aluminium phosphate or aluminium hydroxide), organic adjuvants (e.g. saponins or squalene), oil-based adjuvants (e.g. Freund's complete adjuvant and Freund's incomplete adjuvant), cytokines (e.g. IL-1β, IL-2, IL-7, IL-12, IL-18, GM-CFS, and INF-γ) particulate adjuvants (e.g. immuno-stimulatory complexes (ISCOMS), liposomes, or biodegradable microspheres), virosomes, bacterial adjuvants (e.g. monophosphoryl lipid A, or muramyl peptides), synthetic adjuvants (e.g. non-ionic block copolymers, muramyl peptide analogues, or synthetic lipid A), or synthetic polynucleotides adjuvants (e.g polyarginine or polylysine).

As used herein, a "patient" means any mammal, reptile or bird that may benefit from the present invention. Preferably, a patient is selected from the group consisting of laboratory animals (e.g. mouse, rat or rabbit), domestic animals (including e.g. guinea pig, rabbit, horse, donkey, cow, sheep, goat, pig, chicken, duck, camel, cat, dog, turtle, tortoise, snake, or lizard), or primates including chimpanzees, bonobos, gorillas and human beings. It is particularly preferred that the "patient" is a human being.

EMBODIMENTS

It was found that fermentation yield and especially the folding is significant increased if CD-RAP is expressed with a pre-sequence. In addition to the presence of the pre-sequence as such, harvested amount of pre-CD-RAP gets higher with increasing length of the pre-sequence. The same was found for the amount of folded Pre-CD-RAP obtained after successful folding of this protein.

Accordingly, in a first aspect, the present invention relates to a CD-RAP precursor protein comprising
  a) a pre-sequence, which comprises at its C-terminus a cleavage site, and
  b) CD-RAP or a variant thereof.

In particular embodiments, CD-RAP is human CD-RAP. In further embodiments, CD-RAP has an amino acid sequence according to SEQ ID NO: 1 or a variant thereof. In particular embodiments said variant has a sequence identity of at least 80%, i.e. least 80%, least 81%, least 82%, least 83%, least 84%, least 85%, least 86%, least 87%, least 88%, least 89%, least 90%, least 91%, least 92%, least 93%, least 94%, least 95%, least 96%, least 97%, least 98%, or least 99% sequence identity.

In particular embodiments, the pre-sequence does not disturb the folding of CD-RAP. Accordingly, the pre-sequence does not need to be removed prior to folding. In particular embodiments, the pre-sequence improves the folding of CD-RAP. In further embodiments, the CD-RAP precursor protein may be folded without the presence (i.e. in the absence) of chemical or enzymatical chaperons. In further embodiments, CD-RAP is present in a primary, secondary, or tertiary structure.

In particular embodiments, the pre-sequence has a length of 5-50 amino acids, i.e. 5, 6, 7, 8, 9, 10, 11, 12, 13, 14, 15, 20, 25, 30, 35, 40, 45, or 50 amino acids. In particular embodiments, the pre-sequence has a length of 5-40, 6-35, 7-33, 8-30, 9-25, 10-20, or amino acids.

In particular embodiments of the first aspect, the pre-sequence has a lower grand average of hydropathy than CD-RAP.

In particular embodiments, the pre-sequence has a grand average of hydropathy (GRAVY) of less than −0.2 according to Kyte and Doolittle. In particular embodiments, the pre-sequence has a grand average of hydropathy (GRAVY) of between −0.2 to −1.7, in particular between −0.5 to −1.7, in particular between −0.6 to −1.7, in particular between −0.7 to −1.7, in particular between −0.8 to −1.7. In particular, the pre-sequence has a grand average of hydropathy (GRAVY) of less than −0.2, −0.3, −0.4, −0.5, −0.6, −0.7, −0.8, −0.9, −1.0, −1.2, 1.3, −1.4, 1.5, −1.6, or −1.7.

In particular embodiments, the precursor protein has a grand average of hydropathy (GRAVY) of less than −0.03 according to Kyte and Doolittle. In particular embodiments, the precursor protein has a grand average of hydropathy (GRAVY) of between −0.03 to −0.3. In particular, the precursor protein has a grand average of hydropathy (GRAVY) of less than −0.3, −0.2, −0.1, −0.09, −0.08, −0.07, −0.06, −0.05, −0.04, or −0.03.

In embodiments of the first aspect, the cleavage site of the pre-sequence is an enzymatic cleavage site. In particular embodiments, the cleavage site is an endopeptidase cleavage site, more particular the cleavage site is an enterokinase or a protease of mixed nucleophile, superfamily A (PA clan) cleavage site. In particular embodiments, the cleavage site is an R or K amino acid.

In further embodiments, the endopeptidase is selected from the group consisting of cysteine protease and serine protease. In particular embodiments, the endopeptidase is trypsin or chymotrypsin, in particular trypsin.

In particular embodiments, the pre-sequence comprises an affinity tag. In particular embodiments the affinity tag is a poly-His tag.

In particular embodiments, the pre-sequence comprises at its N-terminus the amino acids MATTX$_1$T, MATTX$_1$TG, MATTX$_1$TGN, MATTX$_1$TGNS or MATTX$_1$TGNSA, wherein X$_1$ is L or S. Accordingly, in particular embodiments, the pre-sequence comprises at its N-terminus an amino acids sequence is selected from the group consisting of MATTST (SEQ ID NO: 2), MATTLT (SEQ ID NO: 3), MATTSTG (SEQ ID NO: 4), MATTLTG (SEQ ID NO: 5), MATTSTGN (SEQ ID NO: 6), MATTLTGN (SEQ ID NO: 7), MATTSTGNS (SEQ ID NO: 8), MATTLTGNS (SEQ ID NO: 9), MATTSTGNSA (SEQ ID NO: 10), MATTLTGNSA (SEQ ID NO: 11), MATTSTR (SEQ ID NO: 12), MATTLTR (SEQ ID NO: 13), MATTSTGNSAR (SEQ ID NO: 14), MATTLTGNSAR (SEQ ID NO: 15), MATTSTLTTHWH-WHGNSAR (SEQ ID NO: 16), MATTSTGNSAHFQHH-HGSLAR (SEQ ID NO: 17), MATTSTGNSAHFQHHHG-SLAR (SEQ ID NO: 18), and MATTSTGNSARFVNQHLH HHHHHHHGGGENQQQR (SEQ ID NO: 19).

In particular embodiments, the pre-sequence comprises at its N-terminus the amino acids MATTST, MATTSTG, MATTSTGN, MATTSTGNS or MATTSTGNSA, or a variant thereof, and at its C-terminus a cleavage site. In particular embodiments, the pre-sequence comprises at its N-terminus the amino acids 1-6, 1-7, 1-8, 1-9, 1-10, 1-11, 1-12, 1-13, 1-14, 1-15, or 1-16 of the amino acid sequence of SEQ ID NO: 19 or a variant thereof, and at its C-terminus a cleavage site. In particular embodiments, the pre-sequence comprises at its N-terminus the amino acids MATTST-GNSA, and at its C-terminus a cleavage site. In further embodiments, the pre-sequence comprises at its N-terminus the amino acids MATTSTGNSARFVNQHL, and at its C-terminus a cleavage site.

In particular embodiments, the amino acid sequence of the pre-sequence comprises or consists of the amino acid sequence of SEQ ID NO: 19 (MATTSTGNSARFVNQHL-HHHHHHHHGGGENQQQR) or a variant thereof.

In particular embodiments, the precursor protein has an amino acid sequence according to SEQ ID NO: 20 or a variant thereof.

In a second aspect, the present invention relates to a nucleic acid encoding the precursor CD-RAP protein of the first aspect of the invention as described in detail above.

In a third aspect, the present invention relates to a vector comprising the nucleic acid the second aspect of the present invention.

In particular embodiments, the vector is a plasmids, viruses, cosmids, phages, bacterial spores, or artificial chromosomes. In particular embodiments, the vector is a plasmid.

In further embodiments of the third aspect, the vector further comprises a nucleic acid encoding a resistance gene, in particular the resistance to ampicillin, neomycin, kanamycin, streptomycin, gentamycin or G 418.

In particular embodiments of the third aspect of the present invention, the vector further comprises regulatory elements. In particular embodiments, the regulatory elements are selected from the group consisting of promoter, enhance, and silencer. In particular embodiments, the promoter is a constitutive promoter or an inducible promoters. In particular embodiments, the promoter is a T7 promoter.

In particular embodiments, the plasmid is a pET-plasmid, in particular a pET-52b-II plasmid.

In a fourth aspect, the present invention relates to a host cell comprising the precursor CD-RAP protein of the first aspect, the nucleic acid of the second aspect, or the vector of the third aspect.

In particular embodiments, the host cell is a prokaryotic cells or eukaryotic cells.

In particular embodiments, the prokaryotic cell is a bacterial cell, in particular an *Escherichia coli* (*E. coli*) cell. In particular embodiments the *E. coli* cell is cell of *E-coli* strain BL21 or K12.

In particular embodiments, the eukaryotic cell is a fungal cell, insect cell or mammal cell. In particular embodiments the fungal cell is a yeast cell, in particular *Kluyveromyces lactis* (*K. lactis*).

In a fifth aspect, the present invention relates to a method of producing native CD-RAP comprising the steps
a) providing a CD-RAP precursor protein comprising
   a) a pre-sequence, which comprises at its C-terminus a cleavage site, and
   b) CD-RAP or a variant thereof, and
b) removing the pre-sequence to obtain native CD-RAP.

In particular embodiments, the CD-RAP precursor protein may be in primary, secondary, or tertiary conformation.

In particular embodiments, the method of the fifth aspect of the invention further comprises one or more of the following steps:
c) folding the CD-RAP precursor protein, and optionally purifying the folded CD-RAP, and
d) purifying the native CD-RAP.

In embodiments of the fifth aspect of the present invention, CD-RAP is folded in step c) prior or subsequent to the removal of the pre-sequence in step b). In particular embodiments, step c) is carried out subsequently to step a) and before step b). Accordingly, in particular embodiments, the pre-sequence is removed subsequent to the folding of CD-RAP, i.e. CD-RAP is folded prior to the removal of the pre-sequence.

In particular, in embodiments, wherein the CD-RAP precursor protein is provided in step a) in the primary or secondary conformation, CD-RAP is folded in step c) prior to the removal of the pre-sequence in step b).

In particular, in embodiments, wherein the CD-RAP precursor protein is provided in step a) in tertiary conformation, folding step c) is not required to obtain native CD-RAP. In embodiments of the fifth aspect of the present invention, the precursor CD-RAP is provided in step a) via biotechnological means. In particular embodiments, the precursor CD-RAP provided by isolation from a host cell of the fourth aspect.

In particular embodiments, CD-RAP is human CD-RAP. In further embodiments, CD-RAP has an amino acid sequence according to SEQ ID NO: 1 or a variant thereof. In particular embodiments said variant has a sequence identity of at least 80%, i.e. least 80%, least 81%, least 82%, least 83%, least 84%, least 85%, least 86%, least 87%, least 88%, least 89%, least 90%, least 91%, least 92%, least 93%, least 94%, least 95%, least 96%, least 97%, least 98%, or least 99% sequence identity.

In particular embodiments, the pre-sequence has a length of 5-50 amino acids, i.e. 5, 6, 7, 8, 9, 10, 11, 12, 13, 14, 15, 20, 25, 30, 35, 40, 45, or 50 amino acids. In particular embodiments the pre-sequence has a length of 5-40, 6-35, 7-33, 8-30, 9-25, or 10-20 amino acids.

In particular embodiments of the fifth aspect, the pre-sequence has a lower grand average of hydropathy (GRAVY) than CD-RAP.

In particular embodiments, the pre-sequence has a grand average of hydropathy (GRAVY) of less than −0.2 according to Kyte and Doolittle. In particular embodiments, the pre-sequence has a grand average of hydropathy (GRAVY) of between −0.2 to −1.7, in particular between −0.5 to −1.7, in particular between −0.6 to −1.7, in particular between −0.7 to −1.7, in particular between −0.8 to −1.7. In particular, the pre-sequence has a grand average of hydropathy (GRAVY) of less than −0.2, −0.3, −0.4, −0.5, −0.6, −0.7, −0.8, −0.9, −1.0, −1.2, 1.3, −1.4, 1.5, −1.6, or −1.7.

In particular embodiments, the precursor protein has a grand average of hydropathy (GRAVY) of less than −0.03 according to Kyte and Doolittle. In particular embodiments, the precursor protein has a grand average of hydropathy (GRAVY) of between −0.03 to −0.3. In particular, the precursor protein has a grand average of hydropathy (GRAVY) of less than −0.3, −0.2, −0.1, −0.09, −0.08, −0.07, −0.06, −0.05, −0.04, or −0.03.

In embodiments of the fifth aspect, the cleavage site of the pre-sequence is an enzymatic cleavage site. In particular embodiments, the cleavage site is an endopeptidase cleavage site, more particular the cleavage site is an enterokinase or a protease of mixed nucleophile, superfamily A (PA clan) cleavage site. In particular embodiments, the cleavage site is an R or K amino acid.

In further embodiments, the endopeptidase is selected from the group consisting of cysteine protease and serine protease. In particular embodiments, the endopeptidase is trypsin or chymotrypsin, in particular trypsin.

In particular embodiments, the pre-sequence comprises an affinity tag. In particular embodiments the affinity tag is a poly-His tag.

In particular embodiments, the pre-sequence comprises at its N-terminus the amino acids MATTX$_1$T, MATTX$_1$TG, MATTX$_1$TGN, MATTX$_1$TGNS or MATTX$_1$TGNSA, wherein X$_1$ is L or S. Accordingly, in particular embodiments, the pre-sequence comprises at its N-terminus an amino acids sequence is selected from the group consisting of MATTST (SEQ ID NO: 2), MATTLT (SEQ ID NO: 3), MATTSTG (SEQ ID NO: 4), MATTLTG (SEQ ID NO: 5), MATTSTGN (SEQ ID NO: 6), MATTLTGN (SEQ ID NO: 7), MATTSTGNS (SEQ ID NO: 8), MATTLTGNS (SEQ ID NO: 9), MATTSTGNSA (SEQ ID NO: 10), MATTLTGNSA (SEQ ID NO: 11), MATTSTR (SEQ ID NO: 12), MATTLTR (SEQ ID NO: 13), MATTSTGNSAR (SEQ ID NO: 14), MATTLTGNSAR (SEQ ID NO: 15), MATTSTLTTHWH-WHGNSAR (SEQ ID NO: 16), MATTSTGNSAHFQHH-HGSLAR (SEQ ID NO: 17), MATTSTGNSAHFQHHHG-SLAR (SEQ ID NO: 18), and MATTSTGNSARFVNQHLH HHHHHHHGGGENQQQR (SEQ ID NO: 19).

In particular embodiments, the pre-sequence comprises at its N-terminus the amino acids MATTST, MATTSTG, MATTSTGN, MATTSTGNS or MATTSTGNSA, or a variant thereof, and at its C-terminus a cleavage site. In particular embodiments, the pre-sequence comprises at its N-terminus the amino acids 1-6, 1-7, 1-8, 1-9, 1-10, 1-11, 1-12, 1-13, 1-14, 1-15, or 1-16 of the amino acid sequence of SEQ ID NO: 19 or a variant thereof, and at its C-terminus a cleavage site. In particular embodiments, the pre-sequence comprises at its N-terminus the amino acids MATTST-GNSA, and at its C-terminus a cleavage site. In further embodiments, the pre-sequence comprises at its N-terminus the amino acids MATTSTGNSARFVNQHL, and at its C-terminus a cleavage site.

In particular embodiments, the amino acid sequence of the pre-sequence comprises or consists of the amino acid sequence of SEQ ID NO: 19 (MATTSTGNSARFVNQHL-HHHHHHHGGGENQQQR) or a variant thereof.

In embodiments of the fifth aspect of the present invention, the pre-sequence is removed in step b) via enzymatic cleavage. In particular, the pre-sequence is removed via enterokinase cleavage or via endopeptidase cleavage. In particular embodiments, the pre-sequence is removed in step b) via trypsin cleavage.

In further embodiments of the fifth aspect of the present invention, the ratio between the proteolytic enzyme, in particular trypsin, and the precursor CD-RAP protein in step b) is 1 unit of enzyme per mg of protein.

In further embodiments of the fifth aspect of the present invention, step b) is carried out for 0.5-20 hours, i.e. for 0.5, 1, 1.5, 2, 2.5, 3, 3.5, 4, 4.5, 5, 5.5, 6, 6.5, 7, 7.5, 8, 8.5, 9, 9.5, 10, 11, 12, 13, 14, 15, 16, 17, 18, 19, or 20 hours. In particular embodiments step b) is carried out for less than 16 hours, i.e. for less than 16, less than 15, less than 14, less than 13, less than 12, less than 11, less than 10, less than 9, less than 8, less than 7, less than 6, less than 5, less than 4, less than 3, less than 2, or less than 1 hour. In particular embodiments, step b) is carried out for 0.5-20 hours, for 1-15 hours, for 2-8 hours, or for 4-7 hours.

In further embodiments of the fifth aspect of the present invention, step b) is carried out at a pH between 5 and 9, i.e. at a pH of 5, 6, 7, 8, or 9. In particular embodiments, the pH is between 7.8 and 8.8, in particular at 8.3. In particular embodiments, step b) is carried out at a pH 5 to 9, 6 to 9, 7 to 8.5, 7.5 to 8.5, or 8 to 8.5.

In further embodiments of the fifth aspect of the present invention, step b) is carried out at a temperature of 5-40° C., i.e. at a temperature of 5, 10, 15, 20, 25, 30, 35, or 40° C. In particular embodiments, step b) is carried out at a temperature of 5-40° C., 10-30° C., or 20-25° C.

In further embodiments of the fifth aspect of the present invention, step c) comprises the steps
(i) incubating the precursor CD-RAP protein in a denaturation buffer, and
(ii) adding the solution obtained in step (i) to a folding buffer.

In particular embodiments, the denaturation buffer in step (i) comprises dithiothreitole (DTT). The concentration of DTT will increase with increasing concentration of the precursor CD-RAP protein in solution. In particular embodiments, the denaturation buffer comprises DTT at a concentration of 5-15 mM, i.e. 5, 6, 7, 8, 9, 10, 11, 12, 13, 14, or 15 mM, in particular at a concentration of 10 mM. In particular embodiments, the denaturation buffer comprises DTT at a concentration of 5-15 mM, i.e. in a concentration of 6-14, 7-13, 8-12, 9-11 mM.

In particular embodiments, the folding buffer comprises arginine. In particular embodiments, the folding buffer comprises arginine at a concentration of 0.5-1 mol/L, i.e. 0.5, 0.6, 0.7, 0.75, 0.8, 0.9, or 1 mol/L, in particular at a concentration of 0.75 mol/L. In particular embodiments, the folding buffer comprises arginine at a concentration of 0.5-1 mol/L, i.e. 0.55-0.9, 0.6-0.8, 0.7-0.8 mol/L.

In further embodiments, the folding buffer does not comprise any chemical or enzymatical chaperons.

In particular embodiments, the denaturation solution is added in step (ii) slowly to the folding buffer. In particular embodiments, the folding buffer is added in step (ii) over a time frame of 1-3 hours, i.e. 1, 1.1, 1.2, 1.3, 1.4, 1.5, 1.6, 1.7, 1.8, 1.9, 2, 2.1, 2.2, 2.3, 2.4, 2.5, 2.6, 2.7, 2.8, 2.9 or 3 hours. In particular embodiments, the folding buffer is added in step (ii) over a time frame of 1-3 hours, in particular, 2-3 hours.

In particular embodiments, the folding step c) is carried out at a temperature between 5 and 25° C., i.e. at a temperature of 5, 6, 7, 8, 9, 10, 11, 12, 13, 14, 15, 16, 17, 18, 19, 20, 21, 22, 23, 24, or 25° C., in particular at 10° C. In particular embodiments, step c) is carried out at a temperature of 5-25° C., 5-20° C., or 5-15° C.

In particular embodiments of the fifth aspect of the present invention, the folded precursor CD-RAP is purified via chromatography. In particular embodiments, the folded precursor CD-RAP is purified via HIC chromatography or multimodal (MM) chromatography. In particular embodiments, CD-RAP is filtrated prior to the chromatographic purification.

In particular embodiments of the fifth aspect of the present invention, the native CD-RAP is purified via chromatography. In particular embodiments, the native CD-RAP is purified by HIC-chromatography.

In a sixth aspect, the present invention provides a CD-RAP protein preparation comprising a CD-RAP protein having the mature CD-RAP sequence of SEQ ID NO: 1 with a length of 107 amino acids.

In particular embodiments of the sixth aspect of the present invention, the ratio of said CD-RAP (107AA) to any other CD-RAP protein present in the CD-RAP protein preparation is ≥99 wt-%. In particular embodiments, the ratio of said CD-RAP (107AA) to any other CD-RAP protein present in the CD-RAP protein preparation is ≥99.5 wt-% or ≥99.9 wt-%.

In particular embodiments, the CD-RAP protein preparation of the sixth aspect of the present invention is free of CD-RAP (105AA), having the CD-RAP sequence of SEQ ID NO: 21 with a length of 105 amino acids.

As recognized by the present inventors, CD-RAP protein preparations available so far always contained a considerable amount of CD-RAP (105AA) being an N-terminal truncated CD-RAP. The CD-RAP precursor protein disclosed herein now allows for preparation of pure CD-RAP (107AA). A preparation free of CD-RAP (105AA), in particular, means a preparation containing an amount of CD-RAP (105AA) being ≤1 wt %, in particular ≤0.5 wt %, in particular ≤0.1 wt %, in particular ≤0.01 wt %, based on CD-RAP (107AA) protein present in the preparation.

In particular embodiments, the CD-RAP protein preparation has a melting temperature of ≥40° C. In particular embodiments, the CD-RAP protein preparation of the present invention has a melting temperature of ≥40° C., in particular ≥45° C., in particular 48° C., in particular ≥50° C., in particular ≥52° C. Most preferably the CD-RAP protein preparation has a melting temperature of ~54° C., most preferably ~55° C. The melting point is in particular determined using DSF (differential scanning fluorometry) at a CD-RAP concentration of 1.0 mglmL in a 200 mM L-arginine, 50 mM NaH2P04, pH7.5 buffer.

In a seventh aspect, the present invention provides a composition comprising CD-RAP or a variant thereof, or the CD-RAP protein preparation of the sixth aspect as described in detail above, and at least one positively charged amino acid and a buffer.

In particular embodiments, CD-RAP is human CD-RAP, in particular human CD-RAP according to SEQ ID NO: 1 or a variant thereof.

In particular embodiments, said variant has at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% amino acid sequence identity to CD-RAP according to SEQ ID NO: 1.

In particular embodiments, the CD-RAP is the native CD-RAP obtained via the method of the fifth aspect of the present invention as described in detail above.

In embodiments of the seventh aspect of the present invention, the at least one positively charged amino acid increases the stability of CD-RAP, in particular by preventing the degradation, denaturation and/or aggregation of CD-RAP. In particular embodiments, the at least one positively charged amino acid prevents the aggregation of CD-RAP. In particular embodiments the at least one positively charged amino acid is selected from the group consisting of arginine, lysine, and histidine.

In embodiments of the seventh aspect of the present invention, the buffer increases the stability of CD-RAP, in particular by preventing the degradation, denaturation and/or aggregation of CD-RAP. In particular embodiments, the buffer prevents the degradation of CD-RAP. In particular embodiments the buffer is selected from the group consisting of citrate buffer, phosphate buffer, histidine buffer and Tris buffer.

In embodiments the composition of the seventh aspect of the present invention further comprises a sugar or an amino sugar. In particular embodiments, the sugar is a monosaccharide, disaccharide or trisaccharide, in particular selected from the group consisting of sucrose, maltose, trehalose or raffinose. In particular embodiments, the amino sugar is selected from the group consisting of glucosamine, N-methyl-glucosamine, galactosamine or neuraminic acid.

In particular embodiments, the composition of the seventh aspect of the present invention does not comprise ascorbic acid and/or glycine.

In embodiments of the seventh aspect of the present invention, the composition comprises arginine in a concentration of 50-500 mM, i.e. 50, 60, 70, 80, 90, 100, 150, 200, 250, 300, 350, 400, 450, or 500 mM. In embodiments, the composition comprises arginine in a concentration of 100-350 mM. In further embodiments, the composition comprises arginine in a concentration of 100-200 mM. In particular embodiments, the composition comprises arginine in a concentration of 200 mM.

In embodiments of the seventh aspect of the present invention, the composition comprises histidine in a concentration of 5-100 mM, i.e. 5, 6, 7, 8, 9, 10, 20, 25, 30, 35, 40, 45, 60, 65, 70, 75, 80, 85, 90, 95, or 100 mM. In embodiments the composition comprises histidine in a concentration of 10-50 mM. In further embodiments the composition comprises histidine in a concentration of 20-50 mM. In particular embodiments the composition comprises histidine in a concentration of 50 mM.

In embodiments of the seventh aspect of the present invention, the composition comprises a phosphate buffer. In embodiments wherein the composition comprises a phosphate buffer, the composition comprises sodium phosphate in an aqueous solution, in particular in a concentration of 5-100 mM, i.e. 5, 6, 7, 8, 9, 10, 20, 25, 30, 35, 40, 45, 60, 65, 70, 75, 80, 85, 90, 95, or 100 mM. In embodiments the composition comprises sodium phosphate in a concentration of 10-50 mM. In further embodiments the composition comprises sodium phosphate in a concentration of 20-50 mM. In particular embodiments the composition comprises sodium phosphate in a concentration of 20 mM.

In embodiments wherein the composition comprises a phosphate buffer, the composition comprises potassium phosphate in an aqueous solution, in particular in a concentration of 5-100 mM, i.e. 5, 6, 7, 8, 9, 10, 20, 25, 30, 35, 40, 45, 60, 65, 70, 75, 80, 85, 90, 95, or 100 mM. In further embodiments the composition comprises potassium phosphate in a concentration of 20-50 mM. In particular embodiments the composition comprises potassium phosphate in a concentration of 20 mM.

In embodiments of the seventh aspect of the present invention, the composition comprises a citrate buffer. In embodiments wherein the composition comprises a citrate buffer, the composition comprises citrate in an aqueous solution, in particular in a concentration of 5-100 mM, i.e. 5, 6, 7, 8, 9, 10, 20, 25, 30, 35, 40, 45, 60, 65, 70, 75, 80, 85, 90, 95, or 100 mM. In embodiments the composition comprises citrate in a concentration of 10-50 mM. In further embodiments the composition comprises citrate in a concentration of 20-50 mM. In particular embodiments the composition comprises citrate in a concentration of 20 mM.

In embodiments of the seventh aspect of the present invention, the composition further comprises sucrose. In embodiments the composition comprises sucrose in a concentration of 5-100 mM, i.e. 5, 6, 7, 8, 9, 10, 20, 25, 30, 35, 40, 45, 60, 65, 70, 75, 80, 85, 90, 95, or 100 mM. In embodiments the composition comprises citrate in a concentration of 10-50 mM. In further embodiments the composition comprises citrate in a concentration of 20-50 mM. In particular embodiments the composition comprises citrate in a concentration of 45 mM.

In embodiments of the seventh aspect of the present invention, the composition further comprises a negatively charged amino acid. In particular embodiments, the negatively charged amino acid is selected from the group consisting of glutamic acid and aspartic acid. In particular embodiments, the composition comprises a combination of glutamic acid and aspartic acid.

In embodiments, wherein the composition comprises a combination of glutamic acid and aspartic acid, the total concentration of arginine and glutamic acid of 50-500 mM, i.e. 50, 60, 70, 80, 90, 100, 150, 200, 250, 300, 350, 400, 450, or 500 mM. In embodiments, the composition comprises a combination of glutamic acid and aspartic acid in a total concentration of 100-350 mM, in particular of 100-200 mM. In particular embodiments the composition comprises a combination of glutamic acid and aspartic acid in a total concentration of 200 mM.

In embodiments, wherein the composition comprises a combination of arginine and glutamic acid, arginine and glutamic acid are present in a ratio of 1:1. In particular embodiments arginine and glutamic acid are present in a ratio of 1:1.25. In further embodiments arginine and glutamic acid are present in a ratio of particularly 1:1.5. In particular embodiments, arginine and glutamic acid are present in a ratio of 1:2.

In embodiments of the seventh aspect of the present invention, the pH value of the composition is between 5.5 and 8.0, i.e. 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, or 8.0. In embodiments, the pH value of the composition is between 6.0 and 7.5. In further embodiments, the pH value of the composition is between 6.0 and 6.5. In particular embodiments, the pH value of the composition is 6.

In embodiments of the seventh aspect of the present invention, the pH value of the composition is adjusted using phosphoric acid or hydrogen chloride. In particular embodiments, the pH value of the composition is adjusted using phosphoric acid.

In embodiments of the seventh aspect of the present invention, the concentration of CD-RAP or the variant thereof is between 1 and 10 mg/ml, i.e. 1, 2, 3, 4, 5, 6, 7, 8, 9, or 10 mg/ml. In particular embodiments, the concentration of CD-RAP is between 2 and 5 mg/ml.

In particular embodiments of the seventh aspect of the present invention, the composition comprises 2 mg/ml CD-RAP or a variant thereof, 20 mM citrate, and 200 MM arginine, in an aqueous solution and has a pH value of 6.

In an eighth aspect, the present invention provides the CD-RAP protein preparation of the sixth aspect or the composition of the seventh aspect as described in detail above, for use in a method of treating and/or preventing joint disease or injury in patients. In particular embodiments of a joint disease or injury, the cartilage and/or the soft-tissue, is affected. In particular, the joint disease or injury is a cartilage disease or injury and/or a disease or injury of the cruciate ligaments and/or the collateral ligaments. In further embodiments, the cartilage is affected in manner leading to its degradation. The degradation of the cartilage may be caused by various factors. Cartilage degradation may be caused or triggered by an injury such as but not limited to a traumatic injury or a repetitive strain injury (such as e.g. chronic erosion of cartilage tissue due to repetitive activities). The severity of the cartilage degradation may range from grade 1 to grade 4 according to the classification of the International Cartilage Repair Society, i.e. from superficial lesions (grade 1) up to full thickness lesions, reaching bone tissue (grade 4). The area of cartilage degradation includes the area of initial cartilage lesion (i.e. which was caused by the traumatic injury or a repetitive strain injury) as well as cartilage in other areas, i.e. other joints or other part of the same joint, may also be injured after said injury. In further embodiments, bone fractures involving one or more joints may also distort cartilage morphology and, thus in the long run, induce cartilage degeneration.

Additionally or alternatively, cartilage degradation may be caused by disease such as but not limited to an inflammatory diseases, infectious diseases, genetic disorders, autoimmune diseases, degenerative disorders and proliferative disorders, in particular by rheumatoid arthritis, bacterial synovitis, sarcomas of the synovial tissue or of cartilage itself.

In embodiments of the eighth aspect, the CD-RAP protein preparation of the sixth aspect or the composition of the seventh aspect is for use in treating and/or preventing joint disease or injury in patients suffering from cartilage degradation and/or increased influx of water into the cartilage, and/or decreased presence of CD-RAP in the cartilage.

In further embodiments, the cartilage degradation involves the degradation of proteoglycans, in particular of aggrecan. Proteoglycan degradation may occur due to protease cleavage. Proteases involved in the degradation of proteoglycans, preferably of aggrecan, include but are not limited to matrix-metalloproteinases (MMPs), Cathepsins, A Disintegrin And Metalloproteinase (ADAM), and A Disintegrin And Metalloproteinase with Thrombospondin motif (ADAMTS). In preferred embodiments, proteoglycans, preferably aggrecan, are degraded by a protease selected from the group consisting of MMP-1, MMP-3, MMP-2, MMP-7, MMP-8, MMP-9, MMP-13, Cathepsin D, ADAMTS-1, ADAMTS-4, ADAMTS-5, ADAMTS-8, ADAMTS-9, ADAMTS-15, ADAMTS-16, and ADAMTS-18. Particularly preferred are ADAMTS-4 and/or ADAMTS-5.

In further embodiments, the protease cleavage occurs at a cleavage site located between the globular G1 and G2 domain of aggrecan. In further embodiments, the polypeptide chain of aggrecan is cleaved between Asn341-Phe342 and/or between Glu373-Ala374, preferably at the Glu373-Ala374 peptide bond.

In further embodiments, the CD-RAP protein preparation of the sixth aspect or the composition of the seventh aspect is for use in treating and/or preventing joint disease or injury in patients suffering from aggrecan degradation. In particular embodiments 0.5%-5% of aggrecan are degraded, i.e. 0.5%, 1%, 1.5%, 2%, 2.5%, 3%, 3.5%, 4%, 4.5%, or 5% of aggrecan are degraded. In particular embodiments more than 0.5%, more than 1%, more than 1.5%, more than 2%, more than 2.5%, more than 3%, more than 3.5%, more than 4%, or more than 4.5% of aggrecan are degraded. In particular, the cartilage degradation is measured in comparison to unremarkable, non-diseased cartilage tissue, which typically but not necessarily exhibits a density of proteoglycans equivalent to 65-150 mg/ml, i.e. 65, 70, 75, 80, 85, 90, 95, 100, 110, 120, 130, 140, or 150 mg/ml. Alternatively, unremarkable, non-diseased cartilage tissue typically but not necessarily exhibits a density of proteoglycans equivalent to 400, 450, 500, 550, 600, 650, 700, 750, 800, 850, 900, 950, or 1000 msec in the T1 value visualized by DGEMRIC technique. In particular embodiments, the cartilage degradation results in a proteoglycan density of below 65, below 60, below 55, below 50, below 45, below 40, below 35, below 30, below 25, below 20, below 15, below 10, or below 5 mg/ml. Alternatively, cartilage degradation results in a proteoglycan density of below 400, below 350, below 300, below 250, below 200, below 150, below 100, or below 50 msec in the T1 value visualized by DGEMRIC technique.

Accordingly, in particular embodiments, the CD-RAP protein preparation of the sixth aspect or the composition of the seventh aspect decreases the cartilage degradation to a proteoglycan density above 5, 10, 15, 20, 25, 30, 35, 40, 45, 50, 55, 60, or 65 mg/ml. Alternatively, the composition of the first aspect decreases the cartilage degradation to a proteoglycan density of above 50, 100, 150, 200, 250, 300, 350, or 400 msec in the T1 value visualized by DGEMRIC technique.

The loss of intact proteoglycan, in particular the loss of intact aggrecan, in particular due to aggrecan degradation, i.e. the increase of cleaved proteoglycan, preferably aggrecan, leads to an influx of water into the cartilage and thereby to a swelling of the cartilage and thus the joint. Accordingly, in embodiments of the second aspect, the composition of the first aspect is for use in treating and/or preventing joint disease or injury in patients suffering from an increased influx of water into the cartilage.

CD-RAP interacts with aggrecan and prevents its degradation, in particular its proteolytic degradation. The interaction of CD-RAP with aggrecan prevents proteases such as e.g. matrix-metalloproteinases (MMPs), Cathepsins, A Disintegrin And Metalloproteinase (ADAM), and A Disintegrin And Metalloproteinase with Thrombospondin motif (ADAMTS), preferably selected from the group consisting of MMP-1, MMP-3, MMP-2, MMP-7, MMP-8, MMP-9, MMP-13, Cathepsin D, ADAMTS-1, ADAMTS-4, ADAMTS-5, ADAMTS-8, ADAMTS-9, ADAMTS-15, ADAMTS-16, and ADAMTS-18, from being able to cleave the aggrecan peptide chain. The decreased presence or complete absence of CD-RAP leads to an increased degradation of aggrecan.

Thus, in embodiments of the eighth aspect, the CD-RAP protein preparation of the sixth aspect or the composition of the seventh aspect is for use in treating and/or preventing joint disease or injury in patients suffering from a decreased presence of CD-RAP in the joint. In particular embodiments, the presence of CD-RAP is decreased in the cartilage.

The decreased presence of CD-RAP may be due to a decreased expression of CD-RAP. Alternatively and/or additionally, the presence of CD-RAP may be decreased due to it being retained in the expressing cells, in particular due to it being retained in chondrocytes. Alternatively and/or additionally, the presence of CD-RAP may be decreased due to it being degraded inside the expressing cells, in particular in the chondrocytes, or after it being secreted from the cells into the extracellular space, preferably the cartilage.

In particular embodiments of the eighth aspect, the CD-RAP protein preparation of the sixth aspect or the composition of the seventh aspect is for use in treating and/or preventing joint disease or injury in patients suffering from a decreased expression of CD-RAP, a retention of CD-RAP in the cells, preferably the chondrocytes, or a degradation of CD-RAP in the cells, preferably the chondrocytes, or the extracellular space.

In particular embodiments of the eighth aspect, the CD-RAP protein preparation of the sixth aspect or the composition of the seventh aspect is for use in treating and/or preventing cartilage disease or injury in patients suffering from aggrecan degradation, and/or increased influx of water into the cartilage, and/or decreased CD-RAP presence, wherein the cartilage disease is selected from the group consisting of osteoarthritis (OA), rheumatoid arthritis (RA), chondrodysplasia, chondromalacia, chondrosarcoma, degenerative disk disease, hipdysplasia, asteoarthropathy of the fingers, osteochondritis dissecans, and polychondritis.

In particular embodiments, the osteoarthritis is selected from the group consisting of Kellgren-Lawrence osteoarthritis, ankle osteoarthritis, elbow osteoarthritis, finger osteoarthritis, hip osteoarthritis, knee osteoarthritis, shoulder osteoarthritis, spine osteoarthritis, toe osteoarthritis, wrist osteoarthritis. In particular embodiments, the OA is early onset OA.

In particular embodiments of the eighth aspect, the CD-RAP protein preparation of the sixth aspect or the composition of the seventh aspect is for use in treating and/or preventing cartilage disease or injury in patients suffering from aggrecan degradation, and/or increased influx of water into the cartilage, and/or decreased CD-RAP presence, wherein the cartilage injury is a traumatic injury or a repetitive strain injury (such as e.g. chronic erosion of cartilage tissue due to repetitive activities). The severity of the cartilage degradation may range from grade 1 to grade 4 according to the classification of the International Cartilage Repair Society, i.e. from superficial lesions (grade 1) up to full thickness lesions, reaching bone tissue (grade 4). The area of cartilage degradation includes the area of initial cartilage lesion (i.e. which was caused by the traumatic injury or a repetitive strain injury) as well as cartilage in other areas, i.e. other joints or other part of the same joint, may also be injured after said injury. In further embodiments, bone fractures involving one or more joints may also distort cartilage morphology and, thus in the long run, induce cartilage degeneration.

In embodiments of the eighth aspect, the patient is a mammal, reptile or bird. In particular embodiments, the patient is selected from the group consisting of laboratory animals (e.g. mouse or rat), domestic animals (including e.g. guinea pig, rabbit, horse, donkey, cow, sheep, goat, pig, chicken, camel, cat, dog, turtle, tortoise, snake, or lizard), or primates including chimpanzees, bonobos, gorillas and human beings. Human beings are in particular referred to.

In further embodiments of the eighth aspect, the CD-RAP protein preparation of the sixth aspect or the composition of the seventh aspect alters the degree of cartilage degradation in a patient. In particular embodiments, the composition of the first aspect decreases the degree of cartilage degradation, more preferably the degree of aggrecan degradation, in a patient. In particular, the composition of the first aspect of the present invention decreases the degree of cartilage degradation, preferably the degree of aggrecan degradation, by at least 5%, at least 10%, at least 15%, at least 20%, or at least 25%. In particular embodiments more than 0.5%, more than 1%, more than 1.5%, more than 2%, more than 2.5%, more than 3%, more than 3.5%, more than 4%, or more than 4.5% of aggrecan are degraded. In particular, the cartilage degradation is measured in comparison to unremarkable, non-diseased cartilage tissue, which typically but not necessarily exhibits a density of proteoglycans equivalent to 65-150 mg/ml, i.e. 65, 70, 75, 80, 85, 90, 95, 100, 110, 120, 130, 140, or 150 mg/ml. Alternatively, unremarkable, non-diseased cartilage tissue typically but not necessarily exhibits a density of proteoglycans equivalent to 400, 450, 500, 550, 600, 650, 700, 750, 800, 850, 900, 950, or 1000 msec in the T1 value visualised by DGEMRIC technique. In particular embodiments, the cartilage degradation results in a proteoglycan density of below 65, below 60, below 55, below 50, below 45, below 40, below 35, below 30, below 25, below 20, below 15, below 10, or below 5 mg/ml. Alternatively, cartilage degradation results in a proteoglycan density of below 400, below 350, below 300, below 250, below 200, below 150, below 100, or below 50 msec in the T1 value visualised by DGEMRIC technique.

Accordingly, in particular embodiments, the CD-RAP protein preparation of the sixth aspect or the composition of the seventh aspect decreases the cartilage degradation to a proteoglycan density above 5, 10, 15, 20, 25, 30, 35, 40, 45, 50, 55, 60, or 65 mg/ml. Alternatively, the aggrecan binding moiety decreases the cartilage degradation to a proteoglycan density of above 50, 100, 150, 200, 250, 300, 350, or 400 msec in the T1 value visualised by DGEMRIC technique.

In further embodiments of the sixth, seventh, or eighth aspect of the present invention, the CD-RAP protein preparation or the composition is for intravenous and/or intra-articular administration.

In a ninth aspect, the present invention provides a pharmaceutical comprising the CD-RAP protein preparation of the sixth aspect or the composition of the seventh as described in detail above. In particular embodiments, the pharmaceutical comprising the CD-RAP protein preparation of the sixth aspect or the composition of the seventh aspect as described in detail above, is for use in a method of treating and/or preventing joint disease or injury in patients as detailed above with regard to the eigth aspect of the present invention. In further embodiments of the ninth aspect, the pharmaceutical comprising the CD-RAP protein preparation of the sixth aspect or the composition of the seventh aspect as described in detail above is for intravenous and/or intra-articular administration.

In particular embodiments, the pharmaceutical further comprises a pharmaceutically acceptable carrier and/or excipient and optionally one or more additional active substances.

In particular embodiments, the carrier is liquid. In further embodiments, the liquid carrier include but are not limited to sterile liquids, such as saline solutions in water and oils, including those of petroleum, animal, vegetable or synthetic origin, such as peanut oil, soybean oil, mineral oil, sesame oil and the like. Saline solutions and aqueous dextrose and glycerol solutions can also be employed as liquid carriers, particularly for injectable solutions. A saline solution is a preferred carrier when the pharmaceutical composition is administered intravenously. Examples of suitable pharmaceutical carriers are described in "Remington's Pharmaceutical Sciences" by E. W. Martin.

In further embodiments, the excipients include but are not limited to starch, glucose, lactose, sucrose, gelatin, malt, rice, flour, chalk, silica gel, sodium stearate, glycerol monostearate, talc, sodium chloride, dried skim milk, glycerol, propylene, glycol, water, and ethanol.

In further embodiments, the adjuvant augments, stimulates, activates, potentiates, or modulates the effect of the active ingredient. In particular, the adjuvants is selected from the group consisting of inorganic adjuvants (e.g. inorganic metal salts such as aluminium phosphate or aluminium hydroxide), organic adjuvants (e.g. saponins or squalene), oil-based adjuvants (e.g. Freund's complete adjuvant and Freund's incomplete adjuvant), cytokines (e.g. IL-1p, IL-2, IL-7, IL-12, IL-18, GM-CFS, and INF-γ) particulate adjuvants (e.g. immuno-stimulatory complexes (ISCOMS), liposomes, or biodegradable microspheres), virosomes, bacterial adjuvants (e.g. monophosphoryl lipid A, or muramyl peptides), synthetic adjuvants (e.g. non-ionic block copolymers, muramyl peptide analogues, or synthetic lipid A), and synthetic polynucleotides adjuvants (e.g polyarginine or polylysine).

In embodiments wherein an additional active substance is present it is preferred that said active substance is an active ingredient which provides a pharmaceutical value. In particular, the pharmaceutical composition may comprise one or more active ingredients which may act in conjunction with or independently of each other. The active ingredient can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as but not limited to those derived from sodium, potassium, ammonium, calcium, ferric hydroxides, isopropylamine, triethylamine, 2-ethylamino ethanol, histidine, and procaine.

In particular embodiments, the pharmaceutical further comprising at least one positively charged amino acid and a buffer as described in detail below with respect to the tenth aspect of the present invention.

In a tenth aspect, the present invention provides a method of producing a composition of the seventh or eighth aspect of the present invention, comprising the step of adding CD-RAP or a variant thereof to a buffer comprising at least one positively charged amino acid.

In particular embodiments of the tenth aspect, CD-RAP is human CD-RAP, in particular human CD-RAP according to SEQ ID NO: 1 or a variant thereof.

In particular embodiments, said variant has at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% amino acid sequence identity to CD-RAP according to SEQ ID NO: 1.

In particular embodiments, the CD-RAP is the native CD-RAP obtained via the method of the fifth aspect of the present invention as described in detail above.

In embodiments of the tenth aspect of the present invention, the at least one positively charged amino acid increases the stability of CD-RAP, in particular by preventing the degradation, denaturation and/or aggregation of CD-RAP. In particular embodiments, the at least one positively charged amino acid prevents the aggregation of CD-RAP. In particular embodiments the at least one positively charged amino acid is selected from the group consisting of arginine, lysine, and histidine.

In embodiments of the tenth aspect of the present invention, the buffer increases the stability of CD-RAP, in particular by preventing the degradation, denaturation and/or aggregation of CD-RAP. In particular embodiments, the buffer prevents the degradation of CD-RAP. In particular embodiments the buffer is selected from the group consisting of citrate buffer, phosphate buffer, histidine buffer and Tris buffer.

In embodiments, the composition produced by the tenth aspect of the present invention further comprises a sugar or an amino sugar. Accordingly, the method of the tenth aspect further comprises the step of adding a sugar or an amino sugar. In particular embodiments, the sugar is a monosaccharide, disaccharide or trisaccharide, in particular selected from the group consisting of sucrose, maltose, trehalose or raffinose. In particular embodiments, the amino sugar is selected from the group consisting of glucosamine, N-methyl-glucosamine, galactosamine or neuraminic acid.

In particular embodiments, the composition produced by the tenth aspect of the present invention does not comprise ascorbic acid and/or glycine.

In embodiments of the tenth aspect of the present invention, the composition produced comprises arginine in a concentration of 50-500 mM, i.e. 50, 60, 70, 80, 90, 100, 150, 200, 250, 300, 350, 400, 450, or 500 mM. Accordingly, the method of the tenth aspect comprises the step of adding arginine in a concentration of 50-500 mM, i.e. 50, 60, 70, 80, 90, 100, 150, 200, 250, 300, 350, 400, 450, or 500 mM. In embodiments, the composition produced comprises arginine in a concentration of 100-350 mM. Accordingly, the method of the tenth aspect comprises the step of adding arginine in a concentration of 100-350 mM. In further embodiments, the composition produced comprises arginine in a concentration of 100-200 mM. Accordingly, the method of the tenth aspect comprises the step of adding arginine in a concentration of 100-200 mM. In particular embodiments, the composition produced comprises arginine in a concentration of 200 mM. Accordingly, the method of the tenth aspect comprises the step of adding arginine in a concentration of 200 mM.

In embodiments of the tenth aspect of the present invention, the composition produced comprises histidine in a concentration of 5-100 mM, i.e. 5, 6, 7, 8, 9, 10, 20, 25, 30, 35, 40, 45, 60, 65, 70, 75, 80, 85, 90, 95, or 100 mM. Accordingly, the method of the tenth aspect comprises the step of adding histidine in a concentration of 5-100 mM. In embodiments the composition produced comprises histidine in a concentration of 10-50 mM. Accordingly, the method of the tenth aspect comprises the step of adding histidine in a concentration of 10-50 mM. In further embodiments, the composition produced comprises histidine in a concentration of 20-50 mM. Accordingly, the method of the tenth aspect comprises the step of adding histidine in a concentration of 20-50 mM. In particular embodiments the composition produced comprises histidine in a concentration of 50 mM. Accordingly, the method of the tenth aspect comprises the step of adding histidine in a concentration of 50 mM.

In embodiments of the tenth aspect of the present invention, the composition produced comprises a phosphate buffer. Accordingly, the method of the tenth aspect comprises adding CD-RAP or a variant thereof to a phosphate buffer. In embodiments, wherein the composition produced comprises a phosphate buffer, the composition comprises sodium phosphate in an aqueous solution, in particular in a concentration of 5-100 mM, i.e. 5, 6, 7, 8, 9, 10, 20, 25, 30, 35, 40, 45, 60, 65, 70, 75, 80, 85, 90, 95, or 100 mM. In embodiments the composition produced comprises sodium phosphate in a concentration of 10-50 mM. In further embodiments the composition produced comprises sodium phosphate in a concentration of 20-50 mM. In particular embodiments the composition comprises sodium phosphate in a concentration of 20 mM.

In embodiments wherein the composition produced comprises a phosphate buffer, the composition produced comprises potassium phosphate in an aqueous solution, in particular in a concentration of 5-100 mM, i.e. 5, 6, 7, 8, 9, 10, 20, 25, 30, 35, 40, 45, 60, 65, 70, 75, 80, 85, 90, 95, or 100 mM. In further embodiments the composition comprises potassium phosphate in a concentration of 20-50 mM. In particular embodiments the composition comprises potassium phosphate in a concentration of 20 mM.

In embodiments of the tenth aspect of the present invention, the composition produced comprises a citrate buffer. Accordingly, the method of the tenth aspect comprises adding CD-RAP or a variant thereof to a citrate buffer. In embodiments wherein the composition produced comprises a citrate buffer, the composition produced comprises citrate in an aqueous solution, in particular in a concentration of 5-100 mM, i.e. 5, 6, 7, 8, 9, 10, 20, 25, 30, 35, 40, 45, 60, 65, 70, 75, 80, 85, 90, 95, or 100 mM. In embodiments the composition produced comprises citrate in a concentration of 10-50 mM. In further embodiments the composition produced comprises citrate in a concentration of 20-50 mM. In particular embodiments the composition produced comprises citrate in a concentration of 20 mM.

In embodiments of the tenth aspect of the present invention, the composition produced further comprises sucrose. Accordingly, the method of the tenth aspect comprises the step of adding sucrose. In embodiments the composition produced comprises sucrose in a concentration of 5-100 mM, i.e. 5, 6, 7, 8, 9, 10, 20, 25, 30, 35, 40, 45, 60, 65, 70, 75, 80, 85, 90, 95, or 100 mM. Accordingly, the method of the tenth aspect comprises the step of adding sucrose in a concentration of 5-100 mM. In embodiments the composition produced comprises sucrose in a concentration of 10-50 mM. Accordingly, the method of the tenth aspect comprises the step of adding sucrose in a concentration of 10-50 mM. In further embodiments the composition produced comprises sucrose in a concentration of 20-50 mM. Accordingly, the method of the tenth aspect comprises the step of adding sucrose in a concentration of 20-50 mM. In particular embodiments the composition produced comprises sucrose in a concentration of 45 mM. Accordingly, the method of the tenth aspect comprises the step of adding sucrose in a concentration of 45 mM.

In embodiments of the tenth aspect of the present invention, the composition produced further comprises a negatively charged amino acid. Accordingly, the method of the tenth aspect comprises the step of adding a negatively charged amino acid. In particular embodiments, the negatively charged amino acid is selected from the group consisting of glutamic acid and aspartic acid. In particular embodiments, the composition produced comprises a combination of glutamic acid and aspartic acid.

In embodiments, wherein the composition produced comprises a combination of glutamic acid and aspartic acid, the total concentration of arginine and glutamic acid of 50-500 mM, i.e. 50, 60, 70, 80, 90, 100, 150, 200, 250, 300, 350, 400, 450, or 500 mM. Accordingly, the method of the tenth aspect comprises the step of adding a combination of glutamic acid and aspartic acid in a total concentration of 50-500 mM. In embodiments, the composition produced comprises a combination of glutamic acid and aspartic acid in a total concentration of 100-350 mM, in particular of 100-200 mM. Accordingly, the method of the tenth aspect comprises the step of adding a combination of glutamic acid and aspartic acid in a total concentration of 100-350 mM, in particular of 100-200 mM. In particular embodiments the composition produced comprises a combination of glutamic acid and aspartic acid in a total concentration of 200 mM. Accordingly, the method of the tenth aspect comprises the step of adding a combination of glutamic acid and aspartic acid in a total concentration of 200 mM.

In embodiments, wherein the composition produced comprises a combination of arginine and glutamic acid, arginine and glutamic acid are present in a ratio of 1:1. In particular embodiments arginine and glutamic acid are present in a ratio of 1:1.25. In further embodiments arginine and glutamic acid are present in a ratio of particularly 1:1.5. In particular embodiments, arginine and glutamic acid are present in a ratio of 1:2.

In embodiments of the tenth aspect of the present invention, the pH value of the composition produced is between 5.5 and 8.0, i.e. 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, or 8.0. Accordingly, the method of the tenth aspect comprises the step of adjusting the pH to a value between 5.5 and 8.0. In embodiments, the pH value of the composition is between 6.0 and 7.5. In further embodiments, the pH value of the composition is between 6.0 and 6.5. In particular embodiments, the pH value of the composition is 6.

In embodiments of the tenth aspect of the present invention, the pH value of the composition is adjusted using phosphoric acid or hydrogen chloride. In particular embodiments, the pH value of the composition is adjusted using phosphoric acid.

In embodiments of the tenth aspect of the present invention, the concentration of CD-RAP or the variant thereof is between 1 and 10 mg/ml, i.e. 1, 2, 3, 4, 5, 6, 7, 8, 9, or 10 mg/ml.

In particular embodiments, the concentration of CD-RAP is between 2 and 5 mg/ml.

In particular embodiments of the tenth aspect of the present invention, the composition produced comprises 2 mg/ml CD-RAP or a variant thereof, 20 mM citrate, and 200 MM arginine, in an aqueous solution and has a pH value of 6.

In an eleventh aspect, the present invention provides a method of storing CD-RAP, comprising keeping CD-RAP in a buffer comprising at least one positively charged amino acid.

In particular embodiments of the eleventh aspect, CD-RAP is human CD-RAP, in particular human CD-RAP according to SEQ ID NO: 1 or a variant thereof.

In particular embodiments, said variant has at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% amino acid sequence identity to CD-RAP according to SEQ ID NO: 1.

In particular embodiments, the CD-RAP is the native CD-RAP obtained via the method of the fifth aspect of the present invention as described in detail above.

In embodiments of the eleventh aspect of the present invention, the at least one positively charged amino acid increases the stability of CD-RAP, in particular by preventing the degradation, denaturation and/or aggregation of CD-RAP. In particular embodiments, the at least one positively charged amino acid prevents the aggregation of CD-RAP. In particular embodiments the at least one positively charged amino acid is selected from the group consisting of arginine, lysine, and histidine.

In embodiments of the eleventh aspect of the present invention, the buffer increases the stability of CD-RAP, in particular by preventing the degradation, denaturation and/or aggregation of CD-RAP. In particular embodiments, the buffer prevents the degradation of CD-RAP. In particular embodiments the buffer is selected from the group consisting of citrate buffer, phosphate buffer, histidine buffer and Tris buffer.

In embodiments, the buffer further comprises a sugar or an amino sugar. In particular embodiments, the sugar is a monosaccharide, disaccharide or trisaccharide, in particular selected from the group consisting of sucrose, maltose, trehalose or raffinose. In particular embodiments, the amino sugar is selected from the group consisting of glucosamine, N-methyl-glucosamine, galactosamine or neuraminic acid.

In particular embodiments, the buffer does not comprise ascorbic acid and/or glycine.

In embodiments of the tenth aspect of the present invention, the buffer comprises arginine in a concentration of 50-500 mM, i.e. 50, 60, 70, 80, 90, 100, 150, 200, 250, 300, 350, 400, 450, or 500 mM. In embodiments, the buffer comprises arginine in a concentration of 100-350 mM. In further embodiments, the buffer comprises arginine in a concentration of 100-200 mM. In particular embodiments, the buffer comprises arginine in a concentration of 200 mM.

In embodiments of the tenth aspect of the present invention, the buffer comprises histidine in a concentration of 5-100 mM, i.e. 5, 6, 7, 8, 9, 10, 20, 25, 30, 35, 40, 45, 60, 65, 70, 75, 80, 85, 90, 95, or 100 mM. In embodiments the buffer comprises histidine in a concentration of 10-50 mM. In further embodiments the buffer comprises histidine in a concentration of 20-50 mM. In particular embodiments the buffer comprises histidine in a concentration of 50 mM.

In embodiments of the eleventh aspect of the present invention, the buffer is a phosphate buffer. In embodiments wherein the buffer is a phosphate buffer, the buffer comprises sodium phosphate in an aqueous solution, in particular in a concentration of 5-100 mM, i.e. 5, 6, 7, 8, 9, 10, 20, 25, 30, 35, 40, 45, 60, 65, 70, 75, 80, 85, 90, 95, or 100 mM. In embodiments the buffer comprises sodium phosphate in a concentration of 10-50 mM. In further embodiments the buffer comprises sodium phosphate in a concentration of 20-50 mM. In particular embodiments the buffer comprises sodium phosphate in a concentration of 20 mM.

In embodiments, wherein the buffer is a phosphate buffer, the buffer comprises potassium phosphate in an aqueous solution, in particular in a concentration of 5-100 mM, i.e. 5, 6, 7, 8, 9, 10, 20, 25, 30, 35, 40, 45, 60, 65, 70, 75, 80, 85, 90, 95, or 100 mM. In further embodiments the buffer comprises potassium phosphate in a concentration of 20-50 mM. In particular embodiments the buffer comprises potassium phosphate in a concentration of 20 mM.

In embodiments of the eleventh aspect of the present invention, the buffer is a citrate buffer. In embodiments wherein the buffer comprises a citrate buffer, the buffer comprises citrate in an aqueous solution, in particular in a concentration of 5-100 mM, i.e. 5, 6, 7, 8, 9, 10, 20, 25, 30, 35, 40, 45, 60, 65, 70, 75, 80, 85, 90, 95, or 100 mM. In embodiments the buffer comprises citrate in a concentration of 10-50 mM. In further embodiments the buffer comprises citrate in a concentration of 20-50 mM. In particular embodiments the buffer comprises citrate in a concentration of 20 mM.

In embodiments of the tenth aspect of the present invention, the buffer further comprises sucrose. In embodiments the buffer comprises sucrose in a concentration of 5-100 mM, i.e. 5, 6, 7, 8, 9, 10, 20, 25, 30, 35, 40, 45, 60, 65, 70, 75, 80, 85, 90, 95, or 100 mM. In embodiments the composition comprises sucrose in a concentration of 10-50 mM. In further embodiments the composition comprises sucrose in a concentration of 20-50 mM. In particular embodiments the composition comprises sucrose in a concentration of 45 mM.

In embodiments of the tenth aspect of the present invention, the buffer further comprises a negatively charged amino acid. In particular embodiments, the negatively charged amino acid is selected from the group consisting of glutamic acid and aspartic acid. In particular embodiments, the buffer comprises a combination of glutamic acid and aspartic acid In embodiments, wherein the buffer comprises a combination of glutamic acid and aspartic acid, the total concentration of arginine and glutamic acid of 50-500 mM, i.e. 50, 60, 70, 80, 90, 100, 150, 200, 250, 300, 350, 400, 450, or 500 mM. In embodiments, the buffer comprises a combination of glutamic acid and aspartic acid in a total concentration of 100-350 mM, in particular of 100-200 mM. In particular embodiments the buffer comprises a combination of glutamic acid and aspartic acid in a total concentration of 200 mM.

In embodiments, wherein the buffer comprises a combination of arginine and glutamic acid, arginine and glutamic acid are present in a ratio of 1:1. In particular embodiments arginine and glutamic acid are present in a ratio of 1:1.25. In further embodiments arginine and glutamic acid are present in a ratio of particularly 1:1.5. In particular embodiments, arginine and glutamic acid are present in a ratio of 1:2.

In embodiments of the eleventh aspect of the present invention, the pH value of the buffer is between 5.5 and 8.0, i.e. 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, or 8.0. In embodiments, the pH value of the buffer is between 6.0 and 7.5. In further embodiments, the pH value of the buffer is between 6.0 and 6.5. In particular embodiments, the pH value of the composition is 6.

In embodiments of the eleventh aspect of the present invention, the pH value of the buffer is adjusted using phosphoric acid or hydrogen chloride. In particular embodiments, the pH value of the buffer is adjusted using phosphoric acid.

In embodiments of the eleventh aspect of the present invention, the concentration of CD-RAP or the variant thereof is between 1 and 10 mg/ml, i.e. 1, 2, 3, 4, 5, 6, 7, 8, 9, or 10 mg/ml. In particular embodiments, the concentration of CD-RAP is between 2 and 5 mg/ml.

In particular embodiments of the eleventh aspect of the present invention, 2 mg/ml CD-RAP or a variant thereof, are stored in a buffer comprising 20 mM citrate and 200 MM arginine in an aqueous solution and has a pH value of 6.

In particular embodiments of the eleventh aspect, CD-RAP is stored at a temperature of −80° C. to 40° C., in particular at −20° C. to 25°, particularly at −20° C. to 5° C.

In particular embodiments of the eleventh aspect, CD-RAP is stored for a time period of up to 6 months, i.e. up to 6 months, up to 5 months, up to 4 months, up to 3 months, up to 2 months, up to 1 months, up to 3 weeks, up to 2 weeks, up to 1 week, up to 6 days, up to 5 days, up to 4 days, up to 3 days, up to 2 days, up to 1 day. In particular embodiments, CD-RAP is stored up to 3 months, in particular up to 1 months.

In particular, CD-RAP is stored for above indicated time period without substantially aggregating, denaturing, or degrading.

In a twelfth aspect, the present invention provides a composition comprising liposomes comprising encapsulated CD-RAP or a variant thereof, wherein the size of the liposomes is below 200 nm.

In particular embodiments, CD-RAP is human CD-RAP, in particular human CD-RAP according to SEQ ID NO: 1 or a variant thereof. In particular embodiments, said variant has at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, or at least 99% amino acid sequence identity to CD-RAP according to SEQ ID NO: 1.

In particular embodiments, the CD-RAP is the native CD-RAP obtained via the method of the fifth aspect of the present invention as described in detail above.

In embodiments of the twelfth aspect, the size of the liposomes is below 200 nm, i.e. below 200 nm, below 190 nm, below 180 nm, below 170 nm, below 160 nm, below 150 nm, below 140 nm, 130 nm, below 120 nm, below 110 nm, below 100 nm, below 90 nm, below 80 nm, below 70 nm, below 60 nm, below 50 nm, below 40 nm, below 30 nm, below 20 nm, or below 10 nm. In particular embodiments, the size of the lysosomes is below 150 nm. In further embodiments, the size of the lysosomes is 120 nm, in particular below 100 nm.

In embodiments of the twelfth aspect, more than 20% of total CD-RAP are encapsulated in the liposomes. In particular embodiments, at least 30% of total CD-RAP are encapsulated in the liposomes. In further embodiments, at least 40% of total CD-RAP are encapsulated in the liposomes. In embodiments 40-100% of total CD-RAP are encapsulated in the liposomes, i.e. 40%), 45%, 50%, 55%, 60%, 65%, 70%, 75%, 80%, 85%, 90%, 95%, 96%, 97%, 98%, or 99% of total CD-RAP are encapsulated in the liposomes. In particular embodiments 40%-90%, 40-80%, 50-90%, 50-80%, 60-90%, 60-80%, 70-80%, 70-90%, or 80-90% of total CD-RAP are encapsulated in the liposomes.

In embodiments of the twelfth aspect, the ratio of CD-RAP to liposomes is between 1:0.5 to 1:1.5, i.e. 1:0.5, 1:0.6, 1:0.7, 1:0.8, 1:0.9, 1:1, 1:1.1, 1:1.2, 1:1.31:1.4, 1:1.5. In particular embodiments, the ratio of CD-RAP to liposomes is1:1.2.

In embodiments of the twelfth aspect, the polydisperity index (PDI) of the liposomes is below 0.3. In particular embodiments, the PDI is below 0.2, in particular below 0.15. In particular embodiments, the PDI is 0.132.

In embodiments of the twelfth aspect, the liposomes are composed of one or more lipids. In embodiments, the one or more lipid is selected from the group consisting of glycerides, phospholipids, glycerophospholipides, glycerophosphinolipids, glycerophosphonolipids, sulfolipids, sphingolipids, isoprenolides, steroids, stearines, steroles and carbohydrate containing lipids. In particular embodiments, the liposomes are composed of lipids selected from the group consisting of phosphatidic acid (PA), phosphatidylethanolamine (PE), phosphatidylcholine (PC), phosphatidylserine (PS), and phosphoinositides such as phosphatidylinositol (PI), phosphatidylinositol phosphate (PIP), phosphatidylinositol bisphosphate (PIP2), phosphatidylinositol triphosphate (PIP3), cardiolipin, lysophospholipids, and cholesterol. In embodiments, the liposomes are composed of at least two lipids. In further embodiments, the liposomes are composed of phospholipds and sterol. In particular embodiments, the liposomes are composed of phosphatidylcholine and cholesterol.

In further embodiments, the lipids phosphatidylcholine and cholesterol are present in a ratio of 60:40, 65:35, 70:30, 75:25, 80:20:85:15, or 90:10. In particular embodiments the lipids phosphatidylcholine and cholesterol, are present in a ratio of 74.8:25.2.

In embodiments of the twelfth aspect, the liposomes further comprise a hydrophobic ascorbate ester. In particular embodiments, the hydrophobic ascorbate ester is ascorbyl palmiate.

In further embodiments, the ascorbate ester is present in a ratio of 0.1:99.9, to 1:99 to the amount of phospholipids and sterols, i.e. in a ratio of 0.1:99.9, 0.2:99.8, 0.3:99.7, 0.4:99.6, 0.5:99.5, 0.6:99.4, 0.7:99.3, 0.8:99.2, 0.9:99.1, or 1.0:99.0. In particular embodiments, the ascorbate ester is present in a ratio of 0.1:99.9 to the amount of phospholipids and sterols.

In embodiments of the twelfth aspect, CD-RAP and the lysosomes are present in a phosphate buffer or a citrate buffer containing at least one positively charged amino acid.

In particular embodiments, the at least one positively charged amino acid increases the stability of CD-RAP, in particular by preventing the degradation, denaturation and/or aggregation of CD-RAP. In particular embodiments, the at least one positively charged amino acid prevents the aggregation of CD-RAP. In particular embodiments the at least one positively charged amino acid is selected from the group consisting of arginine, lysine, and histidine.

In further embodiments, the buffer increases the stability of CD-RAP, in particular by preventing the degradation, denaturation and/or aggregation of CD-RAP. In particular embodiments, the buffer prevents the degradation of CD-RAP.

In embodiments of the twelfth aspect of the present invention, the composition comprises arginine in a concentration of 20-500 mM, i.e. 20, 30, 40, 50, 60, 70, 80, 90, 100, 150, 200, 250, 300, 350, 400, 450, or 500 mM. In embodiments, the composition comprises arginine in a concentration of 100-350 mM. In further embodiments, the composition comprises arginine in a concentration of 100-200 mM. In particular embodiments, the composition comprises arginine in a concentration of 200 mM.

In embodiments of the twelfth aspect of the present invention, the composition comprises histidine in a concentration of 5-100 mM, i.e. 5, 6, 7, 8, 9, 10, 20, 25, 30, 35, 40, 45, 60, 65, 70, 75, 80, 85, 90, 95, or 100 mM. In embodiments the composition comprises histidine in a concentration of 10-50 mM. In further embodiments the composition comprises histidine in a concentration of 20-50 mM. In particular embodiments the composition comprises histidine in a concentration of 20 mM.

In embodiments of the twelfth aspect of the present invention, the composition comprises 0.1-10% lysine, i.e. 0.1%, 0.2%, 0.3%, 0.4%, 0.5%, 0.6%, 0.7%, 0.8%, 0.9%, 1.0% 1.5%, 2.0%, 2.5%, 3.0%, 3.5%, 4.0%, 4.5%, 5.0%, 5.5%, 6.0%, 6.5%, 7.0%, 7.5%, 8.0%, 8.5%, 9.0%, 9.5%, 10% lysine. In embodiments of the first aspect, the composition comprises 0.5%-7.5% lysine. In further embodiments, the composition comprises 1.0%-5.0% lysine. In particular embodiments, the composition comprises 2.0%-3.0% lysine.

In embodiments of the first aspect of the present invention, the composition comprises a phosphate buffer. In embodiments wherein the composition comprises a phosphate buffer, the composition comprises sodium phosphate in an aqueous solution, in particular in a concentration of 5-100 mM, i.e. 5, 6, 7, 8, 9, 10, 20, 25, 30, 35, 40, 45, 60, 65, 70, 75, 80, 85, 90, 95, or 100 mM. In embodiments the composition comprises sodium phosphate in a concentration of 10-50 mM. In further embodiments the composition comprises sodium phosphate in a concentration of 20-50 mM. In particular embodiments the composition comprises sodium phosphate in a concentration of 20 mM.

In embodiments, wherein the composition comprises a phosphate buffer, the composition comprises potassium phosphate in an aqueous solution, in particular in a concentration of 5-100 mM, i.e. 5, 6, 7, 8, 9, 10, 20, 25, 30, 35, 40, 45, 60, 65, 70, 75, 80, 85, 90, 95, or 100 mM. In further embodiments the composition comprises potassium phosphate in a concentration of 20-50 mM. In particular embodiments the composition comprises potassium phosphate in a concentration of 20 mM.

In embodiments of the twelfth aspect of the present invention, the composition comprises a citrate buffer. In embodiments wherein the composition comprises a citrate buffer, the composition comprises citrate in an aqueous solution, in particular in a concentration of 5-100 mM, i.e. 5, 6, 7, 8, 9, 10, 20, 25, 30, 35, 40, 45, 60, 65, 70, 75, 80, 85, 90, 95, or 100 mM. In embodiments the composition comprises citrate in a concentration of 10-50 mM. In further embodiments the composition comprises citrate in a concentration of 20-50 mM. In particular embodiments the composition comprises citrate in a concentration of 20 mM.

In embodiments of the twelfth aspect of the present invention, the composition further comprises sucrose. In embodiments the composition comprises sucrose in a concentration of 5-100 mM, i.e. 5, 6, 7, 8, 9, 10, 20, 25, 30, 35, 40, 45, 60, 65, 70, 75, 80, 85, 90, 95, or 100 mM. In embodiments the composition comprises citrate in a concentration of 10-50 mM. In further embodiments the composition comprises citrate in a concentration of 20-50 mM.

In particular embodiments the composition comprises citrate in a concentration of 45 mM.

In embodiments of the twelfth aspect of the present invention, the composition further comprises a negatively charged amino acid. In particular embodiments, the negatively charged amino acid is selected from the group consisting of glutamic acid and aspartic acid. In particular embodiments, the composition comprises a combination of glutamic acid and aspartic acid.

In embodiments, wherein the composition comprises a combination of glutamic acid and aspartic acid, the total concentration of arginine and glutamic acid of 50-500 mM, i.e. 50, 60, 70, 80, 90, 100, 150, 200, 250, 300, 350, 400, 450, or 500 mM. In embodiments, the composition comprises a combination of glutamic acid and aspartic acid in a total concentration of 100-350 mM, in particular of 100-200 mM. In particular embodiments the composition comprises a combination of glutamic acid and aspartic acid in a total concentration of 200 mM.

In embodiments, wherein the composition comprises a combination of arginine and glutamic acid, arginine and glutamic acid are present in a ratio of 1:1. In particular embodiments arginine and glutamic acid are present in a ratio of 1:1.25. In further embodiments arginine and glutamic acid are present in a ratio of particularly 1:1.5. In particular embodiments, arginine and glutamic acid are present in a ratio of 1:2.

In embodiments of the twelfth aspect of the present invention, the pH value of the composition is between 5.5 and 8.0, i.e. 5.5, 5.6, 5.7, 5.8, 5.9, 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, or 8.0. In embodiments, the pH value of the composition is between 6.0 and 7.5. In further embodiments, the pH value of the composition is between 6.0 and 6.5. In particular embodiments, the pH value of the composition is 6.

In embodiments of the twelfth aspect of the present invention, the pH value of the composition is adjusted using phosphoric acid or hydrogen chloride. In particular embodiments, the pH value of the composition is adjusted using phosphoric acid.

In a thirteenth aspect, the present invention provides the composition of the twelfth aspect as described in detail above, for use in a method of treating and/or preventing joint disease or injury in patients. In particular embodiments of a joint disease or injury, the cartilage and/or the soft-tissue, is affected. In particular, the joint disease or injury is a cartilage disease or injury and/or a disease or injury of the cruciate ligaments and/or the collateral ligaments. In further embodiments, the cartilage is affected in manner leading to its degradation. The degradation of the cartilage may be caused by various factors. Cartilage degradation may be caused or triggered by an injury such as but not limited to a traumatic injury or a repetitive strain injury (such as e.g. chronic erosion of cartilage tissue due to repetitive activities). The severity of the cartilage degradation may range from grade 1 to grade 4 according to the classification of the International Cartilage Repair Society, i.e. from superficial lesions (grade 1) up to full thickness lesions, reaching bone tissue (grade 4). The area of cartilage degradation includes the area of initial cartilage lesion (i.e. which was caused by the traumatic injury or a repetitive strain injury) as well as cartilage in other areas, i.e. other joints or other part of the same joint, may also be injured after said injury. In further embodiments, bone fractures involving one or more joints may also distort cartilage morphology and, thus in the long run, induce cartilage degeneration.

Additionally or alternatively, cartilage degradation may be caused by disease such as but not limited to an inflammatory diseases, infectious diseases, genetic disorders, autoimmune diseases, degenerative disorders and proliferative disorders, in particular by rheumatoid arthritis, bacterial synovitis, sarcomas of the synovial tissue or of cartilage itself.

In embodiments of the thirteenth aspect, the composition of the twelfth aspect is for use in treating and/or preventing joint disease or injury in patients suffering from cartilage degradation and/or increased influx of water into the cartilage, and/or decreased presence of CD-RAP in the cartilage.

In further embodiments, the cartilage degradation involves the degradation of proteoglycans, in particular of aggrecan. Proteoglycan degradation may occur due to protease cleavage. Proteases involved in the degradation of proteoglycans, preferably of aggrecan, include but are not limited to matrix-metalloproteinases (MMPs), Cathepsins, A Disintegrin And Metalloproteinase (ADAM), and A Disintegrin And Metalloproteinase with Thrombospondin motif (ADAMTS). In preferred embodiments, proteoglycans, preferably aggrecan, are degraded by a protease selected from the group consisting of MMP-1, MMP-3, MMP-2, MMP-7, MMP-8, MMP-9, MMP-13, Cathepsin D, ADAMTS-1, ADAMTS-4, ADAMTS-5, ADAMTS-8, ADAMTS-9, ADAMTS-15, ADAMTS-16, and ADAMTS-18. Particularly preferred are ADAMTS-4 and/or ADAMTS-5.

In further embodiments, the protease cleavage occurs at a cleavage site located between the globular G1 and G2 domain of aggrecan. In further embodiments, the polypeptide chain of aggrecan is cleaved between Asn341-Phe342 and/or between Glu373-Ala374, preferably at the Glu373-Ala374 peptide bond.

In further embodiments, the composition of the twelfth aspect is for use in treating and/or preventing joint disease or injury in patients suffering from aggrecan degradation. In particular embodiments 0.5%-5% of aggrecan are degraded, i.e. 0.5%, 1%, 1.5%, 2%, 2.5%, 3%, 3.5%, 4%, 4.5%, or 5% of aggrecan are degraded. In particular embodiments more than 0.5%, more than 1%, more than 1.5%, more than 2%, more than 2.5%, more than 3%, more than 3.5%, more than 4%, or more than 4.5% of aggrecan are degraded. In particular, the cartilage degradation is measured in comparison to unremarkable, non-diseased cartilage tissue, which typically but not necessarily exhibits a density of proteoglycans equivalent to 65-150 mg/ml, i.e. 65, 70, 75, 80, 85, 90, 95, 100, 110, 120, 130, 140, or 150 mg/ml. Alternatively, unremarkable, non-diseased cartilage tissue typically but not necessarily exhibits a density of proteoglycans equivalent to 400, 450, 500, 550, 600, 650, 700, 750, 800, 850, 900, 950, or 1000 msec in the T1 value visualised by DGEMRIC technique. In particular embodiments, the cartilage degradation results in a proteoglycan density of below 65, below 60, below 55, below 50, below 45, below 40, below 35, below 30, below 25, below 20, below 15, below 10, or below 5 mg/ml. Alternatively, cartilage degradation results in a proteoglycan density of below 400, below 350, below 300, below 250, below 200, below 150, below 100, or below 50 msec in the T1 value visualised by DGEMRIC technique.

Accordingly, in particular embodiments, the composition of the twelfth aspect decreases the cartilage degradation to a proteoglycan density above 5, 10, 15, 20, 25, 30, 35, 40, 45, 50, 55, 60, or 65 mg/ml. Alternatively, the the composition of the twelfth aspect decreases the cartilage degradation to a proteoglycan density of above 50, 100, 150, 200, 250, 300, 350, or 400 msec in the T1 value visualised by DGEMRIC technique.

The loss of intact proteoglycan, in particular the loss of intact aggrecan, in particular due to aggrecan degradation, i.e. the increase of cleaved proteoglycan, preferably aggrecan, leads to an influx of water into the cartilage and thereby to a swelling of the cartilage and thus the joint. Accordingly, in embodiments of the thirteenth aspect, the composition of the twelfth aspect is for use in treating and/or preventing joint disease or injury in patients suffering from an increased influx of water into the cartilage.

CD-RAP interacts with aggrecan and prevents its degradation, in particular its proteolytic degradation. The interaction of CD-RAP with aggrecan prevents proteases such as e.g. matrix-metalloproteinases (MMPs), Cathepsins, A Disintegrin And Metalloproteinase (ADAM), and A Disintegrin And Metalloproteinase with Thrombospondin motif (ADAMTS), preferably selected from the group consisting of MMP-1, MMP-3, MMP-2, MMP-7, MMP-8, MMP-9, MMP-13, Cathepsin D, ADAMTS-1, ADAMTS-4, ADAMTS-5, ADAMTS-8, ADAMTS-9, ADAMTS-15, ADAMTS-16, and ADAMTS-18, from being able to cleave the aggrecan peptide chain. The decreased presence or complete absence of CD-RAP leads to an increased degradation of aggrecan.

Thus, in embodiments of the thirteenth aspect, the composition of the twelfth aspect is for use in treating and/or preventing joint disease or injury in patients suffering from a decreased presence of CD-RAP in the joint. In particular embodiments, the presence of CD-RAP is decreased in the cartilage.

The decreased presence of CD-RAP may be due to a decreased expression of CD-RAP. Alternatively and/or additionally, the presence of CD-RAP may be decreased due to it being retained in the expressing cells, in particular due to it being retained in chondrocytes. Alternatively and/or additionally, the presence of CD-RAP may be decreased due to it being degraded inside the expressing cells, in particular in the chondrocytes, or after it being secreted from the cells into the extracellular space, preferably the cartilage.

In particular embodiments of the thirteenth aspect, the composition of the twelfth aspect is for use in treating and/or preventing joint disease or injury in patients suffering from a decreased expression of CD-RAP, a retention of CD-RAP in the cells, preferably the chondrocytes, or a degradation of CD-RAP in the cells, preferably the chondrocytes, or the extracellular space.

In particular embodiments of the thirteenth aspect, the composition of the twelfth aspect is for use in treating and/or preventing cartilage disease or injury in patients suffering from aggrecan degradation, and/or increased influx of water into the cartilage, and/or decreased CD-RAP presence, wherein the cartilage disease is selected from the group consisting of osteoarthritis (OA), rheumatoid arthritis (RA), chondrodysplasia, chondromalacia, chondrosarcoma, degenerative disk disease, hip dysplasia, osteoarthropathy of the fingers, osteochondritis dissecans, and polychondritis.

In particular embodiments, the osteoarthritis is selected from the group consisting of Kellgren-Lawrence osteoarthritis, ankle osteoarthritis, elbow osteoarthritis, finger osteoarthritis, hip osteoarthritis, knee osteoarthritis, shoulder osteoarthritis, spine osteoarthritis, toe osteoarthritis, wrist osteoarthritis. In particular embodiments, the OA is early onset OA.

In particular embodiments of the thirteenth aspect, the composition of the twelfth aspect is for use in treating and/or preventing cartilage disease or injury in patients suffering from aggrecan degradation, and/or increased influx of water into the cartilage, and/or decreased CD-RAP presence, wherein the cartilage injury is a traumatic injury or a repetitive strain injury (such as e.g. chronic erosion of cartilage tissue due to repetitive activities). The severity of the cartilage degradation may range from grade 1 to grade 4 according to the classification of the International Cartilage Repair Society, i.e. from superficial lesions (grade 1) up to full thickness lesions, reaching bone tissue (grade 4). The area of cartilage degradation includes the area of initial cartilage lesion (i.e. which was caused by the traumatic injury or a repetitive strain injury) as well as cartilage in other areas, i.e. other joints or other part of the same joint, may also be injured after said injury. In further embodiments, bone fractures involving one or more joints may also distort cartilage morphology and, thus in the long run, induce cartilage degeneration.

In embodiments of the thirteenth aspect, the patient is a mammal, reptile or bird. In particular embodiments, the patient is selected from the group consisting of laboratory animals (e.g. mouse or rat), domestic animals (including e.g. guinea pig, rabbit, horse, donkey, cow, sheep, goat, pig, chicken, camel, cat, dog, turtle, tortoise, snake, or lizard), or primates including chimpanzees, bonobos, gorillas and human beings. Human beings are in particular referred to.

In further embodiments of the thirteenth aspect, the composition of the twelfth aspect alters the degree of cartilage degradation in a patient. In particular embodiments, the composition of the eleventh aspect decreases the degree of cartilage degradation, more preferably the degree of aggrecan degradation, in a patient. In particular, the composition of the eleventh aspect of the present invention decreases the degree of cartilage degradation, preferably the degree of aggrecan degradation, by at least 5%, at least 10%, at least 15%, at least 20%, or at least 25%. In particular embodiments more than 0.5%, more than 1%, more than 1.5%, more than 2%, more than 2.5%, more than 3%, more than 3.5%, more than 4%, or more than 4.5% of aggrecan are degraded. In particular, the cartilage degradation is measured in comparison to unremarkable, non-diseased cartilage tissue, which typically but not necessarily exhibits a density of proteoglycans equivalent to 65-150 mg/ml, i.e. 65, 70, 75, 80, 85, 90, 95, 100, 110, 120, 130, 140, or 150 mg/ml. Alternatively, unremarkable, non-diseased cartilage tissue typically but not necessarily exhibits a density of proteoglycans equivalent to 400, 450, 500, 550, 600, 650, 700, 750, 800, 850, 900, 950, or 1000 msec in the T1 value visualised by DGEMRIC technique. In particular embodiments, the cartilage degradation results in a proteoglycan density of below 65, below 60, below 55, below 50, below 45, below 40, below 35, below 30, below 25, below 20, below 15, below 10, or below 5 mg/ml. Alternatively, cartilage degradation results in a proteoglycan density of below 400, below 350, below 300, below 250, below 200, below 150, below 100, or below 50 msec in the T1 value visualised by DGEMRIC technique.

Accordingly, in particular embodiments, the composition of the twelfth aspect decreases the cartilage degradation to a proteoglycan density above 5, 10, 15, 20, 25, 30, 35, 40, 45, 50, 55, 60, or 65 mg/ml. Alternatively, the aggrecan binding moiety decreases the cartilage degradation to a proteoglycan density of above 50, 100, 150, 200, 250, 300, 350, or 400 msec in the T1 value visualised by DGEMRIC technique.

In further embodiments of the twelfth or thirteenth aspect of the present invention, the composition is for intra-articular administration.

In a fourteenth aspect, the present invention provides a pharmaceutical comprising the composition of the twelfth or the thirteenth aspect of the present invention as described in detail above. In particular embodiments, the pharmaceutical further comprises a pharmaceutically acceptable carrier and/or excipient and optionally one or more additional active substances.

In particular embodiments, the carrier is liquid. In further embodiments, the liquid carrier include but are not limited to sterile liquids, such as saline solutions in water and oils, including those of petroleum, animal, vegetable or synthetic origin, such as peanut oil, soybean oil, mineral oil, sesame oil and the like. Saline solutions and aqueous dextrose and glycerol solutions can also be employed as liquid carriers, particularly for injectable solutions. A saline solution is a preferred carrier when the pharmaceutical composition is administered intravenously. Examples of suitable pharmaceutical carriers are described in "Remington's Pharmaceutical Sciences" by E. W. Martin.

In further embodiments, the excipients include but are not limited to starch, glucose, lactose, sucrose, gelatin, malt, rice, flour, chalk, silica gel, sodium stearate, glycerol monostearate, talc, sodium chloride, dried skim milk, glycerol, propylene, glycol, water, and ethanol.

In further embodiments, the adjuvant augments, stimulates, activates, potentiates, or modulates the effect of the active ingredient. In particular, the adjuvants is selected from the group consisting of inorganic adjuvants (e.g. inorganic metal salts such as aluminium phosphate or aluminium hydroxide), organic adjuvants (e.g. saponins or squalene), oil-based adjuvants (e.g. Freund's complete adjuvant and Freund's incomplete adjuvant), cytokines (e.g. IL-ip, IL-2, IL-7, IL-12, IL-18, GM-CFS, and INF-γ) particulate adjuvants (e.g. immuno-stimulatory complexes (ISCOMS), liposomes, or biodegradable microspheres), virosomes, bacterial adjuvants (e.g. monophosphoryl lipid A, or muramyl peptides), synthetic adjuvants (e.g. non-ionic block copolymers, muramyl peptide analogues, or synthetic lipid A), and synthetic polynucleotides adjuvants (e.g polyarginine or polylysine).

In embodiments wherein an additional active substance is present it is preferred that said active substance is an active ingredient which provides a pharmaceutical value. In particular, the pharmaceutical composition may comprise one or more active ingredients which may act in conjunction with or independently of each other. The active ingredient can be formulated as neutral or salt forms. Pharmaceutically acceptable salts include those formed with free amino groups such as those derived from hydrochloric, phosphoric, acetic, oxalic, tartaric acids, etc., and those formed with free carboxyl groups such as but not limited to those derived from sodium, potassium, ammonium, calcium, ferric hydroxides, isopropylamine, triethylamine, 2-ethylamino ethanol, histidine, and procaine.

In a fifteenth aspect, the present invention provides a method of producing a liposomal formulation comprising the steps of
a) dissolving at least one lipid in an organic solvent,
b) injecting the mixture of step a) into a circulating aqueous phase, and
c) eliminating the solvent.

In embodiments of the fifteenth aspect, the method further comprises step d) mixing the liposomal formulation obtained by steps a-c) with a composition comprising CD-RAP. Thereby, the pre-formed liposomes are spiked with CD-RAP.

In embodiments, the organic solvent of step a) is a class 3 solvent. In particular the solvent is selected from the group consisting of acetic acid, acetone, anisole, 1-butanol, 2-butanol, butyl acetate, tert-butylmethyl ether, cumene, dimethyl sulfoxide, ethanol, ethyl acetate, ethyl ether ethyl formate, formic acid, heptane, isobutyl acetate, isopropyl acetate, methyl acetate, 3-methyl-1-butanol, methylethylketone, methylisobutylketone, 2-methyl-1-propanol, pentane, 1-pentanol, 1-propanol, 2-propanol, propyl acetate, more preferably 1-propanol.

In embodiments of the fifteenth aspect, the at least one lipid of step a) is selected from the group consisting of glycerides, glycerophospholipides, glycerophosphinolipids, glycerophosphonolipids, sulfolipids, sphingolipids, phospholipids, isoprenolides, steroids, stearines, steroles and carbohydrate containing lipids. In particular embodiments, the at least one lipid is selected from the group consisting of phosphatidic acid (PA), phosphatidylethanolamine (PE), phosphatidylcholine (PC), phosphatidylserine (PS), and phosphoinositides such as phosphatidylinositol (PI), phosphatidylinositol phosphate (PIP), phosphatidylinositol bis-phosphate (PIP2), phosphatidylinositol triphosphate (PIP3), cardiolipin, lysophospholipids, and cholesterol. In particular embodiments, the at least one lipid is a combination of two lipids, in particular a combination of a phospholipid and a sterol, in particular a combination of phosphatidylcholine and cholesterol.

In embodiments of the fifteenth aspect, in step a) two or more lipids are dissolved in the organic solvent. In embodiments, one or more phospholipid and one or more sterol are dissolved in the organic solvent. In particular embodiments, the lipids phosphatidylcholine and cholesterol are dissolved in the organic solvent. In particular, the ration between lipids and organic solvent is 3:1.

In further embodiments, the total concentration of lipids in the solvent is 0.02 to 0.4 g/ml, i.e. 0.02 g/ml, 0.03 g/ml, 0.04 g/ml, 0.05 g/ml, 0.06 g/ml, 0.07 g/ml, 0.08 g/ml, 0.09 g/ml, 0.10 g/ml, 0.11 g/ml, 0.12 g/ml, 0.13 g/ml, 0.14 g/ml, 0.15 g/ml, 0.16 g/ml, 0.17 g/ml, 0.18 g/ml, 0.19 g/ml, 0.2 g/ml, 0.21 g/ml, 0.22 g/ml, 0.23 g/ml, 0.24 g/ml, 0.25 g/ml, 0.26 g/ml, 0.27 g/ml, 0.28 g/ml, 0.29 g/ml, 0.30 g/ml, 0.31 g/ml, 0.32 g/ml, 0.33 g/ml, 0.34 g/ml, 0.35 g/ml, 0.36 g/ml, 0.37 g/ml, 0.38 g/ml, 0.39 g/ml, or 0.4 g/ml. In particular embodiments, the total concentration of lipids in the solvent is 0.03-0.3 g/ml, 0.03-0.1 g/m10.03-0.05 g/ml. In particular embodiments, the total concentration of lipids in the solvent is 0.033 g/ml.

In further embodiments of the fifteenth aspect, in addition to the at least one lipid in step a) a hydrophobic ascorbate ester is dissolved in the organic solvent. In particular embodiments, the hydrophobic ascorbate ester is ascorbyl palmiate, In further embodiments, the ascorbate ester is present in a ratio of 0.1:99.9, to 1:99 to the amount of phospholipids and sterols, i.e. in a ratio of 0.1:99.9, 0.2:99.8, 0.3:99.7, 0.4:99.6, 0.5:99.5, 0.6:99.4, 0.7:99.3, 0.8:99.2, 0.9:99.1, or 1.0:99.0. In particular embodiments, the ascorbate ester is present in a ratio of 0.1:99.9 to the amount of phospholipids and sterols.

In further embodiments of the fifteenth aspect, with a speed of 1-10 ml/min, i.e. with a speed of 1, 2, 3, 4, 5, 6, 7, 8, 9, or 10 ml/min. In particular embodiments, the mixture is injected with a speed of 5 ml/min.

In further embodiments of the fifteenth aspect, the aqueous phase circulates at a speed of 500-3000 ml/min, i.e. 500, 600, 700, 800, 900, 1000, 1100, 1200, 1300, 1400, 1500, 1600, 1700, 1800, 1900, 2000, 2100, 2200, 2300, 2400, 2500, 2600, 2700, 2800, 2900, or 3000 ml/min. In particular embodiments, the aqueous phase circulates at a speed of 1000-2500, 1500-2500, or 2000-2500 ml/min. In particular embodiments, the aqueous phase circulates at a speed of 2200 ml/min.

In particular embodiments, the aqueous phase is circulated by shear-inducing device. In embodiments, the shear-inducing device is a static mixer or a normal stirrer. In particular the shear-inducing device is a static mixer. In embodiments of the first aspect, the static mixer has an internal diameter of 10-15 mm, i.e. of 10, 11, 12, 13, 14, or 15 mm, In particular embodiments, the static mixer has an internal diameter of 12-13 mm, i.e. 12.0, 12.1, 12.2, 12.3, 12.4, 12.5, 12.6, 12.7, 12.8, 12.9, or 13.0 mm. In embodiments, the static mixer is suitable to mix a final volume of 150-300 ml, i.e. 150, 160, 170, 180, 190, 200, 210, 220, 230, 240, 250, 260, 270, 280, 290, or 300 ml, of the liposomal formulation. In particular, the static mixer is suitable to mix a final volume of 170-300 ml, in particular a final volumn of 200-250 ml of the liposomal formulation. Accordingly in particular embodiments the ration between the internal diameter of the static mixer to the volume of the mixed lipid formulation is 0.7 mm-1 mm, i.e 0.7, 0.8, 0.9, or 1.0 mm, internal diameter per 15 ml of lipid formulation. In particular embodiments, in step b) the mixture of a) is injected in front of a shear-inducing device. In particular embodiments, the mixture of a) is injected in front of a static mixer.

In further embodiments, the solvents are eliminated in step c) using filtration, in particular using tangential flow filtration.

In further embodiments, the composition of CD-RAP admixed in step d) comprises 1-10 mg/ml CD-RAP, i.e. 1, 2, 3, 4, 5, 6, 7, 8, 9, or 10 mg/ml CD-RAP. In particular embodiment, the composition comprises 2-9, 3-8, 4-8, 5-8, or 6-8 mg/ml CD-RAP. In particular embodiments, the composition comprises 7 mg/ml CD-RAP. IN further embodiments CD-RAP admixed in step d) is comprised in an arginine phosphate buffer or an arginine citrate buffer as described in detail above.

In further embodiments, the ratio between the liposomal formulation and CD-RAP is 1:1, 1.1:1, 1.2:1, 1.3:1, 1.4:1, or 1.5:1. In particular embodiments the ratio between the liposomal formulation and CD-RAP is 1.2:1.

In embodiments of the fifteenth aspect, the method further comprises step e) freeze-drying the liposomal formulation.

In embodiments of the fifteenth aspect, the method comprises step f) reconstituting the freeze-dried liposomal formulation in an arginine phosphate buffer or an arginine citrate buffer. In embodiments, the freeze-dried liposomal formulation is reconsited in a single step by adding and mixing the full reconstitution volume of the arginine phosphate buffer or an arginine citrate buffer at once. In embodiments, the freeze-dried liposomal formulation is reconsited in two or more subsequent steps by adding parts of the full reconstitution volume of the arginine phosphate buffer or an arginine citrate buffer in two or more subsequent steps, i.e. in a first step half of the volume of the full reconstitution volume of the arginine phosphate buffer or an arginine citrate buffer may be added and mixed and in a second step the second half of the full reconstitution volume of the arginine phosphate buffer or an arginine citrate buffer may be added and mixed. In embodiments, the reconsitions comprises two steps wherein in the first step one third of the volume of the full reconstitution volume of the arginine phosphate buffer or an arginine citrate buffer may be added and mixed and in the second step two third of the full reconstitution volume of the arginine phosphate buffer or an arginine citrate buffer may be added and mixed. In embodiments, the reconsitions comprises three steps wherein in each step one third of the full reconstitution volume of the arginine phosphate buffer or an arginine citrate buffer may be added and mixed.

In a sixteenth aspect, the present invention provides a liposomal formulation producible or produced by the method of the fourteenth aspect as described in detail above.

In a seventeenth aspect, the present invention provides a method of storing CD-RAP, comprising keeping CD-RAP in a liposomal formulation as specified in detail above with regard to the eleventh aspect of the present invention.

In embodiments of the seventeenth aspect, CD-RAP is stored in the liposomal formulation at a temperature of −80° C. to 40° C., i.e. at −80° C., −75° C., −70° C., −65° C., −60° C., −55° C., −50° C., −45° C., −40° C., −35° C., −30° C., −25° C., −20° C., −15° C., −10° C., −5° C., 0° C., 5° C., 10° C., 15° C., 20° C., 25° C., 30° C., 35° C., or 40° C. In embodiments of the sixth aspect, CD-RAP is stored in the liposomal formulation at a temperature of −20° C. to 25°, or at −10° to 10° C., in particular at 5° C.

In embodiments of the seventeenth aspect, CD-RAP is stored in the liposomal formulation for a time period of up to 6 months, i.e. up to 6 months, up to 5 months, up to 4 months, up to 3 months, up to 2 months, up to 1 months, up to 3 weeks, up to 2 weeks, up to 1 week, up to 6 days, up to 5 days, up to 4 days, up to 3 days, up to 2 days, up to 1 day. In embodiments of the sixth aspect, CD-RAP is stored in the liposomal formulation for up to 3 months, in particular for up to 1 months.

In particular, CD-RAP is stored for above indicated time period without substantially aggregating, denaturing, or degrading.

In an eighteenth aspect, the present invention provides a method of reducing the size of liposomes in a liposomal formulation as specified in detail above with regard to the first aspect of the present invention comprising the steps of
  a) dissolving at least one lipid in an organic solvent,
  b) injecting the mixture of step a) into a circulating aqueous phase, and
  c) eliminating the solvent.

In embodiments of the eighteenth aspect, the method further comprises step d) mixing the liposomal formulation obtained by steps a-c) with a composition comprising CD-RAP.

In embodiments, the organic solvent of step a) is a class 3 solvent. In particular the solvent is selected from the group consisting of acetic acid, acetone, anisole, 1-butanol, 2-butanol, butyl acetate, tert-butylmethyl ether, cumene, dimethyl sulfoxide, ethanol, ethyl acetate, ethyl ether ethyl formate, formic acid, heptane, isobutyl acetate, isopropyl acetate, methyl acetate, 3-methyl-1-butanol, methylethylketone, methylisobutylketone, 2-methyl-1-propanol, pentane, 1-pentanol, 1-propanol, 2-propanol, propyl acetate, more preferably 1-propanol.

In embodiments of the seventeenth aspect, the at least one lipid of step a) is selected from the group consisting of glycerides, glycerophospholipides, glycerophosphinolipids, glycerophosphonolipids, sulfolipids, sphingolipids, phospholipids, isoprenolides, steroids, stearines, steroles and carbohydrate containing lipids. In particular embodiments, the at least one lipid is selected from the group consisting of phosphatidic acid (PA), phosphatidylethanolamine (PE), phosphatidylcholine (PC), phosphatidylserine (PS), and phosphoinositides such as phosphatidylinositol (PI), phosphatidylinositol phosphate (PIP), phosphatidylinositol bisphosphate (PIP2), phosphatidylinositol triphosphate (PIP3), cardiolipin, lysophospholipids, and cholesterol. In particular embodiments, the at least one lipid is a combination of two lipids, in particular a combination of phospholipids and sterols. In particular embodiments, the at least one lipid is a combination of phosphatidylcholine and cholesterol.

In embodiments of the eighteenth aspect, in step a) two or more lipids are dissolved in the organic solvent. In particular embodiments, the lipids phosphatidylcholine and cholesterol are dissolved in the organic solvent. In particular, the ration between lipids and organic solvent is 3:1.

In further embodiments, the total concentration of lipids in the solvent is 0.02 to 0.4 g/ml, i.e. 0.02 g/ml, 0.03 g/ml, 0.04 g/ml, 0.05 g/ml, 0.06 g/ml, 0.07 g/ml, 0.08 g/ml, 0.09 g/ml, 0.10 g/ml, 0.11 g/ml, 0.12 g/ml, 0.13 g/ml, 0.14 g/ml, 0.15 g/ml, 0.16 g/ml, 0.17 g/ml, 0.18 g/ml, 0.19 g/ml, 0.2 g/ml, 0.21 g/ml, 0.22 g/ml, 0.23 g/ml, 0.24 g/ml, 0.25 g/ml, 0.26 g/ml, 0.27 g/ml, 0.28 g/ml, 0.29 g/ml, 0.30 g/ml, 0.31 g/ml, 0.32 g/ml, 0.33 g/ml, 0.34 g/ml, 0.35 g/ml, 0.36 g/ml, 0.37 g/ml, 0.38 g/ml, 0.39 g/ml, or 0.4 g/ml. In particular embodiments, the total concentration of lipids in the solvent is 0.03-0.3 g/ml, 0.03-0.1 g/m10.03-0.05 g/ml. In particular embodiments, the total concentration of lipids in the solvent is 0.033 g/ml.

In further embodiments of the eighteenth aspect, in addition to the at least one lipid in step a) an hydrophobic ascorbate ester is dissolved in the organic solvent. In particular embodiments, the hydrophobic ascorbate ester is ascorbyl palmiate, In further embodiments, the ascorbate ester is present in a ratio of 0.1:99.9, to 1:99 to the amount of phospholipids and sterols, i.e. in a ratio of 0.1:99.9, 0.2:99.8, 0.3:99.7, 0.4:99.6, 0.5:99.5, 0.6:99.4, 0.7:99.3, 0.8:99.2, 0.9:99.1, or 1.0:99.0. In particular embodiments, the ascorbate ester is present in a ratio of 0.1:99.9 to the amount of phospholipids and sterols.

In further embodiments of the eighteenth aspect, in step b) the mixture of a) is injected with a speed of 1-10 ml/min, i.e. with a speed of 1, 2, 3, 4, 5, 6, 7, 8, 9, or 10 ml/min. In particular embodiments, the mixture is injected with a speed of 5 ml/min.

In further embodiments of the seventeenth aspect, the aqueous phase circulates at a speed of 500-3000 ml/min, i.e. 500, 600, 700, 800, 900, 1000, 1100, 1200, 1300, 1400, 1500, 1600, 1700, 1800, 1900, 2000, 2100, 2200, 2300, 2400, 2500, 2600, 2700, 2800, 2900, or 3000 ml/min. In particular embodiments, the aqueous phase circulates at a speed of 1000-2500, 1500-2500, or 2000-2500 ml/min. In particular embodiments, the aqueous phase circulates at a speed of 2200 ml/min.

In particular embodiments, the aqueous phase is circulated by shear-inducing device. In embodiments, the shear-inducing device is a static mixer or a normal stirrer. In particular the shear-inducing device is a static mixer.

In further embodiments, the static mixer has an internal diameter of 10-15 mm, i.e. of 10, 11, 12, 13, 14, or 15 mm, In particular embodiments, the static mixer has an internal diameter of 12-13 mm, i.e. 12.0, 12.1, 12.2, 12.3, 12.4, 12.5, 12.6, 12.7, 12.8, 12.9, or 13.0 mm. In embodiments, the static mixer is suitable to mix a final volume of 150-300 ml, i.e. 150, 160, 170, 180, 190, 200, 210, 220, 230, 240, 250, 260, 270, 280, 290, or 300 ml, of the liposomal formulation. In particular, the static mixer is suitable to mix a final volume of 170-300 ml, in particular a final volumn of 200-250 ml of the liposomal formulation. Accordingly in particular embodiments the ration between the internal diameter of the static mixer to the volume of the mixed liposomal formulation is 0.7 mm-1 mm, i.e 0.7, 0.8, 0.9, or 1.0 mm, internal diameter per 15 ml of liposomal formulation.

In particular embodiments, in step b) the mixture of a) is injected in front of a shear-inducing device. In particular embodiments, the mixture of a) is injected in front of a static mixer.

In further embodiments, the solvents are eliminated in step c) using filtration, in particular using tangential flow filtration.

In further embodiments, the composition of CD-RAP admixed in step d) comprises 1-10 mg/ml CD-RAP, i.e. 1, 2, 3, 4, 5, 6, 7, 8, 9, or 10 mg/ml CD-RAP. In particular embodiment, the composition comprises 2-9, 3-8, 4-8, 5-8, or 6-8 mg/ml CD-RAP. In particular embodiments, the composition comprises 7 mg/ml CD-RAP. In further embodiments CD-RAP admixed in step d) is comprised in an arginine phosphate buffer or an arginine citrate buffer as described in detail above.

In further embodiments, the ratio between the liposomal formulation and CD-RAP is 1:1, 1.1:1, 1.2:1, 1.3:1, 1.4:1, or 1.5:1. In particular embodiments the ratio between the liposomal formulation and CD-RAP is 1.2:1.

In embodiments of the eighteenth aspect, the method further comprises step e) freeze-drying the liposomal formulation.

In embodiments of the eighteenth aspect, the method comprises step f) reconstituting the freeze-dried liposomal formulation in an arginine phosphate buffer or an arginine citrate buffer. In embodiments, the freeze-dried liposomal formulation is reconsited in a single step by adding and mixing the full reconstitution volume of the arginine phosphate buffer or an arginine citrate buffer at once. In embodiments, the freeze-dried liposomal formulation is reconsited in two or more subsequent steps by adding parts of the full reconstitution volume of the arginine phosphate buffer or an arginine citrate buffer in two or more subsequent steps, i.e. in a first step half of the volume of the full reconstitution volume of the arginine phosphate buffer or an arginine citrate buffer may be added and mixed and in a second step the second half of the full reconstitution volume of the arginine phosphate buffer or an arginine citrate buffer may be added and mixed. In embodiments, the reconsions comprises two steps wherein in the first step one third of the volume of the full reconstitution volume of the arginine phosphate buffer or an arginine citrate buffer may be added and mixed and in the second step two third of the full reconstitution volume of the arginine phosphate buffer or an arginine citrate buffer may be added and mixed. In embodiments, the reconsitions comprises three steps wherein in each step one third of the full reconstitution volume of the arginine phosphate buffer or an arginine citrate buffer may be added and mixed.

In a nineteenth aspect, the present invention provides a method of reducing the polydispersity of a liposomal formulation comprising the steps of
  a) dissolving at least one lipid in an organic solvent,
  b) injecting the mixture of step a) into a circulating aqueous phase, and
  c) eliminating the solvent.

In embodiments of the nineteenth aspect, the method further comprises step d) mixing the liposomal formulation obtained by steps a-c) with a composition comprising CD-RAP. Thereby, the pre-formed liposomes are spiked with CD-RAP.

In embodiments, the organic solvent of step a) is a class 3 solvent. In particular the solvent is selected from the group consisting of acetic acid, acetone, anisole, 1-butanol, 2-butanol, butyl acetate, tert-butylmethyl ether, cumene, dimethyl sulfoxide, ethanol, ethyl acetate, ethyl ether ethyl formate, formic acid, heptane, isobutyl acetate, isopropyl acetate, methyl acetate, 3-methyl-1-butanol, methylethylketone, methylisobutylketone, 2-methyl-I-propanol, pentane, 1-pentanol, 1-propanol, 2-propanol, propyl acetate, more preferably 1-propanol.

In embodiments of the nineteenth aspect, the at least one lipid of step a) is selected from the group consisting of glycerides, glycerophospholipides, glycerophosphinolipids, glycerophosphonolipids, sulfolipids, sphingolipids, phospholipids, isoprenolides, steroids, stearines, steroles and carbohydrate containing lipids. In particular embodiments, the at least one lipid is selected from the group consisting of phosphatidic acid (PA), phosphatidylethanolamine (PE), phosphatidylcholine (PC), phosphatidylserine (PS), and phosphoinositides such as phosphatidylinositol (PI), phosphatidylinositol phosphate (PIP), phosphatidylinositol bisphosphate (PIP2), phosphatidylinositol triphosphate (PIP3), cardiolipin, lysophospholipids, and cholesterol. In particular embodiments, the at least one lipid is a combination of two lipids, in particular a combination of phosphatidylcholine and cholesterol.

In embodiments of the nineteenth aspect, in step a) two or more lipids are dissolved in the organic solvent. In particular embodiments, the lipids phosphatidylcholine and cholesterol are dissolved in the organic solvent. In particular, the ration between lipids and organic solvent is 3:1.

In further embodiments, the total concentration of lipids in the solvent is 0.02 to 0.4 g/ml, i.e. 0.02 g/ml, 0.03 g/ml, 0.04 g/ml, 0.05 g/ml, 0.06 g/ml, 0.07 g/ml, 0.08 g/ml, 0.09 g/ml, 0.10 g/ml, 0.11 g/ml, 0.12 g/ml, 0.13 g/ml, 0.14 g/ml, 0.15 g/ml, 0.16 g/ml, 0.17 g/ml, 0.18 g/ml, 0.19 g/ml, 0.2 g/ml, 0.21 g/ml, 0.22 g/ml, 0.23 g/ml, 0.24 g/ml, 0.25 g/ml, 0.26 g/ml, 0.27 g/ml, 0.28 g/ml, 0.29 g/ml, 0.30 g/ml, 0.31 g/ml, 0.32 g/ml, 0.33 g/ml, 0.34 g/ml, 0.35 g/ml, 0.36 g/ml, 0.37 g/ml, 0.38 g/ml, 0.39 g/ml, or 0.4 g/ml. In particular embodiments, the total concentration of lipids in the solvent is 0.03-0.3 g/ml, 0.03-0.1 g/m10.03-0.05 g/ml. In particular embodiments, the total concentration of lipids in the solvent is 0.033 g/ml.

In further embodiments of the nineteenth aspect, in addition to the at least one lipid in step a) a hydrophobic ascorbate ester is dissolved in the organic solvent. In particular embodiments, the hydrophobic ascorbate ester is ascorbyl palmiate, In further embodiments, the ascorbate ester is present in a ratio of 0.1:99.9, to 1:99 to the amount of phospholipids and sterols, i.e. in a ratio of 0.1:99.9, 0.2:99.8, 0.3:99.7, 0.4:99.6, 0.5:99.5, 0.6:99.4, 0.7:99.3, 0.8:99.2, 0.9:99.1, or 1.0:99.0. In particular embodiments, the ascorbate ester is present in a ratio of 0.1:99.9 to the amount of phospholipids and sterols.

In further embodiments of the nineteenth aspect, in step b) the mixture of a) is injected with a speed of 1-10 ml/min, i.e. with a speed of 1, 2, 3, 4, 5, 6, 7, 8, 9, or 10 ml/min. In particular embodiments, the mixture is injected with a speed of 5 ml/min.

In further embodiments of the nineteenth aspect, the aqueous phase circulates at a speed of 500-3000 ml/min, i.e. 500, 600, 700, 800, 900, 1000, 1100, 1200, 1300, 1400, 1500, 1600, 1700, 1800, 1900, 2000, 2100, 2200, 2300, 2400, 2500, 2600, 2700, 2800, 2900, or 3000 ml/min. In particular embodiments, the aqueous phase circulates at a speed of 1000-2500, 1500-2500, or 2000-2500 ml/min. In particular embodiments, the aqueous phase circulates at a speed of 2200 ml/min.

In particular embodiments, the aqueous phase is circulated by shear-inducing device. In embodiments, the shear-inducing device is a static mixer or a normal stirrer. In particular the shear-inducing device is a static mixer. In embodiments, the static mixer has an internal diameter of 10-15 mm, i.e. of 10, 11, 12, 13, 14, or 15 mm, In particular embodiments, the static mixer has an internal diameter of 12-13 mm, i.e. 12.0, 12.1, 12.2, 12.3, 12.4, 12.5, 12.6, 12.7, 12.8, 12.9, or 13.0 mm. In embodiments, the static mixer is suitable to mix a final volume of 150-300 ml, i.e. 150, 160, 170, 180, 190, 200, 210, 220, 230, 240, 250, 260, 270, 280, 290, or 300 ml, of the liposomal formulation. In particular, the static mixer is suitable to mix a final volume of 170-300 ml, in particular a final volume of 200-250 ml of the liposomal formulation. Accordingly in particular embodiments the ration between the internal diameter of the static mixer to the volume of the mixed liposomal formulation is 0.7 mm-1 mm, i.e 0.7, 0.8, 0.9, or 1.0 mm, internal diameter per 15 ml of liposomal formulation. In particular embodiments, in step b) the mixture of a) is injected in front of a shear-inducing device. In particular embodiments, the mixture of a) is injected in front of a static mixer.

In further embodiments, the solvents are eliminated in step c) using filtration, in particular using tangential flow filtration.

In further embodiments, the composition of CD-RAP admixed in step d) comprises 1-10 mg/ml CD-RAP, i.e. 1, 2, 3, 4, 5, 6, 7, 8, 9, or 10 mg/ml CD-RAP. In particular embodiment, the composition comprises 2-9, 3-8, 4-8, 5-8, or 6-8 mg/ml CD-RAP. In particular embodiments, the composition comprises 7 mg/ml CD-RAP. In further embodiments CD-RAP admixed in step d) is comprised in an arginine phosphate buffer or an arginine citrate buffer as described in detail above.

In further embodiments, the ratio between the liposomal formulation and CD-RAP is 1:1, 1.1:1, 1.2:1, 1.3:1, 1.4:1, or 1.5:1. In particular embodiments the ratio between the liposomal formulation and CD-RAP is 1.2:1.

In embodiments of the nineteenth aspect, the method further comprises step e) freeze-drying the liposomal formulation.

In embodiments of the nineteenth aspect, the method comprises step f) reconstituting the freeze-dried liposomal formulation in an arginine phosphate buffer or an arginine citrate buffer. In embodiments, the freeze-dried liposomal formulation is reconsited in a single step by adding and mixing the full reconstitution volume of the arginine phosphate buffer or an arginine citrate buffer at once. In embodiments, the freeze-dried liposomal formulation is reconsited in two or more subsequent steps by adding parts of the full reconstitution volume of the arginine phosphate buffer or an arginine citrate buffer in two or more subsequent steps, i.e. in a first step half of the volume of the full reconstitution volume of the arginine phosphate buffer or an arginine citrate buffer may be added and mixed and in a second step the second half of the full reconstitution volume of the arginine phosphate buffer or an arginine citrate buffer may be added and mixed. In embodiments, the reconsitions comprises two steps wherein in the first step one third of the volume of the full reconstitution volume of the arginine phosphate buffer or an arginine citrate buffer may be added and mixed and in the second step two third of the full reconstitution volume of the arginine phosphate buffer or an arginine citrate buffer may be added and mixed. In embodiments, the reconsitions comprises three steps wherein in each step one third of the full reconstitution volume of the arginine phosphate buffer or an arginine citrate buffer may be added and mixed.

In particular, the following embodiments are provided by the present invention:

1. A CD-RAP precursor protein comprising
   a) a pre-sequence, which comprises at its C-terminus a cleavage site, and
   b) CD-RAP (in particular according to SEQ ID NO: 1 or a variant thereof) or a variant thereof.
2. The precursor protein of aspect 1, wherein the pre-sequence does not disturb the folding of CD-RAP, in particular wherein pre-sequence does not need to be eliminated prior to folding.
3. The precursor protein of aspect 1 or 2, wherein the pre-sequence improves the folding of CD-RAP.
4. The precursor protein of any of the preceding aspects, wherein the pre-sequence has a length of 5-50 amino acids, in particular 7-33 amino acids.
5. The precursor protein of any of the preceding aspects, wherein the pre-sequence comprises an affinity tag, in particular a poly-His tag.
6. The precursor protein of any of the preceding aspects, wherein the pre-sequence has a lower grand average of hydropathy than CD-RAP.
7. The precursor protein of any of the preceding aspects, wherein the precursor protein has a grand average of hydropathy (GRAVY) of less than −0.03 according to Kyte and Doolittle, and/or wherein the pre-sequence has a grand average of hydropathy (GRAVY) of less than −0.2 according to Kyte and Doolittle.
8. The precursor protein of any of the preceding aspects, wherein the cleavage site is an enzymatic cleavage site, in particular a cleavage site for an endopeptidase, in particular a cleavage site for an enterokinase or a protease of mixed nucleophile, superfamily A (PA clan), in particular a R or K amino acid.
9. The precursor protein of aspect 8, wherein the endopeptidase is selected from the group consisting of cysteine protease and serine protease, preferably trypsin or chymotrypsin, more preferably trypsin.
10. The precursor protein of any of the preceding aspects, wherein the pre-sequence comprises at its N-terminus the amino acids MATTX1T, MATTX1TG, MATTX1TGN, MATTX1TGNS or MATTX1TGNSA, wherein X1 is L or S.
11. The precursor protein of any of the preceding aspects, wherein the pre-sequence comprises at its N-terminus the amino acids MATTST, MATTSTG, MATTSTGN, MATTSTGNS or MATTSTGNSA or a variant thereof.
12. The precursor protein of any of the preceding aspects, wherein the pre-sequence comprises or consists of the amino acid sequence selected from the group consisting of SEQ ID NO: 2, SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 18, SEQ ID NO: 18, SEQ ID NO: 19, or a variant thereof.
13. The precursor protein of any of the preceding aspects, wherein the precursor protein comprises or consists of the amino acid sequence according to SEQ ID NO: 20 or a variant thereof.

14. A nucleic acid encoding the precursor CD-RAP protein of any of aspects 1 to 13.
15. A vector comprising the nucleic acid of aspect 14.
16. A host cell comprising, the precursor CD-RAP protein of any of aspects 1 to 13, the nucleic acid of aspect 14, or the vector of aspect 15.
17. The host cell of aspect 16, wherein the host cell is a prokaryotic or eukaryotic cell.
18. The host cell of aspect 16, wherein the host cell is a bacterial cell, in particular an *Escherichia coli* cell.
19. A method of producing native CD-RAP comprising the steps
   a) providing a CD-RAP precursor protein of any of aspects 1 to 13, and
   b) removing the pre-sequence to obtain native CD-RAP.
20. The method of aspect 19 further comprising one or more of the following steps:
   c) folding the CD-RAP precursor protein, and optionally purifying the folded CD-RAP, and
   d) purifying the native CD-RAP.
21. The method of aspect 19 or 20, wherein the CD-RAP precursor protein provided in step a) is present in its primary, secondary or tertiary conformation.
22. The method of aspect 19 to 21, wherein CD-RAP is folded in step c) prior or subsequent to the removal of the pre-sequence in step b), in particular prio to the removal of the pre-sequence in step b).
23. The method of aspect 19 to 22, wherein the precursor CD-RAP is provided in step a) via biotechnological means, in particular from a host cell of aspect 17-19.
24. The method of any of aspects 19 to 23, wherein in step b) the pre-sequence is removed via enzymatic cleavage, in particular via enterokinase cleavage or via endopeptidase cleavage, in particular via trypsin cleavage.
25. The method of aspect 24, wherein the ratio between the proteolytic enzyme, in particular trypsin, and the precursor CD-RAP protein is 0.5-1.5 units of enzyme per mg of protein.
26. The method of any of aspects 19 to 27, wherein step b) is carried for 0.5-20 hours, in particular for 0.5-16 hours, in particular for 4-7 hours.
27. The method of any of aspects 19 to 26, wherein step b) is carried out at a pH between 7 and 9, in particular between 8 and 8.5, in particular at 8.3.
28. The method of any of aspects 19 to 27, wherein step b) is carried out at a temperature of 5-40° C., in particular at 20-25° C.
29. The method of any of aspects 20 to 29, wherein step c) is carried out subsequently to step a) and before step b).
30. The method of any of aspects 19 to 29, wherein step c) comprises the steps
   (i) incubating the precursor CD-RAP protein in a denaturation buffer, and
   (ii) adding the solution obtained in step (i) to a folding buffer.
31. The method of aspect 30, wherein the denaturation buffer comprises DTT, in particular at a concentration of 10 mM.
32. The method of aspect 30 or 31, wherein the folding buffer comprises arginine, in particular at a concentration of 0.5-1 mol/L, particularly of 0.75 mol/L.
33. The method of any of aspects 30 to 32, wherein the solution obtained in step (i) is added drop wise to the folding buffer, in particular over a time frame of 1-3 hours.
34. The method of any of aspects 30 to 32, wherein the solution obtained in step (i) is added at a ratio of 0.5-2 volume %, in particular 1.5 volume %, of the folding buffer per hour.
35. The method of any of aspects 30 to 34, wherein the folding step c) is carried out at a temperature between 5 and 25° C., in particular at 10° C.
36. The method of any of aspects 30 to 35, wherein the folded precursor CD-RAP is purified via chromatography, in particular via HIC chromatography or multimodal (MM) chromatography.
37. The method of any of aspects 30 to 36, wherein the native CD-RAP is purified via chromatography, in particular via ion-exchange chromatography and/or HIC chromatography.
38. A CD-RAP protein preparation comprising a CD-RAP protein having the mature CD-RAP sequence of SEQ ID NO: 1 with a length of 107 amino acids, wherein the ratio of said CD-RAP (107AA) to any other CD-RAP protein present in the CD-RAP protein preparation is 99 wt-%.
39. A CD-RAP protein preparation comprising a CD-RAP (107AA) protein having the mature CD-RAP sequence of SEQ ID NO: 1 with a length of 107 amino acids, which preparation is free of CD-RAP (105AA), having the CD-RAP sequence of SEQ ID NO: 21 with a length of 105 amino acids.
40. The CD-RAP protein preparation of claim 38 or 38, wherein the CD-RAP protein has a melting temperature of 40° C.
41. A composition comprising CD-RAP or a variant thereof, or a CD-RAP protein preparation according to any of aspects 38-41, and at least one positively charged amino acid and a buffer.
42. The composition of aspect 41, wherein the at least one positively charged amino acid prevents the aggregation of CD-RAP.
43. The composition of aspect 41 or 42, wherein the at least one positively charged amino acid is selected from the group consisting of arginine, lysine, histidine and proline.
44. The composition of any of aspects 41 to 43, wherein the buffer prevents the degradation of CD-RAP.
45. The composition of any of aspects 41 to 44, wherein the buffer is selected from the group consisting of citrate buffer, phosphate buffer, histidine buffer and Tris buffer.
46. The composition of any of aspects 41 to 44, further comprising a sugar or an amino sugar.
47. The composition of aspect 46, wherein the sugar is a monosaccharide, disaccharide or trisaccharide, in particular sucrose, maltose, trehalose or raffinose.
48. The composition of aspect 46, wherein the amino sugar is glucosamine, N-methyl-glucosamine, galactosamine or neuraminic acid.
49. The composition of any of aspects 41 to 48, wherein the composition does not comprise ascorbic acid and/or not glycine.
50. The composition of any of aspects 41 to 49, wherein the composition comprises arginine in a concentration of 50-500 mM, in particular 100-350 mM, particularly 100-200 mM, more particularly 200 mM.
51. The composition of any of aspects 41 to 50, wherein the composition comprises histidine in a concentration of 5-100 mM, in particular 10-50 mM, particularly 20-50 mM, more particularly 50 mM.
52. The composition of any of aspects 41 to 51, wherein the composition comprises sodium phosphate in a concentration of 5-100 mM, in particular 10-50 mM, particularly 20-50 mM, more particularly 20 mM.

53. The composition of any of aspects 41 to 52, wherein the composition comprises sodium dihydrogen phosphate in a concentration of 5-100 mM, in particular 10-50 mM, particularly 20-50 mM, more particularly 20 mM.

54. The composition of any of aspects 41 to 53, wherein the composition comprises citrate in a concentration of 5-100 mM, in particular 10-50 mM, particularly 20-50 mM, more particularly 20 mM.

55. The composition of any of aspects 41 to 54, wherein the composition comprises sucrose in a concentration of 5-100 mM, in particular 10-50 mM, particularly 20-50 mM, more particularly 45 mM.

56. The composition of any of aspects 41 to 55, wherein the composition further comprises a negatively charged amino acid, preferably selected from the group consisting of glutamic acid and aspartic acid.

57. The composition of aspect 56, wherein a combination comprises a total concentration of arginine and glutamic acid of 50-500 mM, in particular 100-350 mM, particularly 100-200 mM, more particularly 200 mM.

58. The composition of aspect 56 or 57, wherein the composition comprises a combination of arginine and glutamic acid in a ratio 1:1, in particular 1:1.25, particularly 1:1.5, more particularly 1:2.

59. The composition of any of aspects 41 to 58, wherein the pH value of the composition is between 5.5 and 8.0, in particular between 6.0 and 7.5, particularly 6.0-6.5, more particularly 6.

60. The composition of aspect 59, wherein the pH value of the composition is adjusted using phosphoric acid or hydrogen chloride, in particular phosphoric acid.

61. The composition of any of aspects 41 to 60, wherein the concentration of CD-RAP or the variant thereof is between 1-10 mg/ml, in particular between 2-5 mg/ml.

62. The composition of any of aspects 41 to 61, wherein the composition comprises 2 mg/ml CD-RAP or a variant thereof, 20 mM citrate, 200 MM arginine, and has a pH value of 6.

63. The composition of any of aspects 41 to 62, for use in a method of in treating and/or preventing cartilage disease or injury in patients suffering from aggrecan degradation, and/or increased influx of water into the cartilage, and/or decreased CD-RAP expression, 64. The composition of any of aspects 41 to 60 for intravenous and/or intra-articular administration.

65. A method of producing a composition of any of aspects 41 to 64, comprising adding CD-RAP or a variant thereof to a buffer comprising at least one positively charged amino acid.

66. A method of storing CD-RAP, comprising keeping CD-RAP in a buffer comprising at least one positively charged amino acid.

67. The method of aspect 66, wherein CD-RAP is stored at a temperature of −80° C. to 40° C., in particular at −20° C. to 25°, particularly at −20° C. to 5° C.

68. The method of aspect 66 or 67, wherein CD-RAP is stored for a time period of up to 6 months, in particular up to 3 months, particularly up to 1 months.

69. A pharmaceutical comprising a composition of any of aspects 41 to 64.

70. A composition comprising liposomes comprising encapsulated CD-RAP or a variant thereof, wherein the size of the liposomes is below 200 nm, in particular below 150 nm, in particular below 120 nm, in particular below 100 nm.

71. The composition of aspect 70, wherein more than 20%, in particular at least 30%, in particular at least 40%, in particular 40%-80%, of total CD-RAP are encapsulated in the liposomes.

72. The composition of any of aspects 70 to 71, wherein the ratio of CD-RAP to liposomes is 1:0.5, 1:0.6, 1:0.7, 1:0.8, 1:0.9, 1:1, 1:1.1, 1:1.2, 1:1.31:1.4, 1:1.5.

73. The composition of any of aspects 70 to 72, wherein the polydisperity index (PDI) of the liposomes is below 0.3, in particular below 0.2, in particular below 0.15, in particular 0.132.

74. The composition of any of aspects 70 to 73, wherein the CD-RAP and the liposomes are present in a phosphate buffer or a citrate buffer containing at least one positively charged amino acid.

75. The composition of aspect 74, wherein the at least one positively-charged amino acid is selected from the group consisting of arginine, histidine, and lysine.

76. The composition of aspect 75, wherein histidine is present in an amount of 50-500 mM, in particular 100-400 mM, in particular 20 mM.

77. The composition of any of aspects 74 to 76, wherein the amount of citrate in the citrate buffer is 10-100 mM, in particular 10-50 mM, in particular 20 mM.

78. The composition of any of aspects 70 to 77, wherein the liposomes are composed of lipids selected from the group consisting of glycerides, glycerophospholipides, glycerophosphinolipids, glycerophosphonolipids, sulfolipids, sphingolipids, phospholipids, isoprenolides, steroids, stearines, steroles and carbohydrate containing lipids, in particular phosphatidyl choline and cholesterol.

79. The composition of aspect 78, wherein the lipids phosphatidyl choline and cholesterol, are present in a ratio of 74.8:25.1.

80. The composition of aspect 78 or 79, wherein the liposomes further comprise an hydrophobic ascorbate ester, in particular ascorbyl palmiate.

81. The composition of any of aspects 78 to 80, wherein the ascorbate ester is present in a ratio of 0.1:99.9 to the amount of phospholipids and sterols.

82. The composition of any of aspects 70 to 81, for use in a method of in treating and/or preventing cartilage disease or injury in patients suffering from aggrecan degradation, and/or increased influx of water into the cartilage, and/or decreased CD-RAP expression.

83. The composition of any of aspects 70 to 82, for intra-articular administration.

84. A pharmaceutical comprising the composition of any of aspects 70 to 83.

85. A method of producing a liposomal formulation comprising the steps of
a) dissolving at least one lipid in an organic solvent,
b) injecting the mixture of step a) into a circulating aqueous phase, and
c) eliminating the solvent.

86. The method of aspect 85, further comprising step d) mixing the liposomal formulation obtained by steps a-c) with a composition comprising CD-RAP. Thereby, the pre-formed liposomes are spiked with CD-RAP.

87. The method of aspect 85 or 86, wherein the organic solvent is a class 3 solvent, preferably selected from the group consisting of acetic acid, acetone, anisole, 1-butanol, 2-butanol, butyl acetate, tert-butylmethyl ether, cumene, dimethyl sulfoxide, ethanol, ethyl acetate, ethyl ether ethyl formate, formic acid, heptane, isobutyl acetate, isopropyl acetate, methyl acetate, 3-methyl-1-butanol, methylethylketone, methylisobutylketone, 2-methyl-1- propanol, pentane, 1-pentanol, 1-propanol, 2-propanol, propyl acetate, more preferably 1-propanol.

88. The method of any of aspects 85 to 87, wherein the at least one lipid is selected from the group consisting of glycerides, glycerophospholipides, glycerophosphinolipids, glycerophosphonolipids, sulfolipids, sphingolipids, phospholipids, isoprenolides, steroids, stearines, steroles and carbohydrate containing lipids, in particular phosphatidyl choline and cholesterol.

89. The method of any of aspects 85 to 88, wherein in step a) two or more lipids are dissolved in the organic solvent.

90. The method of aspect 89, wherein the lipids phosphatidyl choline and cholesterol are dissolved in the organic solvent, in particular in a ratio of 3:1.

91. The method of any of aspects 85 to 90, wherein the total concentration of lipids in the solvent is 0.02 to 0.4 g/ml, in particular 0.03-0.3 g/ml, in particular 0.033 g/ml.

92. The method of any of aspects 85 to 91, wherein in addition to the at least one lipid in step a) an hydrophobic ascorbate ester, in particular ascorbyl palmiate, is dissolved in the organic solvent.

93. The method of aspect 92, wherein the ascorbate ester is present in a ratio of 0.1:99.9 to the at least one lipid(s).

94. The method of any of aspects 85 to 93, wherein in step b) the mixture of a) is injected with a speed of 1-10 ml/min, in particular 5 ml/min.

95. The method of any of aspects 85 to 94, wherein the aqueous phase circulates at a speed of 500-3000 ml/min, in particular 1000-2500, in particular at 2200 ml/min.

96. The method of any of aspects 85 to 95, wherein aqueous phase is circulated by a shear-inducing device, in particular a static mixer, in particular having a diameter of 10-15 cm, in particular 12.6 cm.

97. The method of any of aspects 85 to 96, wherein in step b) the mixture of a) is injected in front of a shear-inducing device, in particular in front of a static mixer.

98. The method of any of aspects 85 to 97, wherein the solvents are eliminated in step c) using filtration, in particular using tangential flow filtration.

99. The method of any of aspects 85 to 98, wherein the composition of CD-RAP admixed in step d) comprises 1-10 mg/ml CD-RAP, in particular 7 mg/ml, in particular in an arginine phosphate buffer or an arginine citrate buffer.

100. The method of aspect 99, wherein the ratio between the liposomal formulation and CD-RAP is 1.2:1.

101. The method of any of aspects 85 to 100, further comprising step e) freeze-drying the liposomal formulation.

102. The method of aspect 101, further comprising step f) reconstituting the freeze-dried liposomal formulation in an arginine phosphate buffer or an arginine citrate buffer.

103. A liposomal formulation producible by the method of any of aspects 85-102.

104. A method of storing CD-RAP, comprising keeping CD-RAP in a liposomal composition as specified in any of aspects 70 to 83.

105. The method of aspect 104, wherein CD-RAP is stored at a temperature of −80° C. to 40° C., in particular at −20° C. to 25°, in particular at 5° C.

106. The method of aspect 104 or 105, wherein CD-RAP is stored for a time period of up to 6 months, in particular up to 3 months, in particular up to 1 months.

107. A method of reducing the size of liposomes in a liposomal formulation comprising the steps of
a) dissolving at least one lipid in an organic solvent,
b) injecting the mixture of step a) into a circulating aqueous phase, and
c) eliminating the solvent.

108. A method of reducing the polydispersity of a liposomal formulation comprising the steps of
a) dissolving at least one lipid in an organic solvent,
b) injecting the mixture of step a) into a circulating aqueous phase, and
c) eliminating the solvent.

The invention is described in more detail in the examples and figures that are not to be understood as limiting the scope of present invention.

EXAMPLES

Example 1: Production and Isolation of CD-RAP Precursor Proteins

The following constructs of the cartilage-derived retinoic acid protein CD-RAP comprising a ore-sequence are designed

| Construct | Pre-sequence |
| --- | --- |
| pINTrap2-9 | MATTSTGNSARFVNQHLHHHHHHHHGGGENQQQR |
| pINTrap-3 | MATTSTGNSAR |
| pINTrap-4 | MATTSTR |
| pINTRap12-9 | MATTSTLTTHWHWHGNSAR |
| pINTrap15-9 | MATTSTGNSAHFQHHHGSLAR | a) Expression

An *E. coli* strain type BL21 was used, comprising a pET-52b-II plasmid, comprising a nucleotide sequence encoding the above-specified CD-RAP precursor proteins (i.e. comprising the respective pre-sequence and the sequence of CD-RAP according to SEQ ID NO: 1), and an Ampicillin resistance. The strain was cultivated in pre-culture in LB and in a glucose-feeded main culture in a fermenter with minimal medium at 37° C. at pH 7.0.

b) Lysis, dissolution and capturing of Pre-CD-RAP

The cells were harvested and lysed twice by a french press, the lysate comprising the fusion protein within inclusion bodies was washed twice with water and centrifuged.

For denaturation, 28.5 g of the fusion protein of about 27 g/L was put into a beaker, then a mixture of 6 M Gua-HCl, 2 mM EDTA, 10 mM DTT, 50 mM Tris/HCl at a pH 8.3, was added, It was agitated for 2 h at ambient temperature. The solution was dark brown and somewhat turbid.

c) Folding of Pre-CD-RAP

For the refolding step a mixture of 0.75 M arginine, 1 mM EDTA, 1 mM glutathione red. 0.5 mM glutathione oxid at pH 8.3 was prepared. The solution with the denaturated Pre-CD-RAP was slowly poured into this mixture, then it was agitated for 16 h at ambient temperature. 0.61 g/L of folded Pre-CD-RAP were obtained.

d) Capturing of Pre-CD-RAP

Ammoniumsulfate was added until a conductivity of 80 mS/cm was attained. Adepth filtration and a 0.2 μm filtration were carried out. The capturing step itself was done with a hydrophobic interaction chromatography. The column had a diameter 2.6 cm and was filled to a height 26 cm with the adsorbent Toyopearl Butyl 650 (comp. Tosoh). 0.90 L of filtrated solution was applied onto the column. The equilibrium buffer was water with 50 mM NaHPO$_4$/0.5 M NH4SO$_4$ at pH 7.0 and the elution buffer was water, containing 50 mM NaHPO$_4$ at pH 7.0. The elution volume was collected in fractions. The fractions containing Pre-CD-RAP were combined, the volume of this pool was 0.35 L. The concentration in it of Pre-CD-RAP was 0.70 g/L. The yield after the capture chromatography was 47%.

e) Removal of the pre-sequence

The enzymatic cleavage took place in the eluate of the HI-Chromatography (Na-acetate at pH 4.5), which was adjusted to pH 8.3 by NaOH. For the cleavage, the endoprotease trypsine (porcine trypsin), manufactured recombinantely in *E. coli*, was used. The cleavage was carried out in the eluate from the capturing-chromatography (Pre-CD-RAPAP dissolved in) whose pH was raised to 8.3 by sodium hydroxide. 164 µL of trypsine solution were added to the solution, the objective was to take 1 unit of enzyme per mg of protein. The solution was agitated for 16 h at ambient temperature.

The cleavage was assessed by HPLC-chromatography, which showed a separate peak to the CD-RAP (see FIG. 2).

Figure 4:
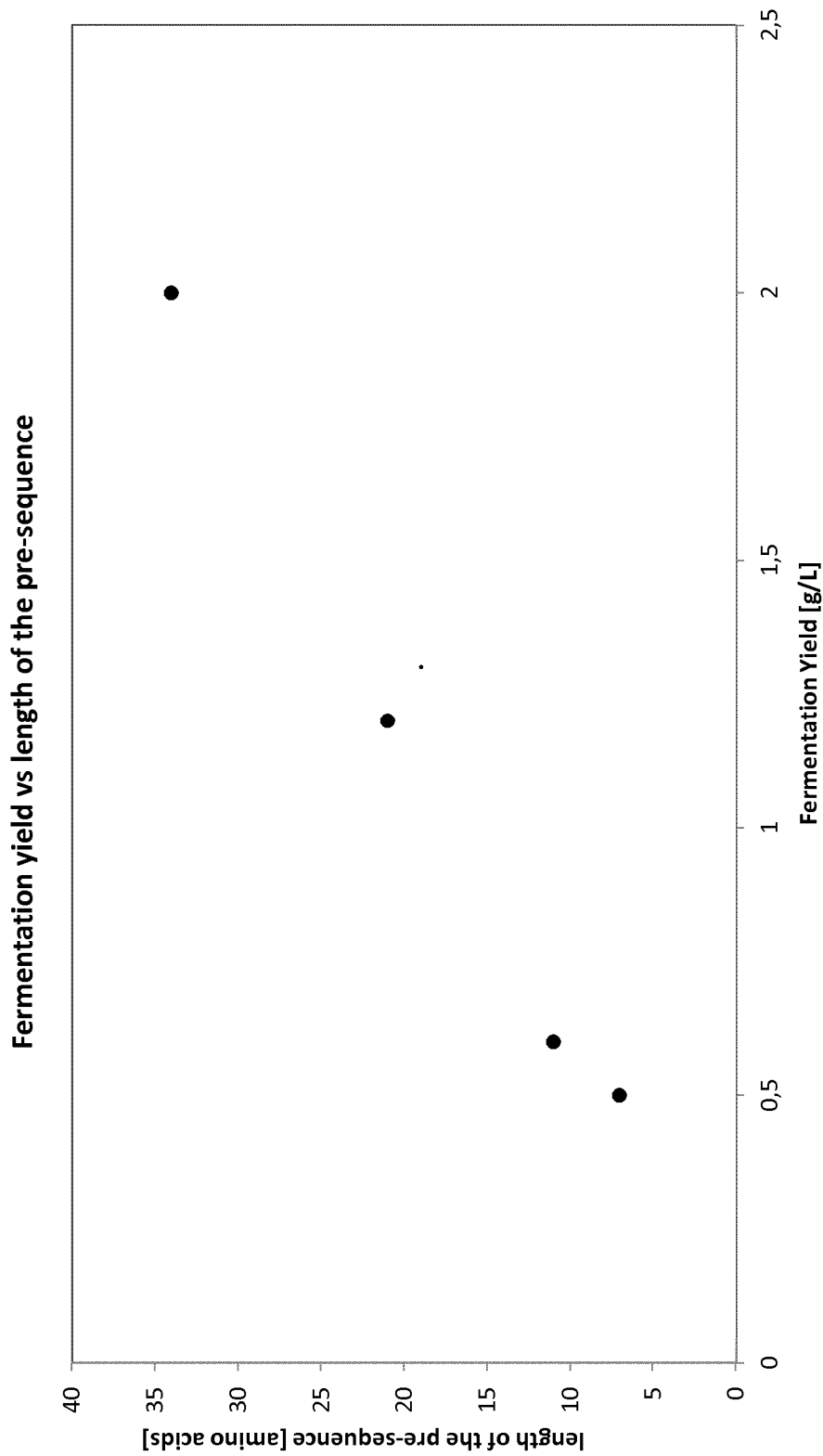

Depending on the length of the pre-sequence, different over-all concentrations of native CD-RAP were obtained in that higher yields were obtained from CD-RAP constructs comprising longer pre-sequences (see FIGS. 3 and 4).

Example 2: Cleavage Parameters

To find the optimal set of parameters for the cleavage of precursor CD-RAP, the following parameters were investigated:

a) Enzyme Concentration

To investigate the dependency of the cleavage from the concentration of trypsin, trials were performed to monitored cleavage at different trypsin concentrations.

Figure 5:
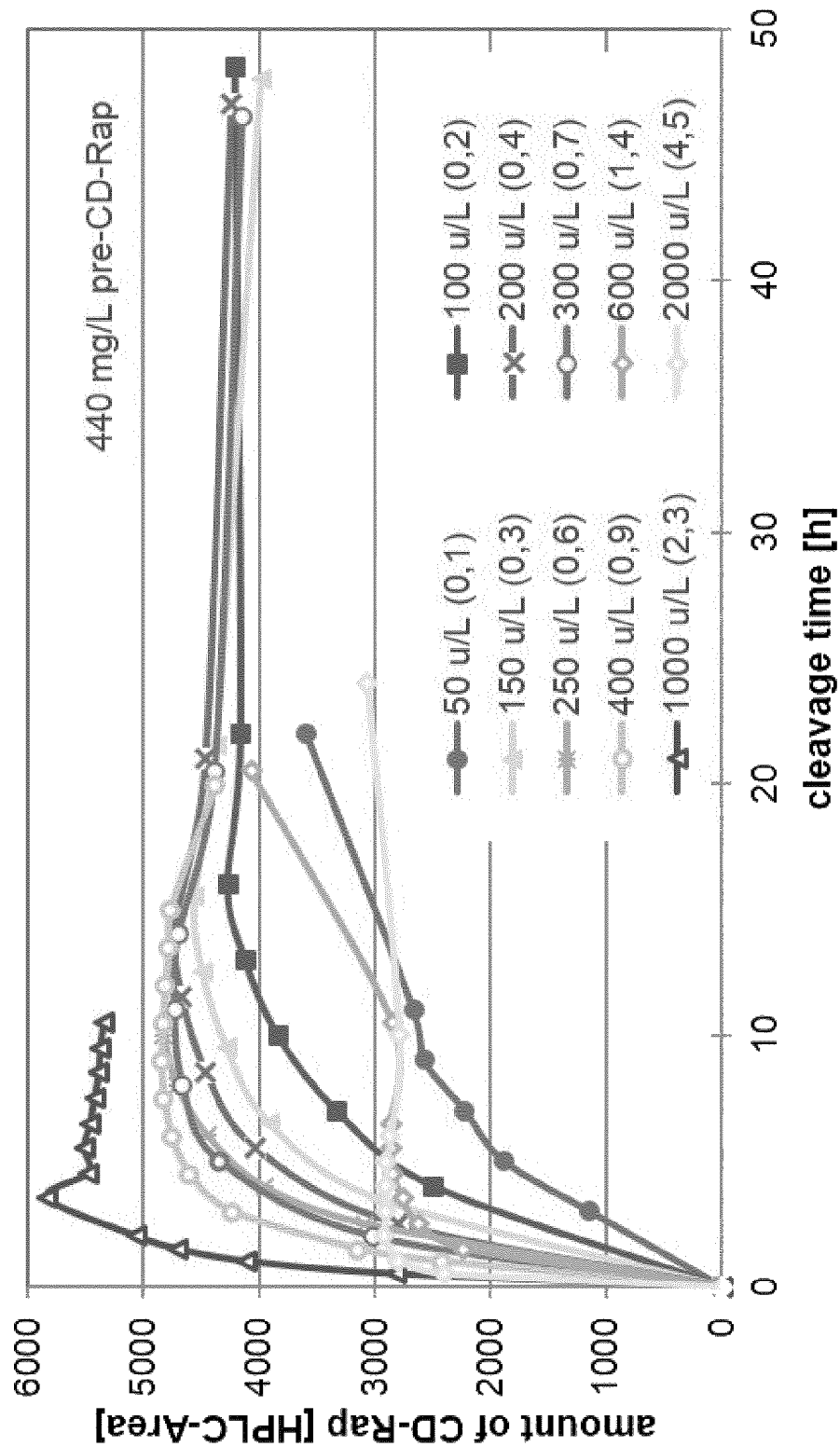

A known Pre-CD-RAP concentration of 441.8 mg/L was used set from pH 4.1 to 8.3 by NaOH. The solution was then divided into ten portions, which were shaken at ambient temperature (23-25° C.). To each portion a different amount of trypsin (50, 100, 150, 200, 250, 300, 400, 600, 1000, or 2000 u/L) was added and samples were taken to monitor the cleavage by HPLC. The results are shown in FIG. 5.

b) pH-Value

The influence of the pH-value to the cleavage was studied with a trypsin concentration of 250 units/mL (calculated with the initial activity value of 9615 units/mL trypsin-solution) and a Pre-CD-RAP content of 0.24 g/L. Nine portions of this solution were taken at set by HCl and NaOH to pH 3, 4, 5, 6, 7, 8, 9, 10 and 11. The cleavage was stirred at 25° C. in a falcon tube. In different intervals samples were taken for investigation by HPLC. The diagram FIG. 6 shows the decrease of the Pre-CD-RAP content (expressed as area of the HPLC peak) for the different pH values. It can be observed, that the cleavage does not work at pH 5 or lower, at pH 6 it takes place, but slowly. At pH 8.3 and higher the cleavage is quick, but the amount of CD-RAP drops after having a maximum, probably due to a digest of CD-RAP by trypsin, now possible by an exposing of trypsin cleavage sites, which are hidden inside the room structure of the protein at lower pH values. The conclusion is, that the pH of the cleaving step is ideal between 7 and 8. When the cleaving should take place at shorter times, a pH about 8.0 to 8.3 is to prefer, but in this case it should be taken care, that the trypsin is removed within 10 h, otherwise a digest of CD-RAP is possible. When the cleavage shall take place in a longer time period, a pH-value of 7.0 and a removal of the trypsin after 20 h is to prefer.

c) Temperature

The influence of the temperature to the trypsin cleavage was tested. The same Pre-CD-RAP solution was used and 1.25 units of trypsin per mL of solution were applied. The only variation was the temperature; which was changed from 5 to 40° C. in steps of 5° C. The trial was carried out in 2.0 mL tubes in a shaker with adjustable temperature. The progress of the cleavage was monitored in different time intervals by HPLC. The results are shown in the diagrams below. FIG. 7 shows the decrease of the area of the Pre-CD-RAP peak in the HPLC-chromatogram. A decrease takes place at every temperature (but this may be caused also by other reasons, as precipitation). This decrease is faster at higher temperatures. At higher temperatures a complete disappearance of Pre-CD-RAP after about 24 h was found, whereas at low temperatures a certain residue of pre CD-RAP seems to persist also after the double of time. In general it appears, that, with the applied conditions, the yield is higher at lower temperatures, but it takes much longer to get there. The consequence from the data is that a cleavage temperature of 20-25° C. seems to be a good working range.

Example 3: Stability of Different CD-RAP Constructs

Different rhCD-RAP constructs which differ in their primary sequence as well in their formulation, were characterized physicochemically with regard to their thermostability and stress stability.

TABLE 1

| rhCD-RAP constructs | | | |
|---|---|---|---|
| CMC-B-0052 | *E. coli* | major 108 AS with N-terminal methionine | 350 mM L-arginine pH 7.4 |
| 0709-CF-CK01 | *E. coli* | major 108 AS with N-terminal methionine | 350 mM L-arginine pH 7.4 |
| F-MPL-120004.01 | *E. coli* | 107 AS without N-terminal methionine | 50 mM NaH$_2$PO$_4$, 350 mM L-arginine, pH 7.4 |
| G25-Q131 # 002 | *K. lactis* | 107 AS without N-terminal methionine | 50 mM NaH$_2$PO$_4$, 200 mM L-arginine, pH 7.5 |
| G25-Q131 # 003 | *K. lactis* | 107 AS without N-terminal methionine | 50 mM NaH$_2$PO$_4$, 200 mM L-arginine, pH 7.5 |

To discriminate the effects of different rhCD-RAP constructs a determination of the melting point by differential scanning fluorometry (DSF) was performed wherein the fluorescence intensity versus temperature is recorded in the denaturation process of the protein in the presence of SYPRO orange. Through unfolding of protein hydrophobic patches become exposed and strong fluorescent light of 610 nm is emitted by the dye molecules bound to them. The degree of protein unfolding is monitored by HEX channel that captures the spectral properties of Sypro Orange-unfolded protein complexes (excitation 515-535 nm, emission 560-580 nm).

The samples of the different rhCD-RAP constructs were dialyzed overnight into the 2 buffer systems (dialysis chambers: D-tube Dialyzer Midi, MWCO 6-8 kDa from Novagen, No. 71507-3) and the concentration was fixed to 1.0 mg/mL by dilution with the corresponding buffer.

Buffer Preparation:

350 mM L-Arginine Phosphate, pH 7.5

121.94 g L-Arginine were diluted in approx. 1.8 L water, pH was adjusted with 85%) Phosphoric acid to a pH 7.5 and filled up with pure water to a final volume of 2 L.

200 mM L-Arginine, 50 mM NaH$_2$PO$_4$, pH 7.5

69.68 g L-Arginine and 15.60 g NaH$_2$PO$_4$×2 H$_2$O were diluted in approx. 1.8 L water, pH adjusted with 85% Phosphoric acid to a pH 7.5 and filled up with pure water to a final volume of 2 L.

Each buffer was mixed with Sypro Orange dye (2 μL dye+48 μL buffer=200×Sypro Orange). Each rhCD-RAP sample (1.0 mg/mL rhCD-RAP) was diluted to an end concentration of 0.5 mg/mL and 0.1 mg/mL with three replicas each (with a 10× Sypro Orange concentration.

All samples were measured once with three replicas each. Using the Real-Time PCR detection system CFX96 Touch (Bio-Rad), the proteins were incubated in a thermal gradient from 25° C. to 95° C. at an incensement of 1° C. and 30 sec hold intervals. The degree of protein unfolding was monitored by HEX channel that captured the spectral properties of Sypro Orange-unfolded protein complexes (excitation 515-535 nm, emission 560-580 nm). The data were analyzed by CFX Manager Software and the melting temperatures were determined using the first derivative spectra.

Surprisingly a significantly lower melting temperature of 53° C. was detected in the product CMC-B-0052, whilst other tested rhCD-RAP batches (F-MPL.120004.001 and G25-Q131#003) showed higher melting points with about 54° C. 56° C. This difference of 3° C. was demonstrated in 2 different formulations. Results are shown below in Table 2 and in FIG. 8

TABLE 2

Melting point determination of different rhCD-RAP batches in two buffer systems by DSF; assay concentration of 0.5 mg/mL

| | 0.5 mg/mL rhCD-RAP Sample batch | | | | | |
|---|---|---|---|---|---|---|
| | F-MPL-120004.01 | F-MPL-120004.01 | CMC-B-0052 | CMC-B-0052 | G25-Q131 #003 | G25-Q131 #003 |
| | | | buffer | | | |
| | 350 mM L-Arginine buffer, pH 7.5 | 200 mM L-Arginine, 50 mM NaH$_2$PO$_4$ buffer, pH 7.5 | 350 mM L-Arginine buffer, pH 7.5 | 200 mM L-Arginine, 50 mM NaH$_2$PO$_4$ buffer, pH 7.5 | 350 mM L-Arginine buffer, pH 7.5 | 200 mM L-Arginine, 50 mM NaH$_2$PO$_4$ buffer, pH 7.5 |
| #1 | 56.0 | 56.0 | 53.0 | 53.0 | 56.0 | 56.0 |
| #2 | 56.0 | 55.0 | 53.0 | 53.0 | 56.0 | 56.0 |
| #3 | 56.0 | 55.0 | 54.0 | 53.0 | 56.0 | 56.0 |
| Mean | 56.0 | 55.3 | 53.3 | 53.0 | 56.0 | 56.0 |
| SD | 0.0 | 0.6 | 0.6 | 0.0 | 0.0 | 0.0 |

Example 4

Five formulations were prepared with concentration of CD-RAP of 5 mg/ml.

Non formulated, non-concentrated CD-RAP was included in the analyses as reference (Formulation 0). An overview of the composition of the formulations can be found in Table 3.

TABLE 3

Formulations prepared in Round 1

| Form. | Buffer | pH Stabiliser* | Cryoprotectant | Remarks |
|---|---|---|---|---|
| 0 | Sodium phosphate 50 mM | 7.4 Arginine 350 mM | NA | Reference formulation |
| 1 | Sodium phosphate 20 mM | 6.5 Arginine 200 mM | NA | Effect of pH |
| 2 | Citrate 20 mM | 6.5 Arginine 200 mM | NA | Effect of buffer type and pH |

TABLE 3-continued

Formulations prepared in Round 1

| Form. | Buffer | pH Stabiliser* | Cryoprotectant | Remarks |
|---|---|---|---|---|
| 3 | Histidine 20 mM | 6.5 Arginine 200 mM | NA | Effect of buffer type and pH |
| 4 | Sodium phosphate 20 mM | 7.4 Arginine 100 mM/Glutamic acid 100 mM | NA | Effect of stabilizer type |
| 5 | Sodium phosphate 20 mM | 7.4 Arginine 200 mM | Sucrose 45 mg/ml | Effect of presence of cryoprotectant |

Prepared buffers are listed in Table 4. Each buffer was prepared as follows:
- 60 ml of the right buffer was poured in a 100 ml glass bottle or beaker
- The required volume of Arg/Glu solution was added, if applicable (see Table 4)
- The required amount of Arginine HCl was added, if applicable (powder, see Table 4)
- The required amount of sucrose was added, if applicable (powder, see Table 4)
- pH was adjusted to target value+/−0.1
- Note: In all cases, pH was adjusted with NaOH 1M.
- The solution was transferred to volumetric flask and volume was completed with the right buffer, the final pH was measured. Buffers were filtered on a 0.2 μm filter.

TABLE 4

Buffers prepared in Round 1

| Buffer | For formulation | Buffer solution* (20 mM) | Arginine/glutamic acid 1M in Na•phosphate buffer (ml) | Arginine HCl (g) | Sucrose (g) |
|---|---|---|---|---|---|
| 1 | 1 | Na Phosphate, pH 6.5 | NA | 4.2 | NA |
| 2 | 2 | Citrate, pH 6.5 | NA | 4.2 | NA |

TABLE 4-continued

Buffers prepared in Round 1

| Buffer | For formulation | Buffer solution* (20 mM) | Arginine/ glutamic acid 1M in Na•phosphate buffer (ml) | Arginine HCl (g) | Sucrose (g) |
|---|---|---|---|---|---|
| 3 | 3 | Histidine, pH 6.5 | NA | 4.2 | NA |
| 4 | 4 | Na Phosphate, pH 7.4 | 20 | NA | NA |
| 5 | 5 | Na Phosphate, pH 7.4 | NA | 4.2 | 4.5 |

*Buffer is the diluent

Buffer exchange was conducted by filtration-centrifugation using Amicon 4 tubes (3 kDa MW cut-off). CD-RAP drug substance (2 ml) was transferred into pre-weighted tubes and an equivalent volume of the appropriate buffer was added. The tubes were centrifuged (4000 g, 15° C.) and the washing process monitored by weighing of the permeate and retentate. Four washing cycles were conducted. During the last centrifugation, a slight concentration was performed (about 10%) in order to obtain 5 mg/ml CDRAP (corrected content of batch F-AKO-120018A used for this round was 4.7 mg/ml). After buffer exchange, part of the sample was aliquoted into 2R glass vials for the stress tests, while the remainder was stored at 5° C. while awaiting t=0 analyses.

T=0 samples were analysed using methods 2-3; 5-9 (Table 5). The t=0 analyses were performed within 48 h after formulation preparation. All formulations (including the reference formulation) were stressed for 7 days at 40° C. This was done by placing the vials in a stability cabinet. In addition, formulations were stressed by freeze/thawing. This was done by storing the vials at −20° C. After 24 h, vials were thawed at ambient temperature for 1 h, and then frozen again for 24 h. Five freeze-thaw cycles were performed in that way. After freeze-thawing the vials were stored at 5° C. while awaiting analysis. All stressed samples were analysed together (i.e. after both stress tests have been completed) with methods 2-3; 5-7 (Table 5). All analyses were conducted within 48 h after the end of the stress tests.

TABLE 5

Analytical methods used in this study

| No. | Parameter | Method |
|---|---|---|
| | Characterisation active | |
| 1 | Total content CD-RAP | UV280 |
| 2 | Content CD-RAP | RP-HPLC |
| 3 | Purity CD-RAP | RP-HPLC |
| 4 | Small aggregates/oligomers and fragmentation CD-RAP | HPSEC |
| 5 | Purity CD-RAP | SDS-Page non reduced |
| 6 | Purity CD-RAP | SDS-Page reduced |
| | General | |
| 7 | Appearance (color, clarity) | Visual inspection |
| 8 | pH | Ph. Eur. 2.2.3 |
| 9 | Osmolality | Ph. Eur. 2.2.35 | pH and osmolality of the formulations were measured at T=0. Results are shown in FIG. 9. It can be seen that the pH of Form. 1 and especially of Form. 2, and 3 was above the target pH of 6.5 (6.7, 7.1, and 7.0, respectively). This indicates that a buffer concentration of 20 mM might be too low to maintain the pH to 6.5 in presence of the protein, which has alkaline properties (pKa 9.3-10.3). In the case of citrate and histidine buffers, pH 6.5 is at the edge of the buffer capacity range of these buffers. A decrease in the pH of the formulations could thus be beneficial if these buffers are selected. At pH 6.0 for example, the buffer capacity of citrate and histidine would probably be sufficient to allow keeping buffer concentration to 20 mM.

Most prepared formulations were hypertonic, with the exception of Form. 4 containing the Arg/Glu mixture. Interestingly, the reference formulation prepared by SCIL was also hypertonic. As expected, the addition of sucrose to the formulation had a significant impact on the osmolality (Form. 5). Given that the target pH was not obtained in Form. 2 and 3, these formulations would be repeated in Round 2 (if judged relevant based on the other results obtained). The osmolality of the formulations was not considered in the preparation of the formulations for Round 1, as the aim of this round was mainly to assess the effect of different excipients on the stability of CD-RAP.

Appearance of the formulations is presented in FIG. 10. At T=0, all formulations were clear and colourless. After 7 days thermal stress, all formulations were turbid, with Form. 4 being the most turbid. In all formulations, the precipitate was sinking at the bottom of the vials over time, indicating that it consisted in large insoluble protein aggregates. It was also observed that Form. 5 containing sucrose had a slightly yellow colour. After 5 freeze-thaw cycles, the formulations had a similar appearance compared to T=0

Results obtained by RP-HPLC with CD-RAP fpr the Main Peak are presented in FIG. 11.

A 10-15% protein loss occurred during the process. This could have been caused by CD-RAP adsorption to the membrane of the Amicon tubes, or by loss of the protein in the permeate (i.e. through the membrane pores). The content of the different formulations was comparable (3.4-3.8 mg/ml), indicating that the protein loss was not linked to the composition of the formulations or to their pH.

When looking at the results obtained for the samples that were stressed for 7 days at 40° C., it can be seen that the performance of the formulations could be rated as follows (from best to worst): Form. 0=2>1=3>4=5. Thus, Form. 2 in citrate buffer performed as well as the reference formulation 0. Form. 4 and 5 containing respectively Arg/Glu and sucrose had the lowest recoveries of CD-RAP main peak after stress compared to T=0. Form. 5 had by far the lowest CD-RAP purity after thermal stress (11.6% in FIG. 11).

After freeze-thaw stress, changes could be observed although they were not as pronounced as those observed after thermal stress. The performance of the formulations could be rated as follows (from best to worst): 3>1=2=4=5<0. Taken together, the results indicate that Form. 0 (reference) was the worst and that the other formulations were generally equivalent. Thus, sodium phosphate buffer showed the worst performance upon freeze-thaw stress, and a trend could be seen as a function of buffer concentration (Form. 1 containing 20 mM sodium phosphate performed better than Form. 0 containing 50 mM of this buffer). This is probably due to the shift in pH that occurs with this buffer upon freezing. The total protein content recovered after stress (3 last columns FIG. 11) was obtained by integrating all the peaks in the chromatograms that were not present in the blank. The recoveries obtained after stress thus represent the material that was not filtered out from the sample by the HPLC column. It can be seen that after thermal stress, the total CD-RAP content varied between 50 and 72%, with the noticeable exception of Form. 4, for which only 20% material was recovered. This is in line with the clarity results, which showed that more precipitation occurred in that formulation. The total amount of CD-RAP obtained after freeze-thaw stress was much higher than after thermal stress and comparable to that measured at T=0. This was expected since no precipitation was observed in these samples. One exception is the reference formulation, which showed a total recovery of 80% after freeze-thaw stress. Since precipitation was not seen in this sample, this might be explained by formation of soluble aggregates.

Example 5

Based on the results obtained in Round 1, six formulations were prepared at a target CD-RAP concentration of 5 mg/ml. In addition, two control formulations were included: non formulated, non concentrated DS (as in Round 1, formulation Oa), as well as non formulated, non concentrated DS which underwent the buffer exchange process (formulation Ob). An overview of the composition of the formulations can be found in Table 6.

TABLE 6

Formulations prepared in Round 2

| Form. | Protein conc. (mg/ml) | Buffer (50 mM) | Stabi- liser | Anti- oxydant (mM)) | Remarks |
|---|---|---|---|---|---|
| 0a | DS batch FHNA- 120045* (7.3 mg/ml) | Sodium phosphate, pH 7.4 | Arg 350 mM | NA | Drug substance (for analysis only, does not need to be prepared) |
| 0b | DS batch FHNA- 120045* (5 mg/ml) | Sodium phosphate, pH 7.4 | Arg 350 mM | NA | Processed DS (no prepa- ration, but needs to undergo the process) |
| 1 | 5 | Potassium phosphate, pH 6.5 | Arg 200 mM | NA | No pH shift upon freezing, lower pH, increased buffer concen- tration |
| 2 | 5 | Potassium phosphate, pH 6.5 | Arg 200 mM | ascorbic acid 2.08 mM* | Compared to formulation 1, addition of an antioxidant |
| 3 | 5 | Citrate pH 6.5 | Arg 200 mM | NA | Compared to formulation 1, effect of buffer type. Repeat form. 2 Round 1, but with higher buffer concen- tration |
| 4 | 5 | Citrate pH 6.5 | Arg 200 mM | ascorbic acid 2.08 mM* | Form. 3 with antioxidant |
| 5 | 5 | Histidine pH 6.5 | Arg 200 mM | NA | Repeat form. 3 Round 1, but with higher buffer concen- tration |
| 6 | 5 | Histidine pH 6.5 | Arg 200 mM | ascorbic acid 2.08 mM* | Form. 5 with antioxidant |

*2.08 mM is equivalent to a 5-fold molar excess compared to the protein

The following factors were investigated in Round 2:
Effect of buffer type at 50 mM, pH 6.5 (sodium phosphate vs. potassium phosphate vs. citrate vs. histidine)
Effect of presence of an antioxidant (ascorbic acid)

Compared to Round 1, buffer concentration was increased to 50 mM. This was done to improve the buffer capacity of the formulations. The pH of all prepared formulations was set to 6.5, as new data obtained at Sanofi indicated that CD-RAP protein was more stable at acidic pH. Stabiliser concentration (arginine) was kept at 200 mM. In this round, arginine base was used in all formulations.

For Round 2, the buffers were prepared differently compared to Round 1. In Round 1, sodium phosphate and histidine buffers were first prepared without any additional excipient, and their pH was adjusted with HCl or phosphoric acid. The other excipients (arginine HCl, Arg/Glu, sucrose) were then added, and pH was adjusted again to target pH with NaOH 1N. In Round 2, the pH of the buffers prior to excipient addition was adjusted with the buffer salts. This resulted in only one pH adjustment step using a strong acid, which was performed at the end, after excipient addition. It was anticipated that preparing the buffers in this way will have a beneficial impact on the osmolality of the formulations, which was quite high in Round 1. More specifically, the buffers of Round 2 were prepared as follows:

For the potassium phosphate buffer, a solution of KH2PO4 salt was prepared. This solution was titrated with a solution of K2HPO4 until pH 6.5 was reached. A defined volume of buffer solution was withdrawn, and arginine (base) and ascorbic acid (if applicable) were added. pH was adjusted back to 6.5 with phosphoric acid. The buffer was then transferred to a volumetric flask and volume complete with water.

For the citrate buffer, a solution of citric acid was prepared. This solution was titrated with a solution of sodium hydroxide 1 M until pH 6.5 was reached. Arginine (base) and ascorbic acid (if applicable) were added. pH was adjusted back to 6.5 with hydrochloric acid (HCl). The buffer was then transferred to a volumetric flask and volume complete with water.

For the histidine buffer, the procedure was the same as that used for the other 2 buffers, with the exception that histidine consists in a single salt, thus the first titration step did not take place. As for citrate buffer, pH of the histidine buffer was adjusted with HCl.

After preparation, the final pH of each buffer was measured, and the solutions were filtered on 0.2 μm filter Formulations were prepared using the same process as that described in Example 4. Prior to buffer exchange, all formulation except Form. Oa were diluted with their corresponding buffer to a concentration of 5.5 mg/ml. This concentration was chosen to compensate for the 10% protein loss that occurred during the process, as suggested by the T=0 results obtained by RP-HPLC in Round 1. After the third washing step (e.g. after addition of the last 2 ml buffer), the pH of the formulations was adjusted to target value using diluted HCl solutions. Preliminary tests were conducted on the buffers to determine the appropriate HCl concentrations that should be used. Results of the in-process pH adjustment are shown in FIG. 12.

T=0 samples were analysed using methods 2-3; 5; 7-9 (Table 5). The t=0 analyses were performed within 48 h after formulation preparation. Stress testing was performed as for Round 1, with the difference that the thermal stress (40° C.) was applied for 2 days instead of 7 days. This was done in order to prevent massive precipitation of the protein as observed in Round 1. After the stress period, the samples were stored at 5° C. while awaiting analyses. All stressed samples were analysed together (i.e. after both stress tests have been completed) with methods 2-3; 5; 7 (Table 5). All analyses were conducted within 48 h after the last freeze-thaw cycle.

pH and osmolality results of the formulations prepared in Round 2 can be found in FIG. 13. Both parameters were measured at T=0. It can be seen that in contrast to Round 1, the pH of all formulations was on target, which is the result of the in-process pH adjustment step introduced after the third washing step. Osmolality of Form. 1 and 2 in potassium phosphate buffer, although on the high side, was acceptable. The osmolality of 50 mM potassium phosphate buffer was lower compared to that of the 20 mM sodium phosphate buffer prepared in Round 1. The single pH adjustment step introduced in Round 2 and the use of arginine base instead of arginine HCl led to an improvement in the buffer osmolality. The osmolality of Form. 3-4 and 5-6 prepared respectively in citrate and histidine buffers exceeded the acceptable value of 350 mOsm/kg. In the case of 50 mM citrate buffer, this had to be expected due to the fact that: pH 6.5 is the upper range of the buffer capacity (i.e. conjugated base, trisodium citrate, is mostly present)

Trisodium citrate ionisation degree=4 (i.e. 50 mM trisodium citrate=200 mM ions)+Arg 200 mM=400 mOsm/kg before pH adjustment.

Another reason explaining the high osmolality of the citrate and histidine buffers is that the pH of these buffers was adjusted with HCl instead of with phosphoric acid. It is known from the literature that a strong ionic interaction occurs between arginine and phosphate ions. This interaction can practically be considered as a covalent interaction, and can even withstand fragmentation by mass spectrometric collision-induced dissociation. Due to the formation of this complex, adjusting pH with phosphoric acid will have a much lower impact on the osmolality. Chloride ions do not form this complex and thus the osmolality of Form. 3-6, which pH was adjusted with HCl, was high as seen in FIG. 13. HCl was used in citrate and histidine buffers in order not to introduce additional ions (phosphate) in the formulation. If the final formulation chosen is in one of these buffers, phosphoric acid will be considered to adjust pH.

Appearance of the formulations is presented in FIG. 14. At t=0, all formulations were clear and colourless, with the exception of Form. 6, which was slightly pink. The change in colour was already observed in the buffer, which showed a blackish-red colour a few hours after preparation. This was probably caused by oxidation of the ascorbic acid. The buffer was prepared 3 times and the change in colour was observed every time and so, even if the buffer was protected from light. No incompatibility was documented between ascorbic acid and histidine, so the reason why the other buffers containing ascorbic acid did not change colour so rapidly is unknown. After 2 days stress at 40° C., all formulations were turbid. Compared to Round 1, however, the precipitate did not sink at the bottom of the vials and remained in suspension, indicating that less precipitation had occurred. All formulations containing ascorbic acid (2, 4, and 6) showed also a change in colour, which was more marked in Form. 6. This formulation was also one of the most turbid.

After 5 freeze/thaw cycles, the formulations had the same appearance than at t=0. Results obtained by RP-HPLC are presented in FIG. 15. It can be seen that the content of the formulations at t=0 presented some variability, with Form. 0a, 1, 4, and especially 6 being above the target CD-RAP concentration of 5 mg/ml, and Form. 0b being below. This indicates that the buffer exchange process in Amicon tubes is difficult to control and that in order to obtain an accurate content, IPC should be introduced during the process. After 2 days thermal stress, a significant decrease in CD-RAP content and purity compared to t=0 was observed in the formulations containing ascorbic acid (2, 4, and 6). Interestingly, the decrease in purity was already present in Form. 4 and 6 at t=0. A decrease in purity was also seen in these 3 formulations after 5 freeze-thaw cycles, although to a lesser extent than after thermal stress.

Example 6

6-month stability study performed in order to evaluate the stability of CD-RAP protein with time under the influence of temperature. The compound is intended to be stored at −80° C., −20±5° C., and 5±3° C. (in particular 5° C.). The formulations were stored under different storage conditions (−80° C., −20° C., 5° C., 25° C., and 40° C.). Two batches were used in the stability study. One drug product (DP) batch and one placebo batch matching the DP batch. Both batches are described in Table 7-9:

TABLE 7

Batches placed into the stability study program

| Batch number | Formulation |
| --- | --- |
| F531-03-003P064B (Drug product) | 2 mg/ml CD-RAP, 20 mM citrate buffer pH 6.0, 200 mM arginine |
| F531-03-003P063 (Placebo) | 20 mM citrate buffer pH 6.0, 200 mM arginine |

TABLE 8

Composition of CD-RAP DP batch F531-03-004P064B

| Name of ingredient | g/L | Molarity (mM) | Function |
| --- | --- | --- | --- |
| CD-RAP | 2.0 | 0.17 | Active pharmaceutical ingredient |
| Citric acid monohydrate | 4.203 | 20 | Buffer salt |
| NaOH 1M | 54.39 | NA* | pH adjustment agent |
| L-Arginine base | 34.84 | 200 | Stabiliser |
| Ortho-phosphoric acid | 17.86 | NA* | pH adjustment agent |
| Water for injection (WFI) | 908.7 | NA | Solvent |

*Not in their current form (i.e. dissociated and/or complexed)

TABLE 9

Composition of placebo batch F531-03-004P063

| Name of ingredient | g/L | Molarity (mM) | Function |
|---|---|---|---|
| Citric acid monohydrate | 4.203 | 20 | Buffer salt |
| NaOH 1M | 54.39 | NA* | pH adjustment agent |
| L-Arginine base | 34.84 | 200 | Stabiliser |
| Ortho-phosphoric acid | 17.86 | NA* | pH adjustment agent |
| Water for injection (WFI) | 908.7 | NA | Solvent |

*Not in their current form (i.e. dissociated and/or complexed)

The formulations were tested with the long-term/real-time storage conditions (−80° C., −20° C. and 5° C.) and accelerated storage conditions (25° C. and 40° C.). The stability at −80° C., −20° C., 5° C. and 25° C. were monitored for 6 months. The stability at 40° C. was monitored for 1 month. During the 6 months of the study, the colour and clarity of the sample, pH, osmolality, main band MW and purity did not change at different time points or at various storage temperatures. No aggregates were observed in any of the stability samples over 6 month storage at different temperatures. The placebo corresponding to the CD-RAP drug product (DP) showed no interference with the DP by RP-HPLC, HPSEC and SDS-PAGE analyses. The total viable aerobic count (TVAC) of the samples at release was also within the compendial specification.

Formulations were stored in stability cabinets in upright position in different stability cabinets at −80° C., −20±5° C., 5±3° C., 25±2° C., and 40±2° C. At indicated time points, samples were withdrawn from the cabinets and analyzed within two weeks. While awaiting analysis, samples were stored at 5° C. The parameters and test methods presented in Table 8 below were used to evaluate the stability of the batches.

TABLE 10

| No. | Parameter | Method |
|---|---|---|
| | | Characterisation active |
| 1 | Content CD-RAP | RP-HPLC method QUA-FB-2013-03665 EN-1.0 |
| 2 | Purity CD-RAP | RP-HPLC method QUA-FB-2013-03665 EN-1.0 |
| 3 | Small aggregates/oligomers | HPSEC |
| 4 | Purity CD-RAP | SDS-PAGE (silver staining reduced and non reduced, method versions M-426-e0 and M-416-e2, respectively) |
| | | General |
| 5 | Visible particles | Visual inspection in vial according to Ph. Eur. 2.9.20 and SOP-AP-Visual inspection, V1 |
| 6 | Color | Visual inspection in vial according to Ph. Eur. 2.2.2 and SOP-AP-Visual inspection, V1 |
| 7 | Clarity | Visual inspection in vial according Ph.Eur. 2.2.1 SOP-AP- Visual inspection, V1 |
| 8 | pH | Ph. Eur. 2.2.3 |
| 9 | Osmolality | Ph. Eur. 2.2.35 |
| 10 | TVACA | Ph. Eur. 2.6.12 |
| 11 | Bacterial endotoxins | Pyrogen test |

Results are shown in FIGS. 16 and 17.

Visual inspection (visible particles, colour, and clarity) was conducted according to the Ph. Eur. (i.e. in front of a black and white background). However, the inspection was carried out directly into the vials as the amount of sample available did not allow transfer into standardised Ph. Eur. tubes. The visual inspection for visible particles, clarity and colour was conducted by 2 operators.

No significant change in colour and clarity after 6 months storage at different temperatures was observed in both formulations. No trend in colour and clarity as a function of storage temperature was observed in these samples. The colour of the samples was reported as "not more coloured than B9/BY7/Y7" since they were as colourless as water for injection. The clarity of the samples was reported as "<Ref I" since they were also as clear as water for injection. The placebo batch F531-03-003P063 was practically free of visible particles at all storage temperatures and time points. However, the DP batch F531-03-003P064B showed a trend for visible particles as a function of storage temperature and time. At release, the sample was practically free of visible particles. DP samples stored at −20° C. and 5° C. were still practically free of visible particles at t=1 month. At t=3 and t=6 month time points, 5-10 fibre-like particles were observed in the samples stored at −20° C. and 5° C. However, this was still reported as practically free of visible particles because the amount was less than 10. Interestingly, there was no increase in the number of particles detected in the samples stored at −20° C. and 5° C. from t=3 months to t=6 months. Identification of the nature of the particles (i.e. proteinaceous or non-proteinaceous) as well as visual inspection of vials stored for a longer period would be required to confirm that these particles are an indication of the instability of CD-RAP DP batch at −20° C. and 5° C. After 6 months storage, the samples stored at −80 °C showed 20-30 fibre-like particles, which was more than what was detected in the samples stored at −20° C. for the same period. Thus, storage at −80° C. does not present any advantage over storage at −20° C. At 25° C., samples were still practically free of visible particles at t=1 month. At t=3 and t=6 months these samples showed 20 and 10-20 fibre-like particles, respectively. At 40° C., samples showed more than 10 white fibre-like particles at t=1 month. Taken together, this might be an indication of instability of the CD-RAP DP at 40° C. after 1 month storage and at 25° C. after 3 months storage. Overall, visible particle results indicate that CD-RAP DP would be the most stable at −20° C. and 5° C. after 6 months storage.

No change in pH after 6 months storage at different temperatures was observed in both formulations. The pH of the samples remained 6.0-6.1.

The osmolality of the CD-RAP DP and placebo batches was analysed at release and at t=6 months. There was no change in the osmolality of the formulations throughout the study, which was 315-319 mOsm/kg and 309-313 mOsm/kg for the DP and placebo batch, respectively. This was expected, as osmolality is usually not a stability-indicating parameter.

No peak from the placebo batch interfered with the DP batch in any of the samples via RP-HPLC. A gradual decrease of CD-RAP content "as is" as well as of CD-RAP purity was observed as a function of storage temperature and time. This was combined by an increase in % Ox-Met-SAR396049 and in % largest impurity besides Ox-Met-SAR396049. At −80° C., the % Ox-Met-SAR396049 and % largest impurity besides Ox-Met-SAR396049 both showed a 0.4% increase after 6 months storage compared to the values obtained at release (from 6.6% to 7.0% and from 1.5% to 1.9%, respectively). At −20° C., a similar trend was observed over the same period (increase of 0.6% and 0.4% compared to release for both impurity types). During the whole study the overall CD-RAP purity decrease was about 1% (from 85.0% at t=0 to 83.9% at t=6 months) and CD-RAP content "as is" decreased from 2.2 to 2.0 mg/ml at both storage temperatures. At 5° CC the same trend as that observed at −80° C. and −20° C. was observed with the exception that the increase in % Ox-Met-SAR396049 was more important at that temperature (from 6.6% at release to 7.5% at t=6 months). This was accompanied by a decrease in CD-RAP purity of 1.5% (from 85.0% to 83.5%). At 25° C., the % Ox-Met-SAR396049 increased from 6.6% at release to 8.2% and 8.9% after 3 and 6 months storage, respectively. The % Ox-Met obtained at t=6 months at that temperature was almost equivalent to that obtained in the samples stored at 40° C. after 1 month (9.1%). The % largest impurity besides Ox-Met-SAR396049 also increased from 1.5% at release to 2.8% after 6 months storage at 25° C. Similarly to what was observed with visible particles, these results might be a sign of instability of CD-RAP DP when stored at 25° C. from 3 months onward and at 40° C. for 1 month.

No aggregates were observed in CD-RAP DP batch F531-03-003P064B at all storage temperatures over 6 months via HPSEC. No peak from the placebo interfered with the DP batch in any of the samples.

Based on the results obtained in this study, it can be concluded that the CD-RAP protein solution was the most stable when stored at −20° C. and at 5° C. Storage at −80° C. did not present a clear advantage over storage at −20° C.

Example 7: Establishing Solvent Injection Method Producing Empty Liposomes

The aim of this study was to develop liposomal formulation of CD-RAP suitable for intra-articular administration and allowing to be freeze-dried by improving the process currently used to prepare the liposomes and modifying the composition of the formulation (e.g. lipids).

A scheme of the general process for the preparation of empty liposomes using a solvent injection method is shown in FIG. 17. The organic solvent mixture containing the lipids was injected in a controlled manner into the water phase using a peristaltic pump. A static mixer was inserted in the set-up for mixing the two liquids, as shown in FIG. 17. The injection was performed in front of the static mixer for increased turbulence, a condition that is favorable for liposome formation. The amount of organic solvent after injection was 10% (v/v) to allow instant liposome formation. This process was conducted at ambient temperature. After lipid injection, the result was empty liposomes in water containing 10% organic solvent. The empty liposome suspension was washed with water to remove the organic solvents. This was performed by tangential flow filtration (TFF). This process can remove >99.5% of the organic solvent.

The CD-RAP solution was produced at a CD-RAP concentration of approximately 5 mg/ml in an arginine-sodium phosphate (arg-phosphate) buffer, pH 7.3-7.4 (arginine 350 mM, sodium dihydrogen phosphate 50 mM, pH adjusted with phosphoric acid).

Prior to test the solvent injection method, solubility tests were performed with the lipids in order to find a solvent mixture in which all lipids could be solubilised. To keep the process simple, a solvent mixture had to be found in which the lipids can be solubilised at ambient temperature. The following lipids and solvents were tested:

Lipids: —Soy PC, —Ascorbyl palmitate, —Cholesterol,
Solvents: —Ethanol (96%), —TBA (95%), —Acetone, —DMSO, —DMA The solubility of soy PC and ascorbyl palmitate was tested in ethanol and TBA. Cholesterol was tested in acetone, DMSO and DMA. In all cases the lipids were weighted and the applicable solvent was added. To the mixtures that became clear (i.e. in which the lipids were dissolved), additional lipids were added. To the mixtures that did not become clear, additional solvent was added. The solubility was assessed visually.

Results of this experiment are shown in FIG. 19. It was concluded that the soy PC and ascorbyl palmitate could be dissolved in ethanol (96%), while DMA was the best solvent for cholesterol. Although the solubility of ascorbyl palmitate was higher in TBA (95%), it is more convenient to use one solvent for multiple lipids. To obtain one clear lipid solution at ambient temperature, the two lipid solutions ethanol:DMA were mixed in a ratio of 3:1. The final lipid solution containing all lipids in an ethanol/DMA mixture was clear at ambient temperature.

Soy lecithin and ascorbyl palmitate were dissolved in ethanol (96%) and cholesterol in DMA. Since DMA is a class 2 solvent, it was preferred to switch to a class 3 solvent. A class 3 solvent that was able to dissolve the cholesterol and form a clear solution at ambient temperature when mixed with the other lipids was 1-propanol. No changes were made to the amount of solvent used.

TABLE 11

Amount of lipids solubilised in ethanol and 1-propanol

| | Lipid amount (mg) | Ethanol (96%) (ml) | 1-Propanol (ml) |
|---|---|---|---|
| Soy lecithin | 1216 | 37.5 | |
| Ascorbyl palmitate | 1.636 | | |
| Cholesterol | 409.1 | | 12.5 |

Effect of the Concentration of the Lipid Organic Solution

The lipid concentration in the organic solvent can have an effect on particle size after solvent injection. Since the solvent injection method is based on the dilution of an organic solvent with a water phase to approximately 10% (v/v), a higher lipid concentration means that less water is needed and that less diluted liposomes are formed. On the other hand a higher concentration of lipids in the organic phase can lead to larger particle (liposome) sizes. The effect of lipid concentration was determined by injecting different concentrations of lipids using the same injection parameters.

FIG. 20 clearly shows the effect of lipid concentration in the organic phase. With a decrease in lipid concentration there is a decrease in particle size of the formed liposomes and a more narrow distribution of the particles (lower PDI). As the lipid concentration decreased, the liposomes became more diluted resulting in a higher concentration factor. The concentration factor indicates the number of times the bulk liposomal suspension after injection needs to be concentrated in order to reach the target lipid content prior to mixing with CD-RAP protein.

Effect of Static Mixer Size

A static mixer was used to mix the water and organic phase during the solvent injection. Different mixers are available with different configurations. One of these configurations is the internal diameter of the mixer. By changing the internal diameter the internal volume is changed and with this the mixing ratio of the organic and water phases.

Two batches were prepared using a different static mixer for each batch.

Small static mixer: internal diameter 5.3 mm
Large static mixer: internal diameter 12.6 mm All other injection parameters were the same for each batch. The effect of the mixer internal diameter on the particle size is shown in FIG. 21. From the results in FIG. 21 it can be concluded that liposomes prepared using a static mixer with a larger internal diameter were smaller in size and had a lower PDI.

Effect of Aqueous Phase Flow Rate

Changing the aqueous phase flow rate has an impact on the shear created in the static mixer and on the dilution of the organic solvent that is injected. Two batches were prepared to test this parameter. The large static mixer was used because this mixer was better suited for higher aqueous phase flows. With the exception of the aqueous phase flow, all injection parameters were the same for both batches. The results are shown in FIG. 21. Increasing the aqueous phase flow rate from 550 ml/min to 1100 ml/min led to a significant decrease in particle size and PDI. The Z-average decreased from 147 nm to 106 nm and the PDI from 0.213 to 0.193.

Increasing the solvent injection speed to 5 ml/min or even 10 ml/min, in combination with a higher aqueous phase speed of 2200 ml/min, results in comparable particle size data to that seen in the batches prepared with 1 ml/min injection speed. A higher injection speed up to 10 ml/min was thus feasible.

Combination

By combining the best settings for the parameters tested above, a batch was prepared. The optimal settings in above sections were: Lipid concentration in organic phase: 0.033 (g/ml); Static mixer internal diameter: Large (12.6 mm); Aqueous phase flow rate: 1100 (ml/min). Results are shown in FIG. 23. Combining the best settings from all tested parameters resulted in a liposome batch with a particle size of 72 nm and a PDI of 0.132.

Example 8: Liposome Mixing with CD-RAP Protein

After the liposome preparation and (if applicable) DS buffer exchange/concentration, both liquids were mixed in a liposome:CD-RAP ratio of 55:45. The particle size of the liposomes after mixing with buffer (used as placebo) and after mixing with CD-RAP was analysed. As can be seen in FIG. 24, there was no change in the liposome particle size after mixing with CD-RAP.

Example 9: Freeze Drying and Reconstitution

Two runs of freeze-drying were performed according to the programs given in FIGS. 25 A and B. In Run 2 (given in FIG. 25B) the primary drying was conducted at −10° C. instead of +5° C. as done in Run 1 (given in FIG. 25A). Freeze drying according the program given in FIG. 25A resulted in cakes with large cracks. After reconstitution of the cake, phase separation was observed after reconstitution was performed. Freeze drying according the program given in FIG. 25B resulted in cakes without cracks. After reconstitution of the cake, no phase separation was observed.

Reconstition of the cakes was conducted by taking the vial out of 5° C. fridge and immediately reconstituting the cake by adding the total reconstitution volume (1 mL) of water either step-wise or all-at-once at ambient temperature and shaking for 30 sec.

Example 10: Encapsulation Efficiency

The effect of different parameters on the encapsulation efficiency (EE) and ease of reconstitution was evaluated on a series of batches with the aim of determining which parameters led to the best EE %. Table 11 provides an overview over all formulations prepared.

TABLE 12

Formulations

| Formulation code | Description | Lipid content | Lipid content before freeze-drying | Lipid content after reconstitution | Lipid composition | Freeze-drying | Annealing | Vial size (ml) | Fill vol. (ml) | Arginine Conc. (mM) | pH | Buffer type | Particle size liposome before FD (nm) |
|---|---|---|---|---|---|---|---|---|---|---|---|---|---|
| F531-03-004P014C | Active | standard | standard | standard | Standard lipid composition | Controlled | N | 10 | 5.5 | 350 | 7.3 | Arginine/phosphate | 100-120 |
| F531-03-004P014D | Active | standard | standard | standard | Standard lipid composition | Controlled | N | 10 | 5.5 | 350 | 7.3 | Arginine/phosphate | 100-120 |
| F531-03-004P014E | Placebo | standard | standard | standard | Standard lipid composition | Controlled | N | 10 | 1.2 | 350 | 7.3 | Arginine/phosphate acid | 100-120 |
| F531-03-004P014F | Placebo | standard | standard | standard | Standard lipid composition | Controlled | N | 10 | 5.5 | 350 | 7.3 | Arginine/phosphate acid | 100-120 |
| F531-03-004P025F0 | Active | standard | standard | standard | Standard lipid composition | Controlled | N | 10 | 2.75 | 350 | 7.3 | Arginine/phosphate | 100-120 |
| F531-03-004P025F1 | Active | standard | standard | standard | Standard lipid composition | Controlled | N | 10 | 5.11 | 350 | 7.3 | Arginine/phosphate | 100-120 |
| F531-03-004P025F2 | Active | standard | standard | standard | Standard lipid composition | Controlled | N | 10 | 5.5 | 350 | 7.3 | Arginine/phosphate | 100-120 |
| F531-03-004P067D | Lipid:water 55:45 | standard | standard | standard | Standard lipid composition | Controlled | N | 10 | 5.5 | NA | NA | NA | 60-80 |
| F531-03-004P067L | Active | standard | standard | standard | Standard lipid composition | Controlled | N | 10 | 3 | 350 | 7.3 | Arginine/phosphate | 60-80 |

TABLE 12-continued

Formulations

| Formulation code | Description | Lipid content | Lipid content before freeze-drying | Lipid content after re-constitution | Lipid composition | Freeze-drying | Annealing | Vial size (ml) | Fill vol. (ml) | Arginine Conc. (mM) | pH | Buffer type | Particle size liposome before FD (nm) |
|---|---|---|---|---|---|---|---|---|---|---|---|---|---|
| F531-03-004P082A | Placebo | standard | standard | standard | Standard lipid composition | Controlled | N | 10 | 3 | 650 | 5.5 | Arginine/phosphate acid | 60-80 |
| F531-03-004P082B | Placebo | standard | standard | standard | Standard lipid composition | Controlled | N | 10 | 3 | 650 | 6.3 | Arginine/phosphate acid | 60-80 |
| F531-03-004P082C | Placebo | standard | standard | standard | Standard lipid composition | Controlled | N | 10 | 3 | 650 | 7.3 | Arginine/phosphate acid | 60-80 |
| F531-03-004P082D | Placebo | standard | standard | standard | Standard lipid composition | Controlled | N | 10 | 3 | 350 | 5.5 | Arginine/phosphate acid | 60-80 |
| F531-03-004P082E | Placebo | standard | standard | standard | Standard lipid composition | Controlled | N | 10 | 3 | 350 | 6.3 | Arginine/phosphate acid | 60-80 |
| F531-03-004P082F | Placebo | standard | standard | standard | Standard lipid composition | Controlled | N | 10 | 3 | 350 | 7.3 | Arginine/phosphate acid | 60-80 |
| F531-03-004P082G | Placebo | standard | standard | standard | Standard lipid composition | Controlled | N | 10 | 3 | 50 | 5.5 | Arginine/phosphate acid | 60-80 |
| F531-03-004P082H | Placebo | standard | standard | standard | Standard lipid composition | Controlled | N | 10 | 3 | 50 | 6.3 | Arginine/phosphate acid | 60-80 |
| F531-03-004P082J | Placebo | standard | standard | standard | Standard lipid composition | Controlled | N | 10 | 3 | 50 | 7.3 | Arginine/phosphate acid | 60-80 |
| F531-03-004P082K | Active | standard | standard | standard | Standard lipid composition | Controlled | N | 10 | 3 | 350 | 5.5 | Arginine/phosphate | 60-80 |
| F531-03-004P082L | Active | standard | standard | standard | Standard lipid composition | Controlled | N | 10 | 3 | 350 | 6.3 | Arginine/phosphate | 60-80 |
| F531-03-004P082M | Active | standard | standard | standard | Standard lipid composition | Controlled | N | 10 | 5.5 | 350 | 7.3 | Arginine/phosphate | 60-80 |
| F531-03-004P082N | Protein only | N.A. | N.A. | N.A. | N.A. | Controlled | N | 3 | 1 | 350 | 7.3 | Arginine/phosphate | 60-80 |
| F531-03-004P089G | Active | standard | standard | standard | Standard lipid composition | Controlled | N | 10 | 5.5 | 350 | 7.3 | Arginine/phosphate | 60-80 |
| F531-03-004P089H | Active | standard | standard | standard | Standard lipid composition | Controlled | N | 10 | 5.5 | 200 | 6 | Arginine/citrate | 60-80 |
| F531-03-004P089K | Placebo | standard | standard | standard | Standard lipid composition | Controlled | N | 10 | 5.5 | 200 | 6 | Arginine/citrate | 60-80 |
| F531-03-004P089L | Placebo | standard | standard | standard | Standard lipid composition | Controlled | N | 10 | 5.5 | 350 | 7.3 | Arginine/phosphate acid | 60-80 |
| F531-03-004P099B | Placebo | standard | standard | standard | Standard lipid composition | Christ FD | N | 10 | 5.5 | 350 | 7.3 | Arginine/phosphate acid | 60-80 |
| F531-03-004P099C | Active | standard | standard | standard | Standard lipid composition | Christ FD | N | 10 | 5.5 | 350 | 7.3 | Arginine/phosphate | 60-80 |
| F531-03-004P102G | Active | standard | standard | standard | Standard lipid composition | Controlled | N | 10 | 3 | 350 | 7.3 | Arginine/phosphate | 60-80 |
| F531-03-004P102G2 | Active | standard | standard | standard | Standard lipid composition | Christ FD | N | 10 | 3 | 350 | 7.3 | Arginine/phosphate | 60-80 |
| F531-03-004P102J | Active | standard | standard | standard | Standard lipid composition | Controlled | N | 10 | 3 | 59 | 7.3 | Arginine/phosphate | 60-80 |
| F531-03-004P102N | Active | standard | standard | standard | Standard lipid composition | Controlled | N | 10 | 3 | 350 | 7.3 | Arginine/phosphate | 140-150 |
| F531-03-008P014H | Active | standard | standard | standard | negatively charged liposomes with POPG | Christ FD | N | 3 | 1 | 350 | 7.3 | Arginine/phosphate | 40-50 |

TABLE 12-continued

Formulations

| Formulation code | Description | Lipid content | Lipid content before freeze-drying | Lipid content after reconstitution | Lipid composition | Freeze-drying | Annealing | Vial size (ml) | Fill vol. (ml) | Arginine Conc. (mM) | pH | Buffer type | Particle size liposome before FD (nm) |
|---|---|---|---|---|---|---|---|---|---|---|---|---|---|
| F531-03-008P014J | Active | standard | standard | standard | negatively charged liposomes with POPG | Christ FD | N | 3 | 1 | 350 | 7.3 | Arginine/phosphate | 40-50 |
| F531-03-008P018G | Active | standard | standard | standard | negatively charged liposomes with POPG | Christ FD | N | 3 | 1 | 350 | 7.3 | Arginine/phosphate | 40-50 |
| F531-03-008P018H | Active | standard | standard | standard | negatively charged liposomes with POPG | Christ FD | N | 3 | 1 | 38 | 7.3 | Arginine/phosphate | 40-50 |
| F531-03-008P027H | Active | standard, half protein (2×) | standard | 2× concentrated | Standard lipid composition | Christ FD | N | 10 | 3 | 350 | 7.3 | Arginine/phosphate | 60-80 |
| F531-03-008P027K | Active | High, double fill (2×) | standard | 2× concentrated | Standard lipid composition | Christ FD | N | 10 | 4.65 | 350 | 7.3 | Arginine/phosphate | 60-80 |
| F531-03-008P027F | Active | High, concentrated (2×) | 2× concentrated | 2× concentrated | Standard lipid composition | Christ FD | N | 10 | 3 | 350 | 7.3 | Arginine/phosphate | 60-80 |
| F531-03-008P031A | Active | High, concentrated (2×) | 2× concentrated | 2× concentrated | Standard lipid composition | Controlled | Y | 10 | 3 | 350 | 7.3 | Arginine/phosphate | 60-80 |
| F531-03-008P031B | Placebo | High, concentrated (2×) | 2× concentrated | 2× concentrated | Standard lipid composition | Controlled | Y | 10 | 3 | 350 | 7.3 | Arginine/phosphate | 60-80 |
| F531-03-008P031C | Active | standard | standard | standard | Standard lipid composition | Controlled | Y | 10 | 4.65 | 350 | 7.3 | Arginine/phosphate | 60-80 |
| F531-03-008P031D | Placebo | standard | standard | standard | Standard lipid composition | Controlled | Y | 10 | 3 | 350 | 7.3 | Arginine/phosphate | 60-80 |
| F531-03-008P033B | Placebo | High, concentrated (2×) | 2× concentrated | 2× concentrated | Standard lipid composition | Christ FD | N | 10 | 3 | 350 | 7.3 | Arginine/phosphate | 60-80 |
| F531-03-008P033D | Placebo | standard | standard | standard | Standard lipid composition | Christ FD | N | 10 | 3 | 350 | 7.3 | Arginine/phosphate | 60-80 |
| F531-03-008P033E | Active | standard | standard | standard | Standard lipid composition | Christ FD | N | 10 | 3 | 350 | 7.3 | Arginine/phosphate | 60-80 |
| F531-03-008P033F | Protein only | NA | NA | NA | NA | Christ FD | N | 10 | 3 | 350 | 7.3 | Arginine/phosphate | 60-80 |
| F531-03-008P041A | Active | High, concentrated (2×) | 2× concentrated | 2× concentrated | Standard lipid composition | Christ FD | N | 10 | 3 | 350 | 7.3 | Arginine/phosphate acid | 60-80 |
| F531-03-008P041B | Placebo | High, concentrated (2×) | 2× concentrated | 2× concentrated | Standard lipid composition | Christ FD | N | 10 | 3 | 350 | 7.3 | Arginine/phosphate acid | 60-80 |
| F531-03-008P041C | Active | High, concentrated (2×) | 2× concentrated | 2× concentrated | Standard lipid composition | Controlled | N | 10 | 3 | 350 | 7.3 | Arginine/phosphate acid | 60-80 |
| F531-03-008P041D | Placebo | High, concentrated (2×) | 2× concentrated | 2× concentrated | Standard lipid composition | Controlled | N | 10 | 3 | 350 | 7.3 | Arginine/phosphate acid | 60-80 |
| F531-03-008P041E | Active | High, concentrated (2×) | 2× concentrated | 2× concentrated | Standard lipid composition | Controlled | N | 6 | 1.8 | 350 | 7.3 | Arginine/phosphate acid | 60-80 |
| F531-03-008P041F | Placebo | High, concentrated (2×) | 2× concentrated | 2× concentrated | Standard lipid composition | Controlled | N | 6 | 1.8 | 350 | 7.3 | Arginine/phosphate acid | 60-80 |
| F531-03-008P041G | Active | High, concentrated (2×) | 2× concentrated | 2× concentrated | Standard lipid composition | Controlled | N | 3 | 1.8 | 350 | 7.3 | Arginine/phosphate acid | 60-80 |
| F531-03-008P041H | Placebo | High, concentrated (2×) | 2× concentrated | 2× concentrated | Standard lipid composition | Controlled | N | 3 | 1.8 | 350 | 7.3 | Arginine/phosphate acid | 60-80 |
| F531-03-008P050A | Active | High, concentrated (2×) | 2× concentrated | 2× concentrated | Standard lipid composition | Controlled | N | 3 | 1.8 | 350 | 7.3 | Arginine/phosphate | 60-80 |

TABLE 12-continued

Formulations

| Formulation code | Description | Lipid content | Lipid content before freeze-drying | Lipid content after reconstitution | Lipid composition | Freeze-drying | Annealing | Vial size (ml) | Fill vol. (ml) | Arginine Conc. (mM) | pH | Buffer type | Particle size liposome before FD (nm) |
|---|---|---|---|---|---|---|---|---|---|---|---|---|---|
| F531-03-008P050B | Placebo | High, concentrated (2×) | 2× concentrated | 2× concentrated | Standard lipid composition | Controlled | N | 3 | 1.8 | 350 | 7.3 | Arginine/phosphate | 60-80 |
| F531-03-008P050C | Active | High, concentrated (2×) | 2× concentrated | 2× concentrated | Standard lipid composition | Controlled | N | 3 | 1.8 | 200 | 6 | Arginine/citrate | 60-80 |
| F531-03-008P050D | Placebo | High, concentrated (2×) | 2× concentrated | 2× concentrated | Standard lipid composition | Controlled | N | 3 | 1.8 | 200 | 6 | Arginine/citrate | 60-80 |
| F531-03-008P050E | Active | High concentrated, high fill (3×) | 2× concentrated | 3× concentrated | Standard lipid composition | Controlled | N | 3 | 2.3 | 350 | 7.3 | Arginine/phosphate | 60-80 |
| F531-03-008P050F | Placebo | High concentrated, high fill (3×) | 2× concentrated | 3× concentrated | Standard lipid composition | Controlled | N | 3 | 2.3 | 350 | 7.3 | Arginine/phosphate | 60-80 |
| F531-03-008P050G | Active | High concentrated, high fill (3×) | 2× concentrated | 3× concentrated | Standard lipid composition | Controlled | N | 3 | 2.3 | 200 | 6 | Arginine/citrate | 60-80 |
| F531-03-008P050H | Placebo | High concentrated, high fill (3×) | 2× concentrated | 3× concentrated | Standard lipid composition | Controlled | N | 3 | 2.3 | 200 | 6 | Arginine/citrate | 60-80 |
| F531-03-008P050J | Active | High concentrated, high fill (4×) | 2× concentrated | 4× concentrated | Standard lipid composition | Controlled | N | 3 | 2.8 | 350 | 7.3 | Arginine/phosphate | 60-80 |
| F531-03-008P050K | Placebo | High concentrated, high fill (4×) | 2× concentrated | 4× concentrated | Standard lipid composition | Controlled | N | 3 | 2.8 | 350 | 7.3 | Arginine/phosphate | 60-80 |
| F531-03-008P050L | Active | High concentrated, high fill (4×) | 2× concentrated | 4× concentrated | Standard lipid composition | Controlled | N | 3 | 2.8 | 200 | 6 | Arginine/citrate | 60-80 |
| F531-03-008P050M | Placebo | High concentrated, high fill (4×) | 2× concentrated | 4× concentrated | Standard lipid composition | Controlled | N | 3 | 2.8 | 200 | 6 | Arginine/citrate | 60-80 |
| F531-03-008P050N | Protein only | NA | NA | NA | NA | Controlled | N | 3 | 1.8 | 350 | 7.3 | Arginine/phosphate | 60-80 |
| F531-03-008P050O | Protein only | NA | NA | NA | NA | Controlled | N | 3 | 1.8 | 200 | 6 | Arginine/citrate | 60-80 |
| F531-03-008P056E | Active | High, concentrated (4×) | 4× concentrated | 4× concentrated | Standard lipid composition | Controlled | N | 3 | 1.8 | 200 | 6 | Arginine/citrate | 60-80 |
| F531-03-008P056F | Active | High, concentrated (4×) | 4× concentrated | 4× concentrated | Standard lipid composition | Controlled | N | 6 | 1.8 | 200 | 6 | Arginine/citrate | 60-80 |
| F531-03-008P056G | Placebo | High, concentrated (4×) | 4× concentrated | 4× concentrated | Standard lipid composition | Controlled | N | 3 | 1.8 | 200 | 6 | Arginine/citrate | 60-80 |
| F531-03-008P056H | Active | High concentrated, high fill (6×) | 4× concentrated | 6× concentrated | Standard lipid composition | Controlled | N | 3 | 2.3 | 200 | 6 | Arginine/citrate | 60-80 |
| F531-03-008P056J | Active | High concentrated, high fill (6×) | 4× concentrated | 6× concentrated | Standard lipid composition | Controlled | N | 6 | 2.3 | 200 | 6 | Arginine/citrate | 60-80 |
| F531-03-008P056K | Placebo | High concentrated, high fill (6×) | 4× concentrated | 6× concentrated | Standard lipid composition | Controlled | N | 3 | 2.3 | 200 | 6 | Arginine/citrate | 60-80 |
| F531-03-008P056L | Active | High concentrated, high fill (8×) | 4× concentrated | 8× concentrated | Standard lipid composition | Controlled | N | 3 | 2.8 | 200 | 6 | Arginine/citrate | 60-80 |
| F531-03-008P056M | Active | High concentrated, high fill (8×) | 4× concentrated | 8× concentrated | Standard lipid composition | Controlled | N | 6 | 2.8 | 200 | 6 | Arginine/citrate | 60-80 |
| F531-03-008P056N | Placebo | High concentrated, high fill (8×) | 4× concentrated | 8× concentrated | Standard lipid composition | Controlled | N | 3 | 2.8 | 200 | 6 | Arginine/citrate | 60-80 |
| F531-03-008P064E1 | Active | High, concentrated (4×) | 4× concentrated | 4× concentrated | Standard lipid composition | Controlled slow | N | 6 | 1.8 | 200 | 6 | Arginine/citrate | 60-80 |
| F531-03-008P064E2 | Active | High, concentrated (4×) | 4× concentrated | 4× concentrated | Standard lipid composition | Controlled fast | N | 6 | 1.8 | 200 | 6 | Arginine/citrate | 60-80 |

TABLE 12-continued

Formulations

| Formulation code | Description | Lipid content | Lipid content before freeze-drying | Lipid content after reconstitution | Lipid composition | Freeze-drying | Annealing | Vial size (ml) | Fill vol. (ml) | Arginine Conc. (mM) | pH | Buffer type | Particle size liposome before FD (nm) |
|---|---|---|---|---|---|---|---|---|---|---|---|---|---|
| F531-03-008P064F1 | Active | High concentrated, high fill (6×) | 4× concentrated | 6× concentrated | Standard lipid composition | Controlled slow | N | 6 | 2.3 | 200 | 6 | Arginine/citrate | 60-80 |
| F531-03-008P064F2 | Active | High concentrated, high fill (6×) | 4× concentrated | 6× concentrated | Standard lipid composition | Controlled fast | N | 6 | 2.3 | 200 | 6 | Arginine/citrate | 60-80 |
| F531-03-008P074F | Active | High concentrated, high fill (6×) | 2× concentrated | 6× concentrated | Standard lipid composition | Controlled 1 C./min | N | 6 | 4 | 200 | 6 | Arginine/citrate | 60-80 |
| F531-03-008P074F | Active | High concentrated, high fill (6×) | 2× concentrated | 6× concentrated | Standard lipid composition | Controlled 1 C./min | N | 6 | 4 | 200 | 6 | Arginine/citrate | 60-80 |

Parameter Investigation Formulation F531-03-008P027, 008P031 & 008P033

Tested formulations had either a standard or 2× lipid content. Vials were reconstituted either in one step (i.e. by adding the total reconstitution volume at once), or step by step. The step by step reconstitution method was mentioned in the literature as a way of promoting higher molecule entrapment into liposomes. When using this method, reconstitution proceeds as follows: 1-30% of the total reconstitution volume is added, vial is manual swirled and rested for 30 min on the lab bench. 2—Step 1 is repeated 3—The remaining of the reconstitution volume is added, vial is manually swirled and rested for 30 min on the lab bench.

Using the step-by-step reconstitution method, all standard lipid content formulations were homogenous after the last reconstitution step. The 2× lipid content formulations were homogenous after a total 2 h rest period on the lab bench. When using the one step reconstitution method however, no lumps were visible in any of the formulations immediately after reconstitution and so, whatever the lipid content of the formulations. Thus, it seems that the one step reconstitution method led to easier reconstitution of the formulations After reconstitution, the liposomal suspensions were diluted 20-fold with arginine-phosphate buffer and treated with the direct VivaSpin method (centrifugation 4000 g, 5 min). The filtrate was analysed for free protein content by RP-HPLC. EE % was calculated using the theoretical amount of CD-RAP per vial as reference, which was obtained by multiplying the protein content in the DS used to prepare the batch (F-MPL-120004) by the amount of DS solution pipetted in the vial. It is worth noting that the volume of the reconstituted product was not measured in these batches, as the cake volume effect was discovered later in the project. Nevertheless, the EE % values in batches with the same lipid content can be compared to each other as their volume after reconstitution is equivalent.

An overview of the formulations tested and of the obtained EE % can be found in FIG. 26. The obtained EE % varied between 17 and 53%. The effect of each parameter investigated is discussed into more details in the following sections.

The reproducibility of the EE % results was tested by evaluating 2 or 3 vials from the same batch reconstituted in the same way. Reproducible data was obtained in formulations with standard lipid content. The results obtained for formulation P033A with 2× lipid content present more variability.

The effect of the lipid content were compared. EE % results should be interpreted with caution here due to the fact that no correction for the cake volume was made. Higher EE % was achieved with higher lipid content using both reconstitution methods. There was no effect of concentrating the liposomes prior to freeze-drying vs. upon reconstitution (compare form. P027K and P027F). Form. P027H was prepared with the standard lipid content, but by adding half the volume of CD-RAP solution. This led to a higher lipid:protein ratio as well. It can be seen that decreasing the protein content led to a lower EE %. This indicates that the lipsomes were not saturated with CD-RAP, since if the maximum amount of available protein would be encapsulated, a decrease in protein content would have led to an increase in EE %.

The effect of the lipid content on the particle size of the liposomes in the reconstituted product was also investigated. However, there was no impact of lipid content on liposome particle size and size distribution after reconstitution.

The effect of the freeze-drying method can be seen in FIG. 28A. For samples with a standard lipid content controlled freeze-drying led to better EE % than Christ freeze-drying. This trend was reverted in samples with 2× lipid content. Comparisons were difficult here given that the samples which underwent controlled freeze-drying were also subjected to an annealing step.

The effect of the reconstitution method on the particle size of the liposomes in the reconstituted product was also investigated. As can be seen in FIG. 28B, one step reconstitution led to a narrower particle size distribution.

Parameter Investigation Formulations F531-03-008P041 & 008P050

Tested formulations had either a 2×, 3×, or 4× lipid content. Vials were reconstituted with the one step method (i.e. by adding the total reconstitution volume at once). Using this method all formulations could be reconstituted. After reconstitution, the liposomal suspensions were diluted 20-fold with their corresponding buffer and treated with the direct VivaSpin method (centrifugation 4000 g, 5 min). The filtrate was analysed for free protein content by RP-HPLC. EE % was calculated using the theoretical amount of CD-RAP per vial as reference, which was obtained by multiplying the protein content in the DS used to prepare the batch (F-MPL-120004 or F-AKO-120006) by the amount of DS solution pipetted in the vial. It is worth noting that the volume of the reconstituted product was not measured in these batches, as the cake volume effect was discovered later in the project. Nevertheless, the EE % values in batches with the same lipid content can be compared to each other as their volume after reconstitution is equivalent.

The first series of formulations (F531-03-008P041A/C/E/G) was prepared with a 2× lipid content in order to evaluate:
—Repeatability and reproducibility of EE % in high lipid content samples after one step reconstitution—Effect of freeze-drying method (controlled vs. Christ) on EE %—The need for a rest period after reconstitution for 2× lipid content batches—Influence of vial size and filling volume on cake appearance, reconstitution and EE %

For the second series of formulations (F531-03-008P050A/C/E/G/J/L), the protein solution mixed with the liposomes was in either arg-phosphate or arg-citrate buffer. All batches were filled in 2R iso vials and freeze-dried in a controlled freeze-drier. With these batches, the effect of the following parameters was evaluated: —Repeatability and reproducibility of EE % in high lipid content samples after one step reconstitution—Influence of fill volume (to obtain high lipid content) on cake appearance and reconstitution—Effect of lipid concentration on EE %—Effect of protein buffer type on EE %

An overview of the formulations can be found in FIG. 29. The obtained EE % varied between 39 and 62%. The reproducibility of the EE % results was tested by evaluating 2 or 3 vials from the same batch. Larger variation was obtained in DP with 3 ml fill in 10R vial as compared to the DP with lower fill in small vials (3 ml and 6 ml). This could be caused by a more robust and reproducible reconstitution in small vials compared to in large vials. The method was repeatable for formulations with high lipid content. The RSD % or difference % were <10% in 3 ml vials. When the RSD % or difference % is <10%, the difference in free protein content obtained by the RP-HPLC method is <0.3 mg/ml. 8.2.1 Effect of vial size and fill volume. The effect of of vial size and fill volume on EE % can be compared in Table 71. No significant difference in EE % for 2× lipid content formulation was obtained for samples with different fill volume and in different vial size. More variation of EE % for 10 ml vial size was obtained as compared to the 6 ml and 3 ml vial size.

No significant difference in EE % for 2× lipid content samples was obtained for samples after 1 hour incubation or without incubation. Thus, the rest period after reconstitution of the 2× lipid content samples was not needed.

No significant difference in EE % for 2× lipid content samples could be observed between Christ freeze-drying and controlled freeze-drying.

The effect of the lipid content can also be compared. However, EE % results should be interpreted with caution here due to the fact that no correction for cake volume was made. For the DP batches in argphosphate buffer, a higher EE % was obtained as a function of the lipid content (40% to 62% when the amount of lipid was doubled). For the DP batches in arg-citrate buffer, there was no difference in the EE % of samples with 2× vs. 3× lipid content. However, the EE % increased form 40% to 51% from 2/3× to 4× lipid content.

For the DP batches with a 2× lipid content, there was no significant difference in EE % for the two different buffer types. For the DP batches with a 3× and a 4× lipid content however, a higher EE % was obtained for the formulations in arginine-phosphate buffer.

Parameter Investigation Formulations F531-03-008P056 & 008P064

Tested batches had a 4× lipid content before freeze-drying. This lipid concentration was too high and led to problems during sterile filtration of the liposomes. After reconstitution, they had either a 4×, 6×, or 8× lipid content.

The batches were prepared in arginine-citrate buffer, freeze-dried with controlled freeze-drying, and reconstituted with the one step method. After reconstitution, the liposomal suspensions were diluted 20-fold with citrate buffer and treated with the direct VivaSpin method (centrifugation 4000 g, 5 min). The filtrate was analysed for free protein content by RP-HPLC. For these batches, the volume of the reconstituted product was taken into account when evaluating the EE %.

Formulations F531-03-008P056E/F/H/J/L/M were prepared to evaluate the effect of the following parameters: —Lipid content (4λ/6×/8×), —Fill volume before freeze drying, —Vial size (6R/2R vials), Formulations F531-03-008P064E1/E2/F1/F2 were prepared to confirm the impact of the lipid content and to evaluate the effect of the freezing rate during freeze-drying. In addition to confirm which parameters led to the best EE %, the purpose of these batches was the selection of vial size/lipid content/fill volume/freezing rate for the final batches.

TABLE 13

Overview of formulation F532-03-008P056 sub-batches

| Formulation code | Description | Vial type | Total Fill (mL) | Reconstitution Volume (mL) |
|---|---|---|---|---|
| F531-03-008p056E | 4× lipid active | 2R | 1.8 | 1 |
| F531-03-008p056F | 4× lipid active | 6R | 1.8 | 1 |
| F531-03-008p056H | 6× lipid active | 2R | 2.3 | 1 |
| F531-03-008p056J | 6× lipid active | 6R | 2.3 | 1 |
| F531-03-008p056L | 8× lipid active | 2R | 2.8 | 1 |
| F531-03-008p056M | 8× lipid active | 6R | 2.8 | 1 |

TABLE 14

Overview of formulation F532-03-008P064 sub-formulations

| Samples | Description | Vial type | freezing type | Total Fill (mL) | Reconstitution Volume (mL) |
|---|---|---|---|---|---|
| F531-03-008P064E1_1 | 4× lipid active | 6R | slow | 1.8 | 1 |
| F531-03-008P064E1_2 | 4× lipid active | 6R | slow | 1.8 | 1 |
| F531-03-008P064E2_1 | 4× lipid active | 6R | fast | 1.8 | 1 |
| F531-03-008P064E2_2 | 4× lipid active | 6R | fast | 1.8 | 1 |
| F531-03-008P064F1_1 | 6× lipid active | 6R | slow | 2.3 | 1 |
| F531-03-008P064F1_2 | 6× lipid active | 6R | slow | 2.3 | 1 |
| F531-03-008P064F2_1 | 6× lipid active | 6R | fast | 2.3 | 1 |
| F531-03-008P064F2_2 | 6× lipid active | 6R | fast | 2.3 | 1 |

After freeze-drying, batches from the P056 series showed lifted and phase separated cakes due to an issue during the freeze-drying run. Therefore, reconstitution and EE % results have to be interpreted with caution for that batch. However, the effect of the different parameters can be compared. All samples in 6R vials could be reconstituted easily. No lumps were observed. Formulations P056H/L (6× and 8× lipid content in 2R vials) could however not be reconstituted. These findings demonstrate that for 6× and 8× lipid content, the vial size should be 6R.

Batches from the P064 series were freeze-dried using 2 different freezing rates: slow and fast. To conduct this experiment, the vials undergoing slow freezing were placed on the shelves of the freeze-dryer and frozen to −40° C. at a rate of 0.3° C./min. Once these vials were frozen, the vials undergoing fast freezing were placed on the shelves already at −40° C. After freeze-drying, all batches from the P064 series showed good cakes. All other samples could be reconstituted within 1 minute swirling. No lumps were observed. These results indicated that 8× lipid content could not lead to a viable product.

EE % results for the batches of the P056 series can be found in FIG. 30. It can be seen that the vial size made no difference. There seemed to be however a small effect of the lipid content. Thus, the effect of an increased lipid content was confirmed. However, it is far less important than what was observed. Overall, an EE of 30% can be achieved Example 11: Stability The stability of the liposomal CD-RAP formulation as well as that of its matching placebo was tested in a 3-month stability study. The formulations intended to be used in pharmacokinetic (PK) studies were tested with long-term/real-time storage conditions (−80° C., −20° C. and 5° C.) and accelerated storage conditions (25° C.). The stability was monitored for 3 months for all storage temperatures. During the 3 months of the study, the cake appearance, pH, particle size, as well as main band MW and purity (as determined by SDS-Page) did not change at different time points or at various storage temperatures. The placebo corresponding to the CD-RAP formulation showed no interference with the CD-RAP formulation. Overall, the results obtained in this study show that the liposomal freeze-dried CD-RAP was stable when stored at −80° C., −20° C. and 5° C. Storage at −80° C. and −20° C. did not present a clear advantage over storage at 5° C.

Two formulations were placed into the stability study: one drug product (DP) formulation and one placebo formulation matching the DP formulation as indicated in Tables 15, 16, and 17.

TABLE 15

Composition of the bulk filled into the vials placed into the stability study program before freeze-drying

| Formulation number | Formulation |
|---|---|
| F531-03-008P082K (liposomal CD-RAP Formulation) | 7 mg/ml liposomal CD-RAP, citrate buffer (20 mM, pH 6.0), arginine 200 mM |
| F531-03-008P082L (Placebo) | Citrate buffer (20 mM, pH 6.0), arginine 200 mM |

TABLE 16

Composition (per vial) of the batches selected in the stability study

| Compound | |
|---|---|
| Lipids | Amount per vial (mg) |
| Soy lechitin | 430.1 |
| Cholesterol | 144.4 |
| Ascorbyl palmitate | 0.58 |
| Aqueous phase | Amount per vial (mg) |
| CD-RAP* | 7 |
| Citric acid monohydrate | 4.2 |
| L-arginine base | 34.8 |

TABLE 16-continued

Composition (per vial) of the batches selected in the stability study

| Compound | |
|---|---|
| NaOH 1M** | 54.4 |
| Ortho-phosphoric acid 85%** | 17.9 |
| Water for injection (WFI) | 908.7 |
| Other | |
| Vial type | 6R |
| Fill volume (ml) | 4 (1 ml DS in buffer + 3 ml lipid suspension) |
| Reconstitution volume (ml) | 1.4 |
| Volume after reconstitution (ml) | 1.8 |

*Not in placebo F530-03-008P082L
**Not in their current form (i.e. dissociated and/or complexed)

TABLE 17

Composition of the batches placed into the stability study program after reconstitution in 1.4 ml WFI

| Formulation number | Formulation | Date of production |
|---|---|---|
| F531-03-008P082K (liposomal CD-RAP formulation) | 3.9 mg/ml liposomal CD-RAP, citrate buffer (11 mM, pH 6.0), arginine 111 mM | 8 Jul. 2013 |
| F531-03-008P082L (Placebo) | Citrate buffer (11 mM, pH 6.0), arginine 111 mM | 8 Jul. 2013 |

Storage Conditions and Preparation of Stability Samples

Formulations were inserted in stability cabinets. They were stored in upright position in different stability cabinets at −80° C., −20±5° C., 5±3° C., and 25±2° C. At indicated time points, samples were withdrawn from the cabinets and analyzed within two weeks. While awaiting analysis, samples were stored at 5° C. The parameters and test methods presented in Table 18 were used to evaluate the stability of the batches.

TABLE 18

Test parameters and methods used in this study

| No. | Parameter | Method |
|---|---|---|
| | Characterisation active | |
| 1 | Total content CD-RAP | Extraction/RP-HPLC (SOP-AP-Encapsulation efficiency, V04) |
| 2 | Content free CD-RAP | Filtration-centrifugation/RP-HPLC (SOP-AP-Encapsulation efficiency, VO4 |
| 3 | Encapsulation Efficiency | RP-HPLC (SOP-AP-Encapsulation efficiency, V04) |
| 4 | Purity free CD-RAP | Filtration-centrifugation/SDS-Page (silver staining reduced and non-reduced, method versions M-426-e0 and M-416-e2, respectively) |
| | General | |
| 5 | Cake appearance | Visual inspection (SOP-AP-Encapsulation efficiency, V04) |
| 6 | Appearance after reconstitution | Visual inspection in vial (SOP-AP-Encapsulation efficiency, V04) |
| 7 | Particle size after reconstitution | Laser diffraction (Malvern MasterSizer) |
| 8 | pH | Ph. Eur. 2.2.3 |
| 9 | Osmolality | Ph. Eur. 2.2.35 |
| 10 | Residual water content (Karl | Ph. Eur. 2.5.32 |

TABLE 18-continued

Test parameters and methods used in this study

| No. | Parameter | Method |
|---|---|---|
| 11 | TVAC | Ph. Eur. 2.6.12 |
| 12 | Endotoxins | Ph. Eur. 2.6.14 |

At release both the DP and placebo batches were homogenous suspensions anter reconstitution.

All stability results are presented in FIG. 31 for the CD-RAP and placebo formulations, respectively.

After 1 month storage, a lump was observed in one of the vials stored at 5° C. for the placebo batch, in one of the vials stored at 25° C. for the placebo batch, and in both vials stored at 25° C. for the CD_RAP formulation. These results suggest an influence of storage temperature on ease of reconstitution.

After 3 months storage, the samples stored at −80° C. did not showed any lumps. This was the case also for the vials of the placebo batch stored at −20° C. In contrast, lumps were observed in the DP vials stored at −20° C. At 5° C. and 25° C., lumps were seen in respectively one vial out of two and in both vials for the DP and placebo batches.

In general the product under study was difficult to reconstitute and the resulting suspension was viscous. Therefore, it is difficult to conclude that the inhomogeneity of the suspension often observed after reconstitution was the result of the instability of the product as a function of time and temperature.

Particle Size

The particle size of the liposomes after reconstitution was measured by DLS at release only. The z-average was 2.9 and 3.6 μm for the DP and placebo batches, respectively. This is in the same range than the results obtained by laser diffraction (D(0.5) 3.9 and 4.0 μm for DP and placebo batch, respectively). The size distribution showed a bimodal distribution for DP batch P082K. In the case of placebo batch P082L, the size distribution showed in addition the presence of small liposomes in one of the 2 vials analysed. Polydispersity index (Pdl) was broad (0.4 for both batches), which is always the case for multimodal size distributions. The particle size at release was similar for the DP and placebo batches and remained constant throughout the whole study. This implies that the presence of lumps after reconstitution (see above) did not impact the particle size of the batches.

pH

No change in pH after 6 months storage at different temperatures was observed in both formulations. The pH of the samples remained 6.2 and 6.1 for the CD-RAP and placebo formulation, respectively.

Total Protein Content

Total Protein Content Determined by the Extraction Method

The total CD-RAP content was 3.9±0.2 mg/ml during the study when the product was stored at −80° C., −20° C., and 5° C. One exception is the vials stored at −20° C. for 1 month, which showed a lower total protein content of 2.8 mg/ml. This result is likely to be an outlier. Indeed, CD-RAP total content was back to 3.9 mg/ml at t=3 months. Moreover, CD-RAP total content determined in the same vials using the cake volume method showed a result comparable to that obtained at release (3.8 mg/ml).

Samples stored at 25° C. showed a lower total protein content (3.5 mg/ml) compared to the samples stored at lower temperatures. As the total protein content should remain constant in a given batch, a decrease in content "as is" can only be the result of CD-RAP degradation leading to a decrease in CD-RAP main peak area %. Results obtained in this study show that this was the case. When comparing CD-RAP main peak area % of samples stored at −20° C. with those stored at 25° C. at a given time point, it can be seen that CD-RAP main peak area % decreased from 76% to 70% at t=1 month and from 70% to 63% at t=3 months.

Total Protein Content Determined by the Cake Volume Method

The total CD-RAP content was 3.9±0.3 mg/ml during the whole study. In contrast to the results obtained with the extraction method, there was no influence of the storage temperature on the total CD-RAP content. This was expected given the fact that this method does uses of the content "as is", but the theoretical CD-RAP concentration as reference. This theoretical concentration depends on the amount of protein solution filled per vial, and on the reconstitution volume.

Content of Free CD-RAP

The free CD-RAP content was 2.6±0.3 mg/ml during the whole study when the product was stored at −80° C., −20° C., and 5° C.

Samples stored at 25° C. showed a lower free protein content (2.2-2.3 mg/ml) compared to the samples stored at lower temperatures. Similarly to what was observed for the total protein content results obtained with the extraction method, the decrease in free protein content "as is" is the result of CD-RAP degradation leading to a decrease in CD-RAP main peak area %. This is especially true after 3 months storage, where the free protein content decreased from 2.7 mg/ml at 5° C. (CD-RAP main peak area 77%) to 2.3 mg/ml at 25° C. (CD-RAP main peak area 69%). These results support those obtained with the total protein content method and suggest that the freeze-dried liposomal CD-RAP DP is stable at temperatures up to 5° C. for at least 3 months, but is stable for less than 1 month when stored at 25° C.

Encapsulation Efficiency

The encapsulation efficiency (EE %) was calculated using the following equation:

$$EE\ \% = 100 - [\text{free protein (mg/ml)} / \text{total protein (mg/ml)} * 100]$$

In this calculation, the total protein content can be obtained either by the extraction method or by the cake volume method. It is worth noting that free protein content, total protein content, as well as EE % values presented in FIG. 31 are the average values obtained from the 2 vials that were analysed at each time point. For this reason, calculation of the EE % using the average data presented in FIG. 31 might lead to slightly different results than those presented.

EE % Using Total Protein Content Based on the Extraction Method

At release, the EE % was 33%. This EE % remained constant during the whole study (30-38%) with the exception of the vials stored at −20° C. for 1 month, which showed a lower EE % of 11%. This lower EE % was the result of the lower total protein content obtained with these samples, and is likely to be an outlier. The EE % remained constant even in samples stored at 25° C. in which a decrease in CD-RAP main peak area % was observed. This can be explained by the fact that in these samples, both the free and total protein content "as is" were decreased, resulting in relatively no change in the EE %.

EE % Using Total Protein Content Based on the Cake Volume Method

At release, the EE % was 33%. This EE % remained constant during the whole study (30-37%) when the product was stored at −80° C., −20° C., and 5° C. One exception is the vials stored at −80° C. for 3 months, which showed a lower EE % 20%. This is likely to have been caused by a slightly high free CD-RAP (2.9 mg/ml) combined with a slightly low total CD-RAP (3.6 mg/ml), which leads to lower encapsulated protein levels.

In samples stored at 25° C., higher EE % was obtained compared to release (40% and 44% at t=1 and t=3 months, respectively). This is the consequence in the low free CD-RAP content "as is" in these samples (2.2-2.3 mg/ml) combined with a total protein content not determined "as is". As a result, the decrease in free CD-RAP due to the decrease in CD-RAP main peak area % was not compensated by a decrease also in the total CD-RAP, and higher EE % were obtained.

Taken together, these results show that EE % results are dependent on the analytical method that is used to obtained total protein content. When instability is observed (i.e. when CD-RAP main peak area % decreases), the total protein content method based on extraction leads to more accurate EE % results, as the measured content is "as is" decreases similarly to what is observed for free protein content.

Overall, it can be concluded that the changes in EE % seen in this study were caused by method variability and/or by the choice of the total protein content analytical method and that overall, no change in EE % was observed over 3 months at all temperatures.

Osmolality

The osmolality of the liposomal CD-RAP DP and placebo batches was analysed at release only. The results were 270 and 253 mOsm/kg for the DP and placebo batch, respectively.

Residual Water Content

The residual water content of the freeze-dried liposomal CD-RAP DP and placebo batches was analysed at release and at t=3 months. The water content showed a trend as a function of storage temperature and time. The values found at release (0.15 and 0.11% for DP and placebo batch, respectively), were slightly increased at t=3 months. The extent of the increase was a function of storage temperature. After 3 months, samples stored at −80° C. and −20° C. did not show a significant difference compared to t=0. Samples stored at 5° C. and 25° C. however showed respectively a 0.08% and a 0.16-0.17% increase in water content over the same period. As the containers used in this study are known to be impermeable to water vapor, one possible explanation for these results is the diffusion of water present in the stoppers into the cake. A more thorough drying of the stoppers can be used in the preparation of future batches to prevent this from occurring. Overall, the increase in water content was small, as the water content was maximally 0.3% after 3 months.

TVAC

The TVAC was determined only at release using the pour plate method. The results for DP and placebo batches were <1 CFU/1 ml and <1 CFU/5 ml, which was within the compendial specification.

The invention claimed is:

1. A CD-RAP precursor fusion protein comprising:
   a) a pre-sequence, which comprises at its C-terminus a cleavage site; and,
   b) CD-RAP
   wherein the CD-RAP precursor fusion protein comprises the amino acid sequence of SEQ ID NO: 20.

2. A nucleic acid encoding the CD-RAP precursor fusion protein of claim 1.

3. A vector comprising the nucleic acid of claim 2.

4. A host cell comprising the CD-RAP precursor fusion protein of claim 1.

5. A host cell comprising the nucleic acid of claim 2.

6. A host cell comprising the vector of claim 3.

7. A method of producing native CD-RAP comprising:
   a) cleaving the pre-sequence from the CD-RAP precursor fusion protein of claim 1 at the C-terminus cleavage site of the pre-sequence by enzymatic cleavage; and
   b) removing the cleaved pre-sequence to produce the native CD-RAP.

8. A CD-RAP protein preparation comprising the native CD-RAP produced by the method of claim 7.

9. A composition comprising CD-RAP of claim 1, and at least one positively charged amino acid and a buffer.

10. A method of producing the composition of claim 9, comprising adding CD-RAP of claim 1, to a buffer comprising at least one positively charged amino acid.

11. A pharmaceutical comprising the composition of claim 8.

12. A pharmaceutical comprising the composition of claim 9.

13. A method of storing CD-RAP, comprising keeping CD-RAP in the composition of claim 9.

* * * * *